(12) United States Patent
Hall

(10) Patent No.: US 10,994,172 B2
(45) Date of Patent: *May 4, 2021

(54) SYSTEMS AND METHODS FOR INTEGRATED AUTOMATED SPORTS DATA COLLECTION AND ANALYTICS PLATFORM

(71) Applicant: SportsMEDIA Technology Corporation, Durham, NC (US)

(72) Inventor: Gerard J. Hall, Durham, NC (US)

(73) Assignee: SPORTSMEDIA TECHNOLOGY CORPORATION, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/677,138

(22) Filed: Nov. 7, 2019

(65) Prior Publication Data

US 2020/0070002 A1    Mar. 5, 2020

Related U.S. Application Data

(63) Continuation of application No. 16/148,451, filed on Oct. 1, 2018, now Pat. No. 10,471,304, which is a
(Continued)

(51) Int. Cl.
*A63B 24/00* (2006.01)
*G06K 9/00* (2006.01)
(Continued)

(52) U.S. Cl.
CPC ........ *A63B 24/0062* (2013.01); *A61B 5/0022* (2013.01); *A61B 5/02055* (2013.01);
(Continued)

(58) Field of Classification Search
CPC . A63B 24/0062; A63B 5/0022; A63B 5/1122; A63B 5/02055; A63B 5/6802;
(Continued)

(56) References Cited

U.S. PATENT DOCUMENTS 5,917,553 A    6/1999  Honey et al.
6,133,946 A   10/2000  Cavallaro et al.
(Continued)

*Primary Examiner* — Hirdepal Singh
(74) *Attorney, Agent, or Firm* — Neo IP

(57) ABSTRACT

Systems, methods, and apparatus for data analytics for a sports activity are disclosed. A multiplicity of sensors tracks a multiplicity of world objects related to the sports activity, collects and communicates tracking data to a server platform in real time or near real time. The server platform integrates the tracking data from the multiplicity of sensors and scoring data for the sports activity, and correlates the tracking data and the scoring data with a corresponding UTC timecode based on rules related to the sports activity, thereby creating a multiplicity of UTC-coded data sets. The server platform synchronizes the multiplicity of UTC-coded data sets, thereby creating a time-synchronized data set. The server platform provides analytics based on the time-synchronized data set, thereby creating analyzed data. The multiplicity of user devices displays the analyzed data based on at least one application program.

19 Claims, 122 Drawing Sheets

Related U.S. Application Data continuation-in-part of application No. 15/450,191, filed on Mar. 6, 2017, now Pat. No. 10,086,231.

(60) Provisional application No. 62/624,534, filed on Jan. 31, 2018, provisional application No. 62/305,219, filed on Mar. 8, 2016.

(51) Int. Cl.
| | |
|---|---|
| *G06T 15/00* | (2011.01) |
| *G06F 16/901* | (2019.01) |
| *A61B 5/11* | (2006.01) |
| *A61B 5/0205* | (2006.01) |
| *H04Q 9/00* | (2006.01) |
| *A61B 5/00* | (2006.01) |
| *G11B 27/00* | (2006.01) |
| *A61B 5/024* | (2006.01) |
| *G16H 20/30* | (2018.01) |
| *G16H 40/67* | (2018.01) |
| *A61B 5/08* | (2006.01) |

(52) U.S. Cl.
CPC .......... *A61B 5/1112* (2013.01); *A61B 5/6802* (2013.01); *G06F 16/9024* (2019.01); *G06K 9/00342* (2013.01); *G06T 15/005* (2013.01); *G11B 27/00* (2013.01); *H04Q 9/00* (2013.01); *A61B 5/024* (2013.01); *A61B 5/08* (2013.01); *A61B 5/4875* (2013.01); *A61B 5/681* (2013.01); *A61B 5/6803* (2013.01); *A61B 5/6804* (2013.01); *A61B 5/6895* (2013.01); *A61B 5/746* (2013.01); *A61B 2503/10* (2013.01); *A61B 2560/0242* (2013.01); *G16H 20/30* (2018.01); *G16H 40/67* (2018.01)

(58) Field of Classification Search
CPC ....... A63B 5/681; A63B 5/4875; A63B 5/746; A63B 5/024; A63B 5/6803; A63B 5/6895; A63B 2560/0242; A63B 5/6804; A63B 5/08; A63B 2503/10; G06F 16/9024; G11B 27/00; H04Q 9/00; G06K 9/00342; G06T 15/005; G16H 20/30; G16H 40/67
USPC ...................................................... 340/573.1
See application file for complete search history.

(56) References Cited

U.S. PATENT DOCUMENTS

| | | | |
|---|---|---|---|
| 6,141,060 A | 10/2000 | Honey et al. |
| 6,266,100 B1 | 7/2001 | Gloudemans et al. |
| 6,292,130 B1 | 9/2001 | Cavallaro et al. |
| 6,304,665 B1 | 10/2001 | Cavallaro et al. |
| 6,456,232 B1 | 9/2002 | Milnes et al. |
| 7,075,556 B1 | 7/2006 | Meier et al. |
| 7,138,963 B2 | 11/2006 | Hobgood et al. |
| 7,154,540 B2 | 12/2006 | Honey et al. |
| 7,341,530 B2 | 3/2008 | Cavallaro et al. |
| 7,492,363 B2 | 2/2009 | Meier et al. |
| 7,552,031 B2 | 6/2009 | Vock et al. |
| 7,627,451 B2 | 12/2009 | Vock et al. |
| 7,750,901 B2 | 7/2010 | Meier et al. |
| 7,928,976 B2 | 4/2011 | Meier et al. |
| 8,077,981 B2 | 12/2011 | Elangovan et al. |
| 8,079,247 B2 | 12/2011 | Russell et al. |
| 8,253,799 B2 | 8/2012 | Elangovan et al. |
| 8,279,286 B2 | 10/2012 | Wagg et al. |
| 8,289,185 B2 | 10/2012 | Alonso |
| 8,315,432 B2 | 11/2012 | Lefevre et al. |
| 8,335,345 B2 | 12/2012 | White et al. |
| 8,400,302 B2 | 3/2013 | Russell et al. |
| 8,456,526 B2 | 6/2013 | Gloudemans et al. |
| 8,466,794 B2 | 6/2013 | Mack et al. |
| 8,477,046 B2 | 7/2013 | Alonso |
| 8,482,612 B2 | 7/2013 | Tamir et al. |
| 8,558,883 B2 | 10/2013 | Cavallaro et al. |
| 8,593,286 B2 * | 11/2013 | Razoumov ......... A63B 24/0062 340/573.1 |
| 8,705,799 B2 | 4/2014 | White et al. |
| 8,786,415 B2 | 7/2014 | Cavallaro et al. |
| 8,860,570 B2 | 10/2014 | Thomas et al. |
| 8,884,741 B2 | 11/2014 | Cavallaro et al. |
| 8,989,880 B2 | 3/2015 | Wohl et al. |
| 9,014,830 B2 | 4/2015 | Wohl |
| 9,035,776 B2 | 5/2015 | Robert |
| 9,044,198 B2 | 6/2015 | Benzel et al. |
| 9,058,670 B2 | 6/2015 | Birenboim et al. |
| 9,076,041 B2 | 7/2015 | Bentley et al. |
| 9,094,615 B2 | 7/2015 | Aman et al. |
| 9,180,357 B2 | 11/2015 | Richley |
| 9,186,548 B2 * | 11/2015 | House ................. H04N 5/2625 |
| 9,220,444 B2 | 12/2015 | Russell |
| 9,235,765 B2 | 1/2016 | Bentley et al. |
| 9,247,212 B2 | 1/2016 | Bose et al. |
| 9,406,131 B2 | 8/2016 | Würmlin et al. |
| 9,625,321 B2 | 4/2017 | Cavallaro et al. |
| 9,846,805 B2 | 12/2017 | Painter |
| 10,412,440 B2 | 9/2019 | Paul et al. |
| 2003/0182620 A1 | 9/2003 | Errico et al. |
| 2007/0121425 A1 | 5/2007 | Eble et al. |
| 2008/0192116 A1 | 8/2008 | Tamir et al. |
| 2009/0210395 A1 | 8/2009 | Sedam |
| 2010/0026809 A1 | 2/2010 | Curry |
| 2011/0090344 A1 | 4/2011 | Gefen et al. |
| 2011/0238853 A1 | 9/2011 | Paul et al. |
| 2012/0139731 A1 | 6/2012 | Razoumov et al. |
| 2012/0154593 A1 | 6/2012 | Anderson |
| 2012/0326873 A1 | 12/2012 | Utter |
| 2014/0219550 A1 | 8/2014 | Popa et al. |
| 2014/0310243 A1 * | 10/2014 | McGee ................. G06F 16/27 707/639 |
| 2015/0040685 A1 | 2/2015 | Nicholson et al. |
| 2015/0097700 A1 | 4/2015 | Holthouse |
| 2015/0131845 A1 | 5/2015 | Forouhar et al. |
| 2015/0148129 A1 | 5/2015 | Austerlade et al. |
| 2015/0149837 A1 | 5/2015 | Alonso et al. |
| 2015/0206409 A1 | 7/2015 | Visvanathan et al. |
| 2015/0208044 A1 | 7/2015 | Jacobson et al. |
| 2015/0248917 A1 | 9/2015 | Chang et al. |
| 2015/0306486 A1 | 10/2015 | Logan et al. |
| 2015/0317801 A1 | 11/2015 | Bentley et al. |
| 2015/0356332 A1 | 12/2015 | Turner et al. |
| 2015/0375083 A1 * | 12/2015 | Stelfox ................. A63F 13/65 700/91 |
| 2015/0381947 A1 | 12/2015 | Renkis |
| 2016/0232685 A1 | 8/2016 | Hefetz et al. |
| 2016/0314818 A1 | 10/2016 | Kirk et al. |
| 2016/0320941 A1 | 11/2016 | McQuistan et al. |
| 2017/0090554 A1 | 3/2017 | Pececnik |
| 2017/0098331 A1 | 4/2017 | Jiang et al. |
| 2017/0140629 A1 | 5/2017 | Briggs et al. |
| 2017/0172222 A1 | 6/2017 | Morgenthau et al. |
| 2017/0187704 A1 * | 6/2017 | Agnew ............... H04L 63/0281 |
| 2017/0201779 A1 | 7/2017 | Publicover et al. |
| 2017/0219707 A1 | 8/2017 | Cavallaro et al. |
| 2017/0224214 A1 * | 8/2017 | Saigh .................. A61B 5/6801 |
| 2017/0238055 A1 | 8/2017 | Chang et al. |
| 2017/0259115 A1 | 9/2017 | Hall |
| 2018/0077345 A1 | 3/2018 | Yee |
| 2019/0030397 A1 | 1/2019 | Hall |

* cited by examiner

| Company | Form | Image | Use |
|---|---|---|---|
| OM Signal | Shirt |  | Heart rate, breathing rate, push score, steps, calorie count |
| Hexoskin | Shirt only |  | Heart rate, breathing rate, breathing volume, steps, cadence, calories |
| Athos | Shirt and pant | 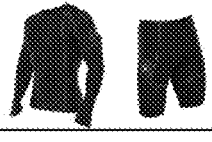 | Muscle Activity, heart rate, breathing |
| SmartLife | Shirts and clothing | 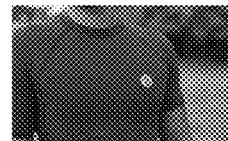 | Heart rate, respiration rate and calories |
| AIQ Bio Man | Shirts | 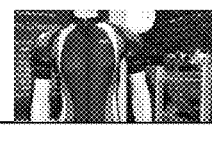 | Heart rate, respiration rate, skin temp |
| Myontech | Muscle sensing shorts |  | Muscle activity, muscle load and balance |
| Electricfoxy | Pants with sensors and baby hat with a camera | 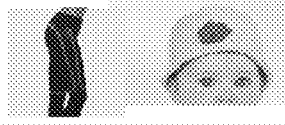 | Measure balance and loads |

FIG. 7

| Company | Form | Image | Use |
|---|---|---|---|
| Fitbit | Wearable (wrist) |  | GPS, heart rate, calories, pace/speed, distance |
| Jawbone | Wearable (wrist) |  | Heart rate, calories, pace/speed, distance, stride rate |
| Garmin | Wearable (wrist) |  | GPS, calories, heart rate, steps, distance, sleep |
| Schosche | Wearable (arm) |  | Heart rate and calories |
| Adidas | micoach fitsmart band (wrist) |  | Heart rate, calories, pace/speed, distance, stride rate |
| Under Armour | Grip Fitness Band (wrist) | 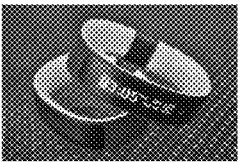 | Steps, distance, pace, calories, GPS |
| HALO | Wearable (wrist) |  | Hydration monitoring |
| Intel (Peak Fitness Tracker) | Wearable (wrist) |  | Heart rate, sleep |

FIG. 8

| Company | Form | Image | Use |
|---|---|---|---|
| Eccrine Systems/CoreSyte | Patch |  | Electrolytes, skin temp, lactic acid, hydration |
| Kenzen | Patch |  | Analyses sweat for Hydration, glucose, calorie count & lactic acid |
| MC10 | Patch | | |
| Gentag | Patch |  | Heart rate, temperature, hydration, lactic acid and electrolytes |
| U or Strathclyde | Patch | | Not ready for market. |
| Health Patch | Patch |  | Heart rate, respiratory, skin temp, activity, posture |

FIG. 9

| Company | Form | Image | Use |
|---|---|---|---|
| HQ Inc. | Ingestible |  | Core body temp |

| Company | OM Signal | Hexoskin | Kenzen | Gentag | HQ Inc. | Fitbit | Jawbone | Garmin |
|---|---|---|---|---|---|---|---|---|
| Category | Clothing | Clothing | Patch | Patch | Consumable | Band | Band | Band |
| Form | Shirt | Shirt | Patch | Patch | Pill | Wrist | Wrist | Wrist |
| Function | | | | | | | | |
| Heart rate | | | | | | | | |
| Breathing rate | | | | | | | | |
| Breathing volume | | | | | | | | |
| Steps | | | | | | | | |
| Pace/Speed | | | | | | | | |
| Calorie count | | | | | | | | |
| Hydration | | | | | | | | |
| Electrolytes | | | | | | | | |
| Lactic Acid | | | | | | | | |
| Temperature | | | | | | | | |
| Core Body Temp | | | | | | | | |
| GPS | | | | | | | | |
| Distance | | | | | | | | |
| Sleep | | | | | | | | |
| Other | Push Score | Breathing Volume | | | | | | |
| Use in Game/Practice | | | | | | | | |
| Care | Machine wash | Machine wash | Disposable | Disposable | Disposable | | | |
| Communication | Bluetooth | Bluetooth-Smart | Bluetooth LE | NFC | Bluetooth | Bluetooth | Bluetooth | Bluetooth |
| Battery Life | 12-14 hours | 14 hours | 7+ days | NFC | 24-48 hours | | | |
| Charge method | mini-USB | mini-USB | | N/A | N/A | USB | USB | USB |
| Market Position | Available to public and licensing | Available to public | In development and shipping in 2016 | Available to public | Available to public | Available to public | Available to public | Available to public |
| Cost | $275 | $400 | TBD | | $41 per pill | $250 | $200 | $200 |
| Company Location | Montreal, Canada | Montreal, Canada | Sweden | Washington, DC | Palmetto, FL | San Francisco, CA | San Francisco, CA | Olathe, KS |
| Positives | Market leader, longest in space, licensing technology | Product in market and available to public, been on market since 2013 | 7+ day battery life | NFC power, very thin, measures temperature, available to public | Can measure core body temp, available in the market, proven | Proven product, market leader, familiarity with product | Proven product, ease of use, familiarity with product | Proven product, ease of use, familiarity with product |
| Negatives | Black box could cause injury, cost | Hub on side could cause injury, cost | Prototype currently, doesn't measure temperature | NFC would have to be included in tag, location of patch near NFC source | $41 per pill, not made for contact, adoption concerns | Can't use during practice or games | Can't use during practice or games | Can't use during practice or games |

FIG. 11

| Company | Form | Image | Use |
|---|---|---|---|
| Riddell | HIT & Insite System | 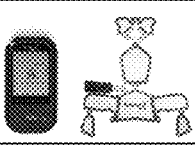 | Impacts to the head |
| Schutt | Helmet maker | | No system |
| Xenith | Helmet maker | | No system |
| G Force Tracker | In helmet and chin guard sensor |  | Impacts to the head |
| X2 Biosystems | Patch to measure impacts | 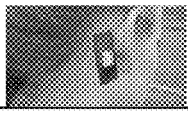 | Measures impacts to the head and neck |
| Stanford University | Mouthpiece to measure impacts |  | Measures impacts to the head with accelerometers in the mouthpiece |

FIG. 12

*Football Intelligence Engine*

| Football Intelligence Engine |
|---|
| # of plays for a player (game & season) |
| Biographical data (height, weight, etc) |
| Integrates Next Gen X,Y,Z (Live and Season to Date)     Position on field (start, during & end of play)     Position from ball |
| Integrates manual event markers (see marking app list) |
| Integrates LTC Truck Time Code Integrates QB Stat/GSIS data |

FIG. 13

Marking App

| | Time |
|---|---|
| | Start of Play |
| | End of Play |
| # | Time of Hand Off/QB release (Pitch) |
| | Start of Run with Ball |
| | End of Run with Ball |
| | QB Release of Pass |
| | Start of Route |
| | End of Route |
| | Reception |
| # | Time of 1st Contact |
| # | Tackle |
| | Player |
| | Targeted Receiver on Pass (input # of player) |
| # | Ball Carrier on Run (input # of player) |
| # | Tackler (input # of player) |

FIG. 14

*Prompter - Talent*

| Info Box - Offense |
|---|
| Personnel Group - Offense |
|     Offense - # of RB, OL, WR, TE |
|     # plays of grouping during game |
|     Total Yards gained with grouping |
|     Average yards gained with grouping |
| Personnel Group Alert - Offense |
|     6 - OL |
|     2 - TE |

| Info Box - Defense |
|---|
| Personnel Group - Defense |
|     Defense - # of DL, LB, DB |
|     Base D, Nickel or Dime |
|     # plays of grouping during game |
|     Total yards given up with grouping |
|     Average yards given up with grouping |
| Personnel Group Alert - Defense |
|     5 - DB (Nickel) |
|     6 - DB (Dime) |

| Main Screen - Alerts |
|---|
| Key Match Ups (predetermined before start of game) |
| 1st Time on Field (offense) |
| Mismatches (position, size, speed) |

FIG. 15

*Prompter - Researcher*

| Offense | |
|---|---|
| | # of running plays with grouping |
| | Rushing Yards with grouping |
| | Ave yards per play rushing with grouping |
| | # of passing plays with grouping |
| | Passing yards with grouping |
| | Ave yards per play passing with grouping |
| | Total yards with grouping |
| | Average yards per play with grouping |
| Defense | |
| | Running Plays Defended with grouping |
| | Rushing Yards given up with grouping |
| | Ave. Yards per rushing play given up with grouping |
| | # of times passed and completions |
| | Passing yards given up with grouping |
| | Ave. Yards per passing play given up with grouping |
| | Sacks with grouping |
| | Interceptions with grouping |
| | Average yards per play given up with grouping |

FIG. 16

*Game Report*

| Offense |
|---|

FIG. 17

Telestration & Sports CG - Offense

| Running Play | | |
|---|---|---|
| Bronze - Over Video | | |
| | T | Highlight RB with circle prior to play |
| | T | Trail RB during play starting at handoff |
| Bronze - Lower Third | | |
| | T & SCG | Player ID & Headshot |
| | | Yards to First Contact (Net & Gross) |
| | | Yards after First Contact (Net & Gross) |
| | | Yards Run (Gross) |
| | | Peak Speed |
| | | Net Gain/Loss |
| | | Efficiency |
| Silver | | |
| | | OL hole size and time open |
| | | Player Line-up Patterns at the snap |
| | |     RB (Left, Right, Behind QB, etc.) |
| | |     QB (Shotgun, Under Center, Wildcat) |
| | |     TE (On Line, Slot, Split Out) |
| | |     # of Players in the Box |

Continued on next page.

FIG. 18A

| Passing Play | |
|---|---|
| Bronze - Over Video | |
| T | Highlight WR with circle prior to play |
| T | Trail WR during play starting at snap |
| Bronze - Lower Third | |
| T & SCG | Player ID & Headshot |
| | Yards at Catch (Net) |
| | Yards after catch (Net) |
| | Yards run (Gross) |
| | Peak Speed |
| | Net Gain/Loss |
| Silver | |
| | QB Drop, Release & Rusher Proximity to QB |
| | WR - Match Up attributes with defender |
| | Distance between Player A and Player B |
| | Show Open or Covered (Color of trail) |
| | Open at release? (Intended and other receivers) |
| | Open at catch? |
| | Player Line-up Patterns at the snap |
| |     QB (Shotgun, Under Center, Wildcat) |
| |     TE (On Line, Slot, Split Out) |
| |     WR (Outside Numbers, Numbers, Slot) |
| |     # of Players in the Box |
| Special Teams Play | |
| Bronze - Over Video | |
| T | Highlight return man with circle prior to play |
| T | Trail returner during play starting at catch |
| Bronze - Lower Third | |
| T & SCG | Player ID & Headshot |
| | How far did he run (Gross) |
| | Peak Speed |
| | Net Gain |
| | Efficiency |
| Silver | |
| | Show holes (location, size) |
| | How close was defender when caught ball |

FIG. 18B

Telestration & Sports CG - Defense

| Running Play | | |
|---|---|---|
| Bronze - Over Video | | |
| | T | Highlight Tackler with circle prior to play |
| | T | Trail Tackler starting at snap |
| Bronze - Lower Third | | |
| | T & SCG | Player ID & Headshot |
| | | Yards Run (Gross) |
| | | Peak Speed |
| Silver | | |
| | | Distance from Ball Carrier at Hand Off |
| | | Proximity of Next Defender/Yards Saved |
| | | Player Line-up Patterns at the snap |
| | | Safety (2 Deep, In Box, At LOS) |
| | | Linebackers (In Box, At LOS, etc) |
| | | DL (TBD) |
| | | # of Players in the Box |

Continued on next page.

FIG. 19A

| Passing Play | |
|---|---|
| Bronze - Over Video | |
| T | Highlight DB with circle prior to play |
| T | Trail DB during play starting at snap |
| Bronze - Lower Third | |
| T & SCG | Player ID & Headshot |
| | Yards run (Gross) |
| | Peak speed |
| | Yards Saved by incomplete Pass |
| Silver | |
| | Where Lined Up - Match Up Attributes with WR |
| | How far lined up from WR |
| | Show Open or Covered (% of time) |
| | Open at release? (intended and other receivers) |
| | Open at Catch? |
| | Proximity of Next Defender/Yards Saved |
| | Player Line-up Patterns at the snap |
| |     Safety (2 Deep, In Box, At LOS) |
| |     Linebackers (In Box, At LOS, etc) |
| |     DL (TBD) |
| |     # of Players in the Box |
| Special Teams Play | |
| Bronze - Over Video | |
| T | Highlight Tackler with circle prior to play |
| T | Trail Tackler starting at kick |
| Bronze - Lower Third | |
| T & SCG | Player ID & Headshot |
| | Peak Speed |
| | Yards Run (Gross) |
| Silver | |
| | Distance from Receiver when caught |
| | Time from catch to tackle |
| | Proximity of Next Defender/Yards Saved |

FIG. 19B

_Sports CG - Participation_

| |
|---|
| Participation - On Field Pylon |
| Offense |
| Defense |
| By Personnel Groups (skilled players, Linemen, etc) |
| By Matchup (Star Receiver vs. Star DB) |
| By Substitution (personel grouping) |
| Player Route Charts (CBS Example) |
| Game Totals |
| By Down (ex. 3rd Down) |
| Last Drive |
| This Quarter |
| Last Quarter |
| Any Quarter |
| This Half |
| Last Half |

FIG. 20

*Offense*

| | | | |
|---|---|---|---|
| Running Play | | | |
| Prior to Play | | | |
| T | OV | Static | Personnel Grouping - Highlight Alignment (WR, TE, RB) |
| T | OV | Static | Highlight RB with circle prior to play |
| During Play | | | |
| T | OV | Dynamic | Trail RB during play starting at handoff |
| T & SCG | LT | Static | Player ID & Headshot |
| | LT | Dynamic | Yards to First Contact (Net) |
| | LT | Dynamic | Yards after First Contact (Net) |
| | LT | Dynamic | Peak Speed |
| After Play | | | |
| | LT | Static | Net Gain/Loss (play, game, season) |
| | LT | Static | Efficiency (play, game, season) |
| | LT | Static | Yards Run (Gross) (play, game, season) |
| | LT | Static | Peak Speed (play, game, season) |
| Passing Play | | | |
| Prior to Play | | | |
| T | OV | Static | Personnel Grouping - Highlight Alignment (WR, TE, RB) |
| T | OV | Static | Highlight WR with circle prior to play |
| During Play | | | |
| T | OV | Dynamic | Trail WR during play starting at snap |
| T & SCG | LT | Static | Player ID & Headshot |
| | LT | Dynamic | Yards at Catch (Net) |
| | LT | Dynamic | Yards after catch (Net) |
| | LT | Dynamic | Peak Speed |
| After Play | | | |
| | LT | Static | Net Gain/Loss (play, game, season) |
| | LT | Static | Yards run (Gross) (play, game, season) |
| | LT | Static | Peak Speed (play, game, season) |

Continued on next page.

FIG. 21A

| Special Teams Play | | | |
|---|---|---|---|
| Prior to Play | | | |
| T | OV | Static | Highlight return man with circle prior to play |
| During Play | | | |
| T | OV | Dynamic | Trail returner during play starting at catch |
| T & SCG | LT | Static | Player ID & Headshot |
| | LT | Dynamic | Yards to First Contact (Net) |
| | LT | Dynamic | Yards after First Contact (Net) |
| | LT | Dynamic | Peak Speed |
| After Play | | | |
| | LT | Static | Net Gain/Loss (play, game, season) |
| | LT | Static | Efficiency (play, game, season) |
| | LT | Static | Yards run (Gross) (play, game, season) |
| | LT | Static | Peak Speed (play, game, season) |

FIG. 21B

Defense

| Running Play | | | |
|---|---|---|---|
| Prior to Play | | | |
| T | OV | Static | Personnel Grouping - highlight DL, LB, DB |
| T | OV | Static | Highlight Tackler with circle prior to play |
| During Play | | | |
| T | OV | Dynamic | Trail Tackler during play starting at snap |
| T & SCG | LT | Static | Player ID & Headshot |
| | LT | Dynamic | Yards Run (Gross) |
| | LT | Dynamic | Peak Speed |
| After Play | | | |
| | LT | Static | Yards run (Gross) (play, game, season) |
| | LT | Static | Peak speed (play, game, season) |
| Passing Play | | | |
| Prior to Play | | | |
| T | OV | Static | Personnel Grouping - highlight DL, LB, DB |
| T | OV | Static | Highlight DB with circle prior to play |
| During Play | | | |
| T | OV | Dynamic | Trail DB during play starting at snap |
| T & SCG | LT | Static | Player ID & Headshot |
| | LT | Dynamic | Yards run (Gross) |
| | LT | Dynamic | Peak speed |
| After Play | | | |
| | LT | Static | Yards run (Gross) (play, game, season) |
| | LT | Static | Peak speed (play, game, season) |
| | LT | Static | Yards Saved by incomplete Pass (play, game, season) |
| Special Teams Play | | | |
| Prior to Play | | | |
| T | OV | Static | Highlight Tackler with circle prior to play |
| During Play | | | |
| T | OV | Dynamic | Trail Tackler starting at kick |
| T & SCG | LT | Static | Player ID & Headshot |
| | LT | Dynamic | Yards Run (Gross) |
| | LT | Dynamic | Peak Speed |
| After Play | | | |
| | LT | | Yards run (Gross) (play, game, season) |
| | LT | | Peak speed (play, game, season) |

FIG. 22

*Sports CG - Participation*

| | | | |
|---|---|---|---|
| Participation - On Field Pylon | | | |
| T | OV | Dynamic | Offense |
| | | | Defense |
| | | | By Personnel Groups (skilled players, Linemen, etc) |
| | | | By Matchup (Star Receiver vs. Star DB) |
| | | | By Substitution (personel grouping) |
| Player Route Charts (CBS Example) | | | |
| | | | Game Totals |
| | | | By Down (ex. 3rd Down) |
| | | | Last Drive |
| | | | This Quarter |
| | | | Last Quarter |
| | | | Any Quarter |
| | | | This Half |
| | | | Last Half |

Summary - Passing

| # | Name | Comp/Att | Yards | Ave/Play | TD | INT | Distance per Play | MAX Speed | AVE Speed | AVE Drop | Ave Release | Left | Middle | Right |
|---|---|---|---|---|---|---|---|---|---|---|---|---|---|
| TOTAL | | | | | | | | | | | | | | |
| 12 | T. Brady | 15/25 | 250 | 16.7 | 3 | 1 | 15 | 10 | | 5.2 | 2.8 | 5 of 7 | 5 of 10 | 5 of 8 |
| | Long | | 50 | | | | | | | | Yards | 150 | 50 | 50 |
| | Short | | -2 | | | | | | | | Ave | 30 | 10 | 10 |
| | | | | Receivers | | | | | | | TD | 1 | 2 | 0 |
| | | | | Gronkowski, Edelman, Amandola | | | | | | | | | | |
| UNDER CENTER | | | | | | | | | | | | | | |
| # | Name | Comp/Att | Yards | Ave/Play | TD | INT | Distance per Play | Max Speed | AVE Speed | AVE Drop | Ave Release | Left | Middle | Right |
| 12 | T. Brady | 10 of 15 | 200 | 20 | 3 | 1 | | | | 5.2 | 2.8 | 5 | 5 | 5 |
| | Long | | 50 | | | | | | | | Yards | 150 | 50 | 50 |
| | Short | | -2 | | | | | | | | Ave | 30 | 10 | 10 |
| | | | | Receivers | | | | | | | TD | 1 | 2 | 0 |
| | | | | Gronkowski, Edelman, Amandola | | | | | | | | | | |
| SHOTGUN | | | | | | | | | | | | | | |
| # | Name | Comp/Att | Yards | Ave/Play | TD | INT | Distance per Play | Max Speed | AVE Speed | AVE Drop | Ave Release | Left | Middle | Right |
| 12 | T. Brady | 5 of 10 | 50 | 10 | 3 | 1 | | | | 5.2 | 2.8 | 5 | 5 | 5 |
| | Long | | 50 | | | | | | | | Yards | 150 | 50 | 50 |
| | Short | | -2 | | | | | | | | Ave | 30 | 10 | 10 |
| | | | | Receivers | | | | | | | TD | 1 | 2 | 0 |
| | | | | Gronkowski, Edelman, Amandola | | | | | | | | | | |

Continued on next page.

FIG. 25A

Summary - Rushing

| # | Name | Attempts | Yards | Ave/Play | TD | Fumble | Distance | TOTAL Distance per Play | Max Speed | Ave Speed | Yards before Contact | Ave | Yards after Contact | Ave | Left | Middle | Right |
|---|---|---|---|---|---|---|---|---|---|---|---|---|---|---|---|---|---|
| 32 | T. Smith | 20 | 89 | 4.5 | 2 | 1 | 150 | 7.5 | | | 3.2 | | 5.2 | 2.8 Yards Ave TD | 5 of 7 150 30 1 | 5 of 10 50 10 2 | 5 of 8 50 10 0 |
| | Long | | 50 | | | | | | | | | | | | | | |
| | Short | | -2 | | | | | | | | | | | | | | |

Summary - Receiving

| # | Name | Rec/Tar | Yards | Ave/Play | TD | Fumble | Distance | TOTAL Distance per Play | Max Speed | Ave Speed | Yards at Catch | Ave | Yards after Catch | Ave | Left | Middle | Right |
|---|---|---|---|---|---|---|---|---|---|---|---|---|---|---|---|---|---|
| 32 | T. Smith | 20 | 89 | 4.5 | 2 | 1 | 150 | 7.5 | | | 3.2 | | 5.2 | 2.8 Yards Ave TD | 5 of 7 150 30 1 | 5 of 10 50 10 2 | 5 of 8 50 10 0 |
| | Long | | 50 | | | | | | | | | | | | | | |
| | Short | | -2 | | | | | | | | | | | | | | |

Summary - Blocking

| # | Name | Plays | Total Yards | Ave/Play | Distance | TOTAL Distance per Play | Max Speed | Ave Speed | Yards Pushing | Ave/Play | Yards Passing | Ave/Play | Sacks | Tackles for Loss |
|---|---|---|---|---|---|---|---|---|---|---|---|---|---|---|
| 32 | T. Smith | 20 | 89 | | | | | | | | | | | |

FIG. 25B

Summary - Passing

TOTAL

| # | Name | Comp/Att | Yards at Catch | Ave/Play | INT | Distance | Distance per Play | Max Speed | Ave Speed | Ave Drop | Ave Release | Left | Middle | Right |
|---|------|----------|----------------|----------|-----|----------|-------------------|-----------|-----------|----------|-------------|------|--------|-------|
| 12 | T. Brady | 15/25 | 250 | 16.7 | 1 | 15 | 10 | | | 5.2 | 2.8 | 5 of 7 / Yards 150 / Ave 30 / TD 1 | 5 of 10 / 50 / 10 / 2 | 5 of 8 / 50 / 10 / 0 |

UNDER CENTER

| # | Name | Comp/Att | Yards at Catch | Ave/Play | INT | Distance | Distance per Play | Max Speed | Ave Speed | Ave Drop | Ave Release | Left | Middle | Right |
|---|------|----------|----------------|----------|-----|----------|-------------------|-----------|-----------|----------|-------------|------|--------|-------|
| 12 | T. Brady | 10/15 | 200 | 20 | 1 | | | | | 5.2 | 2.8 | 5 / Yards 150 / Ave 30 / TD 1 | 5 / 50 / 10 / 2 | 5 / 50 / 10 / 0 |

SHOTGUN

| # | Name | Comp/Att | Yards at Catch | Ave/Play | INT | Distance | Distance per Play | Max Speed | Ave Speed | Ave Drop | Ave Release | Left | Middle | Right |
|---|------|----------|----------------|----------|-----|----------|-------------------|-----------|-----------|----------|-------------|------|--------|-------|
| 12 | T. Brady | 5 of 10 | 50 | 10 | 1 | | | | | 5.2 | 2.8 | 5 / Yards 150 / Ave 30 / TD 1 | 5 / 50 / 10 / 2 | 5 / 50 / 10 / 0 |

Continued on next page.

FIG. 26A

Summary - Rushing

| # | Name | Attempts | Yards | Ave/Play | Fumble | Distance | TOTAL Distance per Play | Max Speed | Ave Speed | Yards before Contact | Ave | Yards after Contact | Ave | Left | Middle | Right |
|---|---|---|---|---|---|---|---|---|---|---|---|---|---|---|---|---|
| 32 | T. Smith | 20 | 89 | 4.5 | 1 | 150 | 7.5 | | | 3.2 | | 5.2 | 2.8 | 5 of 7 | 5 of 10 | 5 of 8 |
| | Long | | 50 | | | | | | | | | | | Yards 150 | 50 | 50 |
| | Short | | -2 | | | | | | | | | | | Ave 30 | 10 | 10 |
| | | | | | | | | | | | | | | TD 1 | 2 | 0 |

Summary - Receiving

| # | Name | Rec/Tar | Yards | Ave/Play | Fumble | Distance | TOTAL Distance per Play | Max Speed | Ave Speed | Yards at Catch | Ave | Yards after Catch | Ave | Left | Middle | Right |
|---|---|---|---|---|---|---|---|---|---|---|---|---|---|---|---|---|
| 32 | T. Smith | 20 | 89 | 4.5 | 1 | 150 | 7.5 | | | 3.2 | | 5.2 | 2.8 | 5 of 7 | 5 of 10 | 5 of 8 |
| | Long | | 50 | | | | | | | | | | | Yards 150 | 50 | 50 |
| | Short | | -2 | | | | | | | | | | | Ave 30 | 10 | 10 |
| | | | | | | | | | | | | | | TD 1 | 2 | 0 |

Summary - Blocking

| # | Name | Plays | Total Yards | Ave/Play | Distance | Distance per Play | TOTAL Max Speed | Ave Speed | Yards Rushing | Ave/Play | Yards Passing | Ave/Play | Sacks | Tackles for Loss |
|---|---|---|---|---|---|---|---|---|---|---|---|---|---|---|
| 32 | T. Smith | 20 | 89 | | | | | | | | | | | |

FIG. 26B

Summary - Tackles

| # | Name | POS | Tackles | Yards | Ave/Play | TOTAL Distance | Distance per Play | Yards before Contact | Ave | Max Speed | Ave Speed |
|---|------|-----|---------|-------|----------|----------------|-------------------|----------------------|-----|-----------|-----------|

Summary - Sacks

| # | Name | POS | Sacks | Yards | Ave/Play | TOTAL Distance | Distance per Play | Yards before Contact | Ave | Max Speed | Ave Speed |
|---|------|-----|-------|-------|----------|----------------|-------------------|----------------------|-----|-----------|-----------|

Summary - Interceptions

| # | Name | POS | INT | Yards at INT | Ave | TOTAL Yards after INT | Ave | TD | Distance | Distance per Play | Max Speed | Ave Speed |
|---|------|-----|-----|--------------|-----|-----------------------|-----|-----|----------|-------------------|-----------|-----------|

Summary - Forced Fumble

| # | Name | POS | Forced Fumble | TD | Distance | TOTAL Distance per Play | Yards before Contact | Ave | Max Speed | Ave Speed |
|---|------|-----|---------------|-----|----------|-------------------------|----------------------|-----|-----------|-----------|

Summary - Fumble Recovery

| # | Name | POS | Fumble Recovery | Yards after Recovery | Ave | TD | TOTAL Distance | Distance per Play | Yards before Recovery | Ave | Max Speed | Ave Speed |
|---|------|-----|-----------------|----------------------|-----|-----|----------------|-------------------|-----------------------|-----|-----------|-----------|

FIG. 27

Summary - Tackles

| # | Name | POS | Tackles | Yards | Ave/Play | Distance | TOTAL Distance per Play | Yards before Contact | Ave | Max Speed | Ave Speed |
|---|------|-----|---------|-------|----------|----------|-------------------------|----------------------|-----|-----------|-----------|
|   |      |     |         |       |          |          |                         |                      |     |           |           |

Summary - Sacks

| # | Name | POS | Sacks | Yards | Ave/Play | Distance | TOTAL Distance per Play | Yards before Contact | Ave | Max Speed | Ave Speed |
|---|------|-----|-------|-------|----------|----------|-------------------------|----------------------|-----|-----------|-----------|
|   |      |     |       |       |          |          |                         |                      |     |           |           |

Summary - Interceptions

| # | Name | POS | INT | Yards at INT | Ave | TOTAL Yards after INT | Ave | Distance | Distance per Play | Max Speed | Ave Speed |
|---|------|-----|-----|--------------|-----|-----------------------|-----|----------|-------------------|-----------|-----------|
|   |      |     |     |              |     |                       |     |          |                   |           |           |

Summary - Forced Fumble

| # | Name | POS | Forced Fumble | TO | Distance | TOTAL Distance per Play | Yards before Contact | Ave | Max Speed | Ave Speed |
|---|------|-----|---------------|-----|----------|-------------------------|----------------------|-----|-----------|-----------|
|   |      |     |               |     |          |                         |                      |     |           |           |

Summary - Fumble Recovery

| # | Name | POS | Fumble Recovery | Yards after Recovery | Ave | Distance | TOTAL Distance per Play | Yards before Recovery | Ave | Max Speed | Ave Speed |
|---|------|-----|-----------------|----------------------|-----|----------|-------------------------|------------------------|-----|-----------|-----------|
|   |      |     |                 |                      |     |          |                         |                        |     |           |           |

FIG. 28

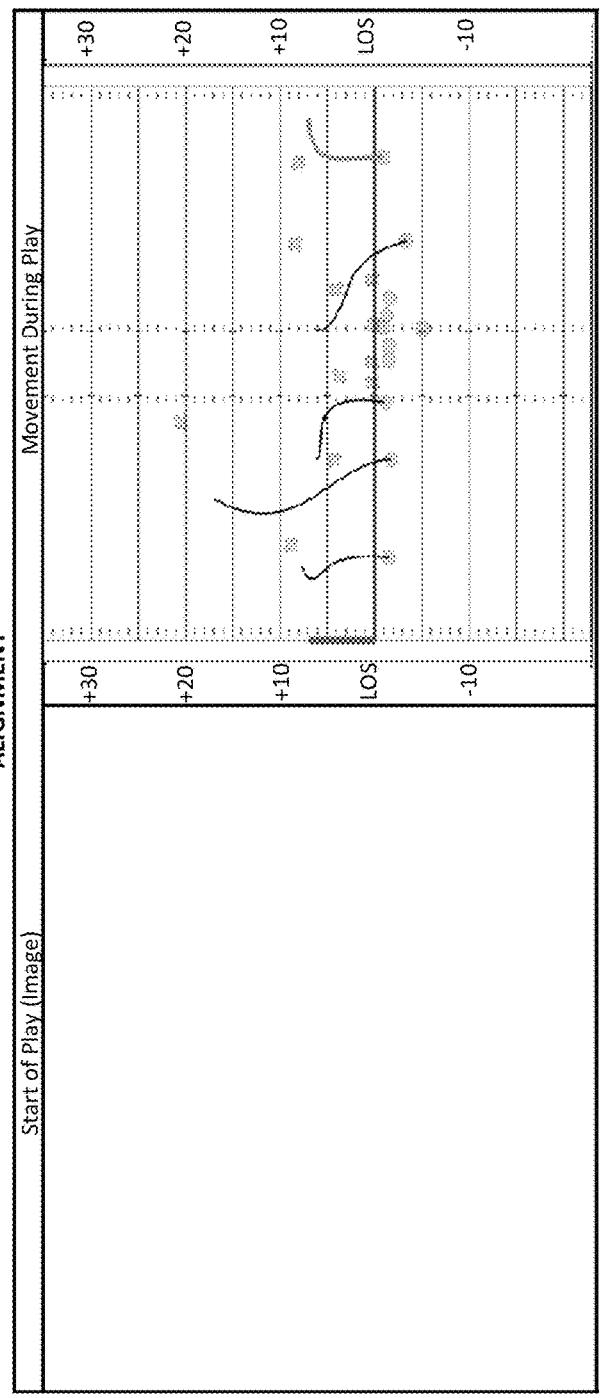
FIG. 29A
Continued on next page.

GROUPING

| Offensive Grouping | Defensive Grouping |
|---|---|
| 1 RB, 1 TE, 3 WR | 3 DL, 3 LB, 5 DB |
| Number of plays with this grouping and total plays | Number of plays with this grouping and total plays |

HEAD TO HEAD - GROUPING

| # Plays | Net Yards | Ave. Gain | Long Gain | Short Gain | Game Ave | *+/- | TD | Tackle/Loss | Sack | INT |
|---|---|---|---|---|---|---|---|---|---|---|

Rush

| # of Plays | Net Yards | Ave. Gain | Long Gain | Short Gain | Game Ave | *+/- | TD | Tackle/Loss |
|---|---|---|---|---|---|---|---|---|

Pass

| # of Plays | Net Yards | Ave. Gain | Long Gain | Short Gain | Game Ave | *+/- | TD | Sack | INT |
|---|---|---|---|---|---|---|---|---|---|

PARTICIPATION

| Offense | | | | Defense | | | |
|---|---|---|---|---|---|---|---|
| # | Name | Distance | Max Speed Play #/Total | # | Name | Distance | Max Speed Play #/Total |
| 1 | | | | 1 | | | |
| 2 | | | | 2 | | | |
| 3 | | | | 3 | | | |
| 4 | | | | 4 | | | |
| 5 | | | | 5 | | | |
| 6 | | | | 6 | | | |
| 7 | | | | 7 | | | |
| 8 | | | | 8 | | | |
| 9 | | | | 9 | | | |
| 10 | | | | 10 | | | |
| 11 | | | | 11 | | | |

FIG. 29B

PLAY

| Offense | Defense |
|---|---|
| Name of Play | Name of Play |

RESULT - OFFENSE

| | | | Yards before contact | Yards after contact | Direction | Gap Size | Peak Speed | Fumble | |
|---|---|---|---|---|---|---|---|---|---|
| Rush | # | Name | | | | | | | |
| Pass | # | Name | Shotgun or Under Center | Drop | Release | Complete | Yards @ Catch | Peak Speed | Fumble |
| Receiver | # | Name | Lined Up | Route | Yards @ Catch | Peak Speed | Fumble | | |
| Kick | | | | | | | | | |
| Punt | | | | | | | | | |

RESULT - DEFENSE

| | | | | | Distance @ Hand Off | Time Hand Off - Tackle |
|---|---|---|---|---|---|---|
| Tackle | # | Name | Yards Run | Peak Speed | | |
| Sack | # | Name | Yards Run | Peak Speed | | |
| INT | # | Name | Yards Run | Peak Speed | | |

ALIGNMENT

| START OF PLAY | MOVEMENT DURING PLAY |
|---|---|
| | |

GROUPING

| OFFENSE | DEFENSE |
|---|---|
| Players by position | Players by position |

PARTICIPATION

| OFFENSE | | | | | DEFENSE | | | | |
|---|---|---|---|---|---|---|---|---|---|
| # | Name | Distance | Max Speed | Ave Speed | # | Name | Distance | Max Speed | Ave Speed |
| 1 | | | | | 1 | | | | |
| 2 | | | | | 2 | | | | |
| 3 | | | | | 3 | | | | |
| 4 | | | | | 4 | | | | |
| 5 | | | | | 5 | | | | |
| 6 | | | | | 6 | | | | |
| 7 | | | | | 7 | | | | |
| 8 | | | | | 8 | | | | |
| 9 | | | | | 9 | | | | |
| 10 | | | | | 10 | | | | |
| 11 | | | | | 11 | | | | |

FIG. 30

Grouping Summary - Game

| Play Type | All | Pass | Rush | Kick Off | Kick Return | Punt | Punt Return | Field Goal |
|---|---|---|---|---|---|---|---|---|
| Down | All | 1st | 2nd | 3rd | 4th | | | |
| Quarter | All | Q1 | Q2 | Q3 | Q4 | OT1 | OT2 | OT3 | OT4 | OT5 |

Team 1
Offense

| Personnel | Plays/Total Net Yards Ave/Play |
|---|---|
| 1 RB, 1 TE, 3 WR | |
| 2 RB, 1 TE, 2 WR | |
| 2 RB, 0 TE, 3 WR | |
| 1 RB, 0 TE, 4 WR | |
| 1 RB, 2 TE, 2 WR | |
| 0 RB, 1 TE, 4 WR | |
| 6 OL, 1 RB, 3 TE, 0 WR | |

Team 2
Defense

| Personnel | Plays/Total Net Yards Ave/Play |
|---|---|
| 3 DL, 3 LB, 5 DB | |
| 4 DL, 3 LB, 4 DB | |
| 3 DL, 4 LB, 4 DB | |
| 3 DL, 2 LB, 6 DB | |
| 6 DL, 3 LB, 2 DB | |
| 4 DL, 2 LB, 5 DB | |

Defense

| Personnel | Plays/Total Net Yards Ave/Play |
|---|---|
| 3 DL, 3 LB, 5 DB | |
| 4 DL, 3 LB, 4 DB | |
| 3 DL, 4 LB, 4 DB | |
| 3 DL, 2 LB, 6 DB | |
| 6 DL, 3 LB, 2 DB | |
| 4 DL, 2 LB, 5 DB | |

Offense

| Personnel | Plays/Total Net Yards Ave/Play |
|---|---|
| 1 RB, 1 TE, 3 WR | |
| 2 RB, 1 TE, 2 WR | |
| 2 RB, 0 TE, 3 WR | |
| 1 RB, 0 TE, 4 WR | |
| 1 RB, 2 TE, 2 WR | |
| 0 RB, 1 TE, 4 WR | |
| 6 OL, 1 RB, 3 TE, 0 WR | |

Kick Return

| Personnel | Plays/Total Net Yards Ave/Play |
|---|---|

Kick Off

| Personnel | Plays/Total Net Yards Ave/Play |
|---|---|

Kick Off

| Personnel | Plays/Total Net Yards Ave/Play |
|---|---|

Kick Return

| Personnel | Plays/Total Net Yards Ave/Play |
|---|---|

Punt Return

| Personnel | Plays/Total Net Yards Ave/Play |
|---|---|

Punt

| Personnel | Plays/Total Net Yards Ave/Play |
|---|---|

Punt

| Personnel | Plays/Total Net Yards Ave/Play |
|---|---|

Punt Return

| Personnel | Plays/Total Net Yards Ave/Play |
|---|---|

Field Goal

| Personnel | Plays/Total Net Yards Ave/Play |
|---|---|

Field Goal

| Personnel | Plays/Total Net Yards Ave/Play |
|---|---|

FIG. 31

Grouping Summary - Practice

Play Type    All    Pass    Rush    Kick Off    Kick Return    Punt    Punt Return    Field Goal Offense

| Personnel | Plays/Total Net Yards Ave/Play |
|---|---|
| 1 RB, 1 TE, 3 WR | |
| 2 RB, 1 TE, 2 WR | |
| 2 RB, 0 TE, 3 WR | |
| 1 RB, 0 TE, 4 WR | |
| 1 RB, 2 TE, 2 WR | |
| 0 RB, 1 TE, 4 WR | |
| 6 OL, 1 RB, 3 TE, 0 WR | |

Defense

| Personnel | Plays/Total Net Yards Ave/Play |
|---|---|
| 3 DL, 3 LB, 5 DB | |
| 4 DL, 3 LB, 4 DB | |
| 3 DL, 4 LB, 4 DB | |
| 3 DL, 2 LB, 6 DB | |
| 6 DL, 3 LB, 2 DB | |
| 4 DL, 2 LB, 5 DB | |

Kick Return

| Personnel | Plays/Total Net Yards Ave/Play |
|---|---|

Kick Off

| Personnel | Plays/Total Net Yards Ave/Play |
|---|---|

Punt Return

| Personnel | Plays/Total Net Yards Ave/Play |
|---|---|

Punt

| Personnel | Plays/Total Net Yards Ave/Play |
|---|---|

Field Goal

| Personnel | Plays/Total Net Yards Ave/Play |
|---|---|

FIG. 32

Activity Summary - Game

GAME with Marker App & QB Stat

| # | POS | PLAYER | PLAYS | | | | DISTANCE (Yards) | | | | TIME | | | | DISTANCE (Yards) | | | SPEED (MPH) | |
|---|---|---|---|---|---|---|---|---|---|---|---|---|---|---|---|---|---|---|---|
| | | | OFFENSE | DEFENSE | SPECIAL TEAMS | TOTAL | OFFENSE | DEFENSE | SPECIAL TEAMS | TOTAL | IDLE | JOG | SPRINT | TOTAL | IDLE | JOG | SPRINT | MAX SPEED | AVG SPEED |
| | | | # and % | # and % | # and % | # | # and % | # and % | # and % | # | # and % | # and % | # and % | # | # and % | # and % | # and % | # | # |

SORTS  TOTAL
QUARTER
HALF

FIG. 33

Activity Summary - Practice

PRACTICE - TOTAL

| # | POS | PLAYER | PLAYS | | | | | DISTANCE (Yards) | | | | | TIME | | | | DISTANCE (Yards) | | | | SPEED (MPH) | |
|---|---|---|---|---|---|---|---|---|---|---|---|---|---|---|---|---|---|---|---|---|---|---|
| | | | OFFENSE | DEFENSE | SPECIAL TEAMS | TOTAL | OFFENSE | DEFENSE | SPECIAL TEAMS | DRILLS | TOTAL | IDLE | JOG | SPRINT | IDLE | JOG | SPRINT | MAX SPEED | AVG SPEED |
| | | | # and % | # and % | # | | # and % | # and % | # | | | # and % | # and % | # and % | | | | | |

PRACTICE - PLAYS

| # | POS | PLAYER | PLAYS | | | | DISTANCE (Yards) | | | | TIME | | | DISTANCE (Yards) | | | SPEED (MPH) | |
|---|---|---|---|---|---|---|---|---|---|---|---|---|---|---|---|---|---|---|
| | | | OFFENSE | DEFENSE | SPECIAL TEAMS | TOTAL | OFFENSE | DEFENSE | SPECIAL TEAMS | TOTAL | IDLE | JOG | SPRINT | IDLE | JOG | SPRINT | MAX SPEED | AVG SPEED |
| | | | # and % | # and % | # | | # and % | # and % | # | | # and % | # and % | # and % | | | | | |

PRACTICE - BREAKOUTS

| # | POS | PLAYER | TIME | | | | DISTANCE (Yards) | | | | SPEED (MPH) | |
|---|---|---|---|---|---|---|---|---|---|---|---|---|
| | | | IDLE | JOG | SPRINT | TOTAL | IDLE | JOG | SPRINT | TOTAL | MAX SPEED | AVG SPEED |

SORTS
 TOTAL
 PLAYS
 BREAKOUTS

FIG. 34

PLAY SUMMARY (VIRGINIA TECH AT DUKE - OCTOBER 9, 2015)

| Play | Series | Qtr | Clock | Down | YL | P/R | Flag | Flag Type | FLAG ID |
|---|---|---|---|---|---|---|---|---|---|
| 36 | 2nd | 1 | 10:00 | 1st-10 | own 33 | Pass | N | N/A | N |

Description

Rahming 10 yd Pass from T. Sirk. Pass Complete.

PARTICIPATION

| Offense | | | | | Defense | | | | |
|---|---|---|---|---|---|---|---|---|---|
| # | Name | Distance | Max Speed | Burst | # | Name | Distance | Max Speed | Burst |
| 1 | SIRK, T. | | | | 1 | HALL, G. | | | |
| 2 | EDWARDS, E. | | | | 9 | SMITH, W. | | | |
| 2 | HUTZLER, C. | | | | 14 | WASHINGTON, D. | | | |
| 3 | RAHMING, T.J. | | | | 22 | CAREY, H. | | | |
| 5 | LLOYD, J. | | | | 55 | WATTS, G. | | | |
| 6 | PIERRE, N. | | | | 54 | SIMMS, P. | | | |
| 7 | FULLER, K. | | | | 50 | GRAHAM, B. | | | |
| 8 | YOUNG, A. | | | | 71 | BEST, J. | | | |
| 9 | McDUFFIE, J. | | | | 74 | WILLINGHAM, T. | | | |
| 10 | SMITH, R. | | | | 99 | BERRY, W. | | | |
| 11 | SAMPSON, S. | | | | 79 | THOMPSON, R. | | | |

Continued on next page.

FIG. 35A

| GROUPING | |
|---|---|
| Offensive Grouping | Defensive Grouping |
| 1 RB, 1 TE, 3 WR | 3 DL, 3 LB, 5 DB |
| Number of plays with this grouping and total plays | Number of plays with this grouping and total plays |

RESULT - OFFENSE

| | | | | | | | |
|---|---|---|---|---|---|---|---|
| Rush | Yards before Cor | Yards after contact | Direction | Gap Size | Yards Run | Peak Speed Gain/loss | TD Fumble |
| Pass | Shotgun or Under | Drop | Release | Complete | Yards @ catch Yards Run | Peak Speed Gain/loss | TD Fumble |
| Receiver | Lined Up | Route | Yards @ Catch | Yards A | Yards Run | Peak Speed Gain/loss | TD Fumble |
| Kick | | | | | | | |
| Punt | | | | | | | |

HEAD TO HEAD - GROUPING

| # Plays | Net Yards | Ave. Gain | Long Gain | Short Gain | Game Ave | *+/- | TD | Tackle/Loss | Sack | INT |
|---|---|---|---|---|---|---|---|---|---|---|

FIG. 35C

| Company | Form | Description | Use |
|---|---|---|---|
| DVSport | Software | Sports - Football, hockey, basketball and lacrosse. Also provide replay systems (officials, medical and sideline). | Football coaching software that allows coaching staff to analyze video from games and practices. No time-code. |
| XOS | Software | Sports - Football, hockey, basketball and others. Also provide recruiting and officiating solutions. | Football coaching software that allows coaching staff to analyze video from games and practices. No time-code. |

FIG. 36

| Company | Form | Description | Use |
|---|---|---|---|
| Zephyr | Hardware and analytical software | Wearable GPS device tracks movements and some biometrics. Software analysis activity and produces reports on distance, speed, load, etc. Not real-time and does not work indoors. | Trainers and strenght coaches utilize the software to track performance, fitness and fatigue. |
| Catapult | Hardware and analytical software | Wearable GPS device tracks movements and some biometrics. Software analysis activity and produces reports on distance, speed, load, etc. Not real-time and does not work indoors. | Trainers and strenght coaches utilize the software to track performance, fitness and fatigue. |
| STATSports | Hardware and analytical software | Wearable GPS device tracks movements and some biometrics. Software analysis activity and produces reports on distance, speed, load, etc. Not real-time and does not work indoors. | Trainers and strenght coaches utilize the software to track performance, fitness and fatigue. |

FIG. 37

SYSTEMS AND METHODS FOR INTEGRATED AUTOMATED SPORTS DATA COLLECTION AND ANALYTICS PLATFORM

CROSS-REFERENCES TO RELATED APPLICATIONS

The present invention is related to and claims priority from the following U.S. patent documents. This application is a continuation of U.S. application Ser. No. 16/148,451 filed Oct. 1, 2018, which is a continuation-in-part of U.S. application Ser. No. 15/450,191 filed Mar. 6, 2017, which claims priority from U.S. Provisional Patent Application No. 62/305,219, filed Mar. 8, 2016. U.S. application Ser. No. 16/148,451 also claims priority from U.S. Provisional Patent Application No. 62/624,534, filed Jan. 31, 2018. All of the above-mentioned documents are incorporated herein by reference in their entirety.

BACKGROUND OF THE INVENTION

1. Field of the Invention

The present invention is directed to systems and methods for sports data collection, analytics, and applications thereof over a distributed network and a multiplicity of remote users having access to a data and analytics platform.

2. Description of the Prior Art

Traditionally, statistical information of a sports event, is generally collected manually by watching the event or event footage and entered into a database. The collected data is limited to what may be ascertained from viewing the event, and therefore the statistical data and visualizations based thereon are also limited. Similar to statistical information, event injury notification is limited to a participant raising an issue, which may not occur in highly competitive sporting events or by a person viewing the event indicating that an injury may have occurred. The medical staff may need to watch several minutes of event footage to view the injury event and are limited to what cameras may have captured at that time. Traditional video recording techniques have certain limitations, such as insufficient viewing angles, moving camera angles and zooms, non-calibrated images, and absence of tagged objects.

Recent advances in object tracking tools and various wearable monitoring devices have spawned the need for novel quantitative and timely data analysis tools that are customizable and equipped to provide easy to understand results and intelligent information.

By way of example the following are relevant prior art documents relating to sports data inputs, collection, analytics and application:

U.S. Pat. No. 8,989,880 for "Performance analytics based on real-time data for proximity and movement of objects" by inventor Michael A. Wohl et al., filed Jul. 15, 2013, describes Systems, methods, apparatuses, and computer readable media are disclosed for providing performance analytics using dynamics/kinetics models based on role data or weather data and real time data on movement and proximity of tagged objects. In one embodiment, a method is provided for monitoring a participant that at least includes correlating at least one tag to the participant; receiving blink data transmitted by the at least one tag; and determining tag location data based on the blink data. The method further includes receiving participant role data; comparing the tag location data to participant dynamics/kinetics models based at least in part on the participant role data; and determining participant location data based on the comparing the tag location data to the participant dynamics/kinetics models.

U.S. Pat. No. 9,014,830 for "Method, apparatus, and computer program product for combined tag and sensor based performance modeling using real-time data for proximity and movement of objects" by inventor Michael A. Wohl et al., filed Jul. 15, 2013, describes systems, methods, apparatuses, and computer readable media for providing performance modeling by combining tags and sensors providing real time data on movement and proximity of tagged objects. In one embodiment, a method is provided for monitoring a participant that at least includes correlating at least one tag to the participant; receiving blink data transmitted by the at least one tag; determining tag location data based on the blink data; correlating a sensor to the participant; and receiving sensor derived data. The method further includes receiving participant role data; comparing the tag location data to participant dynamics/kinetics models based at least in part on the participant role data; and determining the participant location data based on comparing the tag location data and the sensor derived data to the participant dynamics/kinetics models.

U.S. Pat. No. 9,180,357 for "Multiple antenna interference rejection in ultra-wideband real time locating systems" by inventor Edward A. Richley, filed Jul. 15, 2013, describes Systems, methods, apparatuses, and computer readable media are disclosed for providing interference rejection in ultra-wideband real time locating systems. In one embodiment, an ultra-wideband (UWB) receiver is configured to: receive an interference signal from a source positioned outside a monitored region; receive a composite signal transmitted from a tagged object moving about a playing field within the monitored region, wherein the composite signal comprises a location signal and a component of the interference signal; detect whether the component of the interference signal exceeds a threshold value; and adjust, via a processor, filtering of the composite signal to attenuate the component of the interference signal based on whether the component of the interference signal exceeds the threshold value. Some embodiments provide for filtering of the composite signal using a combiner while others employ a tunable notch filter. Corresponding systems, methods, and computer-readable storage medium are also provided.

U.S. Publication No. 2015/0148129 for "METHOD, APPARATUS, AND COMPUTER PROGRAM PRODUCT FOR PERFORMANCE ANALYTICS DETERMINING PARTICIPANT STATISTICAL DATA AND GAME STATUS DATA" by inventor David Austerlade et al., filed Dec. 1, 2014, describes Systems, methods, apparatuses, and computer program products for providing analytics including participant statistical data or game status data. In one embodiment, a method is provided for transmitting participant data relating to one or more participants that are available in a fantasy game, the fantasy game is at least partially related to a players performance in a sporting event; receiving a selected participant data indication from at least one user, the selected participant data indication provides selection of at least one participant from the participant data; generating a participant data update for one or more participants based on the selected participant data indication; the participant data is defined by a time period comprising an event and is calculated based on blink data transmitted from a location tag mounted to the participant; and transmitting the participant data update, the participant data update is viewable via a user interface.

U.S. Publication No. 2015/0149837 for "METHOD, APPARATUS, AND COMPUTER PROGRAM PRODUCT FOR COLLECTING AND DISPLAYING SPORTING EVENT DATA BASED ON REAL TIME DATA FOR PROXIMITY AND MOVEMENT OF OBJECTS" by inventor Rodrigo Alonso et al., filed Oct. 24, 2014, describes a method, apparatus and computer program product for collecting sporting event data based on real time data for proximity and movement of objects. In the context of a method, the method includes calculating a tag data filter parameter for a plurality of tag events based on received tag blink data and tag location data, wherein the tag data filter parameter comprises a blink period, distance span, or velocity, calculating a participant location data adjustment factor based on the tag data filter parameter, and calculating multidimensional player location information per unit time based on the plurality of tag events and the participant location adjustment factor.

U.S. Publication No. 2015/0356332 for "SYSTEMS, APPARATUS AND METHODS FOR VARIABLE RATE ULTRA-WIDEBAND COMMUNICATIONS" by inventor Belinda Turner et al., filed Jun. 4, 2015, describes systems, methods, apparatuses, and computer readable media for providing variable blink rate ultra-wideband (UWB) communications. Some embodiments may provide for a radio frequency (RF) tag including a motion sensor, processing circuitry, and a UWB transmitter. The motion sensor may be configured to generate one or more motion data values indicating motion of the RF tag. The UWB transmitter may be configured to transmit blink data at variable blink rates. The processing circuitry may be configured to receive the one or more motion data values from the motion sensor, determine a blink rate for the UWB transmitter based on the one or more motion data values, and control the UWB transmitter to wirelessly transmit the blink data at the blink rate. In some embodiments, the RF tag may include a UWB receiver and the blink rate may be controlled remotely by a system.

U.S. Publication No. 2015/0375083 for "Method, Apparatus, And Computer Program Product for Enhancement of Event Visualizations Based on Location Data" by inventor Jill Stelfox et al., filed Jun. 5, 2015, describes methods, apparatuses, and computer program products directed to generating event visualizations based on location data. In one example, a method for providing enhanced event visualizations based on location data is provided which includes receiving, by a visualizations processor, play diagram data from a play model database and receiving location data during a play period for a plurality of participants. The method further includes determining a selected play based on comparing the location data to the play diagram data and determining an actual route for one or more participants of the plurality of participants based on the location data. The method further includes generating, by the visualization processor, an accuracy visualization interface by comparing the actual route for each of the one or more participants to the selected play.

U.S. Publication No. 2015/0097700 for "TEAM PERFORMANCE MONITORING" by inventor Shaun Holthouse, filed Oct. 4, 2013, describes a system for monitoring a plurality of individuals engaged in a sporting activity. The system includes a base station; a plurality of individual participant monitors, affixed to each individual and wirelessly communicating with said base station; a plurality of sensors in each said monitor or on each individual, in communication with each monitor and configured to sense a physiological or activity parameter of the individual; each monitor transmitting data relating to parameters sensed by said sensors to the base station; one or more group monitoring devices communicating wirelessly with said base station to receive said sensed parameter data. The system displays, during said activity, data relating to one or more sports parameters of one or more individuals as well as displaying the operational status of one or more of each monitor, each sensor, and the base station.

U.S. Pat. No. 8,466,794 for "Head impact event reporting system" by inventor Christoph Mack et al., filed Jan. 19, 2011, describes Head impact event evaluation systems and methods. A system and computer implemented method for event detection includes collecting sensor data transmitted from one or more sensor devices being attached to one or more users. The sensors transmit data when an event results in sensor data above a threshold value. At least one force is determined based on the collected sensor data. At least one force vector is determined based on a location of one or more sensors associated with the sensor devices and the determined at least one of the linear or rotational force. At least a portion of a human form is displayed with the determined force vector based on the determined at least on force vector on a display.

U.S. Pat. No. 8,079,247 for "Impact detection system" by inventor Brian Keith Russell et al., filed Jun. 12, 2008, describes an impact detection system providing a means of sensing, monitoring and recording impact events on an impact surface using at least one sensor that is incorporated into the impact surface. The sensor(s) can be integral with, attached to or located behind various types of impact surface including various types of garments that can be worn by an individual or on composite materials such as an aircraft fuselage for example. The impact detection system includes a portable impact detection device electrically connected to the sensor(s) and is used to detect ballistic or non-ballistic type impacts on the impact surface. The portable impact detection device processes the impact data detected by the sensor(s) and stores the data for analysis at a later time or outputs the data to a third party system for review and/or analysis.

U.S. Pat. No. 8,400,302 for "Electric field sensing device" by inventor Brian Keith Russell et al., filed Jun. 10, 2010, describes a sensing system that uses at least one conductive plate and associated electronic circuitry to provide an output that is indicative of an object's position in relation to the at least one conductive plate. The sensing system is provided with a high impedance drive signal that varies as a result of the location of an object relative to the at least one conductive plate. The electronic circuitry receives a high impedance drive signal value as an input and a processor uses the value to calculate a digital output indicative of the object's position. The high impedance drive signal value is monitored over time enabling the objects position, displacement, pressure, movement, impact and energy to be determined. This data is output to a display and may also be transmitted to a person located remotely from the object being monitored.

U.S. Pat. No. 9,220,444 for "System method and device for determining the risk of dehydration" by inventor Brian Russell, filed Jun. 6, 2011, describes a system, device and method of determining the probability of dehydration of a person. In one embodiment, the method comprises receiving data of a heart rate of the person; receiving data of a posture of the person; determining that a first posture of the person satisfies first posture criteria for a first predetermined time period; determining a first heart rate for the person during the first predetermined time period; subsequent to determining that the first posture of the person satisfies first posture criteria for a first predetermined time period, determining that a second posture of the person satisfies second posture criteria for at least a second predetermined period; determining a second heart rate for the person during the second predetermined time period; determining a change in heart rate as the second heart rate minus the first average heart rate; determining a first probability of dehydration based, at least in part, on the change in heart rate; and outputting the first probability of dehydration.

U.S. Pat. No. 8,860,570 for "Portable wireless personal head impact reporting system" by inventor Biju Thomas et al., filed Feb. 3, 2012, describes a system for sensing, analyzing and reporting a collision event experienced by a person or object sensor module designed to a person or object, module angular velocities over time and a processor for analyzing the sensed velocities, calculating properties of angular velocities, such as jerk and jolt, comparing these properties with threshold values selected to correlate to predicted severities of injury to the person or object, transmitting information regarding these properties to communication device user-designated persons. Also provided are group tracking and communication devices for use by monitors to manage multiple persons equipped with sensor modules. The sensor modules and group tracking and communication devices are designed to be portable, attachable and detachable so that they can be attached to different types of gear used by persons engaging in different activities.

U.S. Publication No. 2015/0306486 for "Method to Prevent Harm to Athletes from Overexertion" by inventor Robert J. Logan et al., filed Jul. 8, 2015, describes methods to prevent harm to athletes from overexertion. The method includes inserting a dental appliance into a mouth of each monitored athlete, the dental appliance having sensors for monitoring parameters such as body temperature and hydration level of the athlete; obtaining at a monitoring station wireless transmissions of current measurements from each of the dental appliances; storing measurements along with a source of the measurements and a time associated with the measurements; and providing a notification when a monitored athlete is in danger from overexertion as indicated by a trend in the stored measurements.

U.S. Pat. No. 8,289,185 for "Sports telemetry system for collecting performance metrics and data" by inventor Ramon A. Alonso, filed May 3, 2010, describes systems and methods for collecting sports data. The systems and methods include measuring, at one or more sensor modules mounted, affixed, or embedded on at least one sports participant, data corresponding to identification, movement, position, or condition of the at least one sports participant; broadcasting, from one or more telemetry modules mounted, affixed, or embedded on the at least one sports participant, signals carrying the data corresponding to identification, movement, position, or condition of the at least one sports participant; measuring, at one or more sensor modules mounted, affixed, or embedded in a sports object, data corresponding to identification, movement, position, or condition of the sports object; and broadcasting, from one or more telemetry modules mounted, affixed, or embedded on the sports object, signals carrying the data corresponding to identification, movement, position, or condition of the sports object. The systems and methods also include receiving the signals from the telemetry modules mounted, affixed, or embedded on the at least one sports participant and the telemetry modules mounted, affixed, or embedded on the sports object; and processing the received signals to calculate position information or movement information of a sports object or a sports participant in relation to a playing surface of a sports event.

U.S. Pat. No. 9,035,776 for "Wireless monitoring of safety helmets" by inventor Robert R. Miller, filed Jan. 20, 2011, describes a system and method for remote monitoring of a subject wearing a sports helmet. In one aspect, the system includes a safety helmet and a sensor integrated with the helmet for continuously gathering head acceleration force data, the head acceleration force data associated with the head movements of a subject. The system also includes a wireless transceiver coupled to the sensor for transmitting the head acceleration force data and a mobile device for receiving the head acceleration force data from the wireless transceiver. The system further includes a database engine for displaying the head acceleration force data to a user.

U.S. Publication No. 2012/0139731 for "SYSTEM AND METHOD FOR WIRELESS MONITORING OF SPORTS ACTIVITIES" by inventor Leonid Razoumov et al., filed Dec. 1, 2010, describes a system and method for wireless monitoring of sports activities. A subject participating in a sports activity is associated with biometric sensors which measure the subject's body movements. In one aspect, the system includes a sensor for continuously gathering biometric data from a subject performing a sports activity where the biometric data associated with the body movements of the subject. A wireless transceiver coupled to the sensor transmits the biometric data and a database engine receives the biometric data from the wireless transceiver and providing real-time feedback. The real-time feedback associated with the biometric data from the subject is characterized by instructions associated with the sports activity.

U.S. Pat. No. 7,552,031 for "Personal items network, and associated methods" by inventor Curtis A. Vock et al., filed Dec. 28, 2006, describes a personal items network, including several items, each item having a wireless communications port for coupling in network with every other item is provided. Each item has a processor for determining if any other item in the network is no longer linked to the item, and an indicator for informing a user that an item has left the network, wherein a user may locate lost items. A method for locating lost personal items is also provided. The method includes linking at least two personal items together on a network, and depositing one or both of time and location information in an unlost item when one of the items is lost out of network.

U.S. Pat. No. 7,627,451 for "Movement and event systems and associated methods" by inventor Curtis A. Vock et al., filed May 10, 2007, describes a smart sensor in the form of an adhesive bandage. The sensor sticks to people and objects and wirelessly communicates with remote receivers. Internal detectors sense conditions associated with movement or the environment of the sensor. Typically, sensors of the invention communicate by an RF transmitter or transceiver. Groups of sensors may be combined within a common canister that imparts date and time information and "power on" when dispensed.

U.S. Pat. No. 8,482,612 for "System and method for location tracking" by inventor Michael Tamir et al., filed Jul. 26, 2010, describes a system for embedment within a sport playing object, a ball for example. The system is associated with continuous determination of a state of the object, its location and pose. The system includes an inertial navigation system (INS) module first state module adapted for measuring parameters associated with the object state, a wireless transmitter, a battery for providing electric power, and a mounting module connecting the object with the first state module, the wireless transmitter and the battery. Independent data relating to the object state is provided by a second state module, a camera system for example. The object state is calculated in accordance with the parameters measured by the first state module and in accordance with the independent provided data. The camera system capturing the object includes at least two mutually displaced camera clusters, and each camera cluster includes one or more cameras for providing a predetermined spatial resolution. The system may include a global positioning system (GPS) module which provides the independent data relating to the object state.

U.S. Pat. No. 9,058,670 for "Trajectory detection and analysis in sporting events" by inventor Michael Birenboim et al., filed May 2, 2011, describes a method for conveying data on a flying object in a scene. The method including capturing video frames of the scene by video cameras to get video frames which include image of the object, identifying the object in captured video frames to get associated object parameters, calculating motion variables, solving motion equations for anticipated object trajectory taking into account certain effects, and conveying data to displaying devices. The certain effects are an effect of object collision with a ground surface, air friction, wind effect, and interaction of a spinning object with air. The method may be applied to a ball in a sporting playing field. The cameras may have variable operating parameters desirable for the calculating the motion variables, which may be determined by camera calibration using captured artifacts of the scene. Shadow of the object may be captured as well and be used to provide data absent due to occluding the object from a video camera. Also, the captured frames of a ball may be used to calculate parameters relating to a bat which hits the ball.

U.S. Publication No. 2008/0192116 for "Real-Time Objects Tracking and Motion Capture in Sports Events" by inventor Michael Tamir et al., filed Sep. 19, 2007, describes non-intrusive peripheral systems and methods to track, identify various acting entities and capture the full motion of these entities in a sports event. The entities preferably include players belonging to teams. The motion capture of more than one player is implemented in real-time with image processing methods. Captured player body organ or joints location data can be used to generate a three-dimensional display of the real sporting event using computer games graphics.

U.S. Publication No. 2015/0131845 for "METHODS, SYSTEMS AND SOFTWARE PROGRAMS FOR ENHANCED SPORTS ANALYTICS AND APPLICATIONS" by inventor Arian S. Forouhar et al., filed Nov. 4, 2014, describes a system for enhanced sports analytics and/or content creation. The system includes: an object tracking system that generates coordinate data corresponding to object motion in a sports event; a data processing module that receives the coordinate data from the object tracking system, analyzes the coordinate data with an event recognition algorithm that identifies and characterizes events and outcomes of interest, and catalogs the data in accordance with the identified events and outcomes into event profile data; a database that receives and stores the event profile data generated by the data processing module; a user application that accesses the event profile data from the database; and at least one processing unit that executes instructions stored in at least one non-transitory medium to implement at least one of the object tracking system, the data processing module, or the user application.

U.S. Pat. No. 9,044,198 for "Enhancement of the presentation of an athletic event" by inventor Edward C. Benzel et al., filed Jul. 15, 2011, describes systems and methods for enhancing a presentation of an athletic event. Data is received at a sensor located at a first location on a first athlete. The data represents an impact applied to the first athlete by a second athlete. One of an acceleration and a force at a second location on the first athlete induced by the impact is determined. A representation of the determined one of the acceleration and the force at the second location on the first athlete is displayed to an audience of the athletic event.

U.S. Pat. No. 9,076,041 for "Motion event recognition and video synchronization system and method" by inventor Michael Bentley et al., filed Apr. 21, 2014, describes a system and method enabling recognition of events within motion data obtained from portable wireless motion capture elements and video synchronization of the events with video as the events occur or at a later time, based on location and/or time of the event or both. The system and method May use integrated camera or external cameras with respect to mobile device to automatically generate generally smaller event videos of the event on the mobile device or server. The system and method also enables analysis or comparison of movement associated with the same user, other user, historical user or group of users. The system and method provides low memory and power utilization and greatly reduces storage for video data that corresponds to events such as a shot, move or swing of a player, a concussion of a player, or other medical related events or events, such as the first steps of a child, or falling events.

U.S. Pat. No. 9,235,765 for "Video and motion event integration system" by inventor Michael Bentley et al., filed Nov. 20, 2014, describes a system enabling intelligent synchronization and transfer of generally concise event videos synchronized with motion data from motion capture sensor(s) coupled with a user or piece of equipment. The system greatly saves storage and increases upload speed by uploading event videos and avoiding upload of non-pertinent portions of large videos. The system provides intelligent selection of multiple videos from multiple cameras covering an event at a given time, for example selecting one with least shake. Enables near real-time alteration of camera parameters during an event determined by the motion capture sensor, and alteration of playback parameters and special effects for synchronized event videos. The system creates highlight reels filtered by metrics and can sort by metric. The system integrates with multiple sensors to save event data even if other sensors do not detect the event. The system also enables analysis or comparison of movement associated with the same user, other user, historical user or group of users.

U.S. Pat. No. 9,247,212 for "Intelligent motion capture element" by inventor Bhaskar Bose et al., filed Jan. 17, 2013, describes an intelligent motion capture element that includes sensor personalities that optimize the sensor for specific movements and/or pieces of equipment and/or clothing and may be retrofitted onto existing equipment or interchanged therebetween and automatically detected for example to switch personalities. The intelligent motion capture element may be used for low power applications and accurate data capture for use in healthcare compliance, sporting, gaming, military, virtual reality, industrial, retail loss tracking, security, baby and elderly monitoring and other applications for example obtained from a motion capture element and relayed to a database via a mobile phone. System obtains data from motion capture elements, analyzes data and stores data in database for use in these applications and/or data mining; enables unique displays associated with the user, such as 3D overlays onto images of the user to visually depict the captured motion data; and enables performance related equipment fitting and purchase. Includes active and passive identifier capabilities.

U.S. Publication No. 2003/0182620 for "Synchronization of video and data" by inventor James Errico et al., filed May 22, 2002, describes a system including a video stream and a data stream. The system synchronizes the data stream to different portions of the video stream.

U.S. Publication No. 2009/0210395 for "Methods, systems, and computer readable media for dynamically searching and presenting factually tagged media clips" by inventor Marc C. Sedam, filed Feb. 12, 2009, describes methods, systems, and computer readable media for dynamically searching and presenting factually tagged media clips. According to one aspect, a method for providing dynamic user access to factually tagged media portions of a media presentation is provided. The method includes dividing a media presentation into media portions and factually tagging the media portions. The factually tagged media portions are stored in a database and dynamic user access to the factually tagged media portions is provided. The user dynamically accesses, via a fantasy sports game interface, the tagged media portions stored in the database by engaging in a dialogue with at least one server associated with the database and retrieving portions of the media presentation in response to user queries.

U.S. Publication No. 2015/0208044 for "METHOD AND SYSTEM FOR PROCESSING A VIDEO RECORDING WITH SENSOR DATA" by inventor Quinn A. Jacobson et al., filed Jan. 21, 2015, describes a method for processing a video recording involving receiving sensor data from at least one sensor located on a person performing a physical activity. The sensor data includes biometric and/or biomechanical measurements taken from the person while performing the activity. The video recording is of the person performing the activity. The received video recording is correlated with the received sensor data to allow portions of the video recording to be matched with portions of the sensor data from corresponding periods of time. Correlation allows one to readily find and review video footage that show the activity being performed correctly or not based on an interpretation of the sensor data.

It would be beneficial for the newly available information to be accessible for various parties involved in a sports activity including players, coaches, owners, general managers, trainers, medical staff, broadcasters, viewers, fans, and others. An integrated automated sports data collection and analytics will improve playing performance, team strategy, broadcasting, and the overall consumer experience.

None of the prior art describes a cloud-based platform for collecting various data related to players and sports activities and providing meaningful statistics, analytics and intelligence.

SUMMARY OF THE INVENTION

The present invention is directed to systems and methods for data input, collection, and analytics for sports games. Different types of data, for example but not limited, location data, movement data, impact data and biometric data for individual players are collected via wearable sensors in real time during a sports game and transmitted to a cloud-based platform together with other sports data, including video, timing, scoring, statistics, and events with time code. The cloud-based platform is operable to aggregate, correlate, integrate, synchronize, and analyze various data related to the sports game; store, query and retrieve various live data and historical data in and from a proprietary database; and perform analytics and provide intelligence to different parties involved in a sports game, including coaches, trainers, medical staff, live announcers, broadcasters, displays, viewers, and fans and etc. These different parties are provided authorized licensed or subscription-based access via API to the cloud-based platform for tailored data feeds with real time push. In one embodiment, the present invention provides at least two data inputs are synchronized by time code for an integrated data that is searchable, i.e., query by time code, aggregate across data inputs by time code to synchronize with events that are rules-based for each sport or game.

These and other aspects of the present invention will become apparent to those skilled in the art after a reading of the following description of the preferred embodiment when considered with the drawings, as they support the claimed invention.

BRIEF DESCRIPTION OF THE DRAWINGS

FIG. 7 is a list of potential partners providing wearable clothing having biometric data capturing function.

FIG. 8 is a list of potential partners providing wearable bands having biometric data capturing function.

FIG. 9 is a list of potential partners providing wearable patches having biometric data capturing function.

FIG. 11 is a table comparing potential partners providing wearable and consumable products having biometric capturing function.

FIG. 12 is a list of potential partners providing head impact sensing systems.

FIG. 13 is a list of features of level 1 according to one embodiment of the present invention.

FIG. 14 is a list of events marked by a marking application program according to one embodiment of the present invention.

FIG. 15 is a list of features for a talent prompter at level 2 according to one embodiment of the present invention.

FIG. 16 is a list of features for a research prompter at level 2 according to one embodiment of the present invention.

Figure 17:
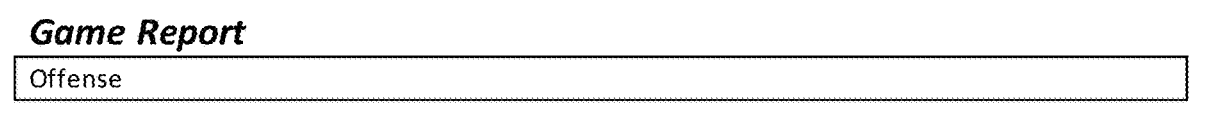

FIG. 17 is game report as a product of level 2 according to one embodiment of the present invention.

FIGS. 18A and 18B is a list of features for telestration and sports Character Generator (CG) for offense according to one embodiment of the present invention.

FIGS. 19A and 19B is a list of features for telestration and sports CG for defense according to one embodiment of the present invention.

FIG. 20 is a list of features for sports CG for participation according to one embodiment of the present invention.

FIGS. 21A and 21B illustrate how to use telestration and sports CG for offense in a broadcast according to one embodiment of the present invention.

FIG. 22 illustrates how to use telestration and sports CG for defense in a broadcast according to one embodiment of the present invention.

FIG. 23 illustrates how to use sports CG for participation in a broadcast according to one embodiment of the present invention.

FIG. 24 is a sample screenshot for a talent prompter screen.

FIGS. 25A and 25B is an offense summary template for game.

FIGS. 26A and 26B is an offense summary template for practice.

FIG. 27 is a defense summary template for game.

FIG. 28 is a defense summary template for practice.

FIGS. 29A and 29B is a play summary template for game.

FIG. 30 is a play summary template for practice.

FIG. 31 is a grouping summary template for game.

FIG. 32 is a grouping summary template for practice.

FIG. 33 is an activity summary template for game.

FIG. 34 is an activity summary template for practice.

FIGS. 35A and 35B and 35C is an example of play summary for game.

FIG. 36 is a list of potential partners at level 2 providing software for coaching.

FIG. 37 is a list of potential partners at level 2 providing software for training.

FIG. 82 is a screenshot displaying player No. 82 is below heart rate threshold with alert on.

DETAILED DESCRIPTION

The present invention proposes systems and method for sports data collection, analytics, and applications thereof over a distributed network and a multiplicity of remote users having access to a data and analytics platform. The proposed systems and methods are operable for integrating disparate and asynchronous sports data collection systems into a cohesive set of time-synchronized data; making such time-synchronized set of data available for live query, live access, and live push; facilitating the performance of multi-input analytics on the time-synchronized set of data; and facilitating the presentation of the time-synchronized set of data in a variety of real-time displays. Different types of data, for example but not limited to, location data, movement data, impact data and biometric data for individual players are collected via wearable sensors in real time during a sports game, practice, event, activity or training session, and are transmitted to a server-type platform together with other sports game, practice, event, activity or training session data, including video, timing, scoring, statistics, and events with time code. The server-type platform is operable to aggregate, correlate, organize and synchronize various data related to the sports game, practice, event, activity or training session; store, query and retrieve various live data and historical data in and from a proprietary database; provide a means for performing analytics on the collective set of data; and provide intelligence and displays to different parties involved or interested in a sports game, practice, event, activity, or training session, including, but not limited to, coaches, trainers, medical staff, live announcers, broadcasters, sports officials, displays, viewers, and fans and etc. These different parties may receive or subscribe to licensed access to the server-type platform to receive tailored data feeds through a variety of mechanisms including but not limited to API access, query access, and a real-time push mechanism.

Figure 1:
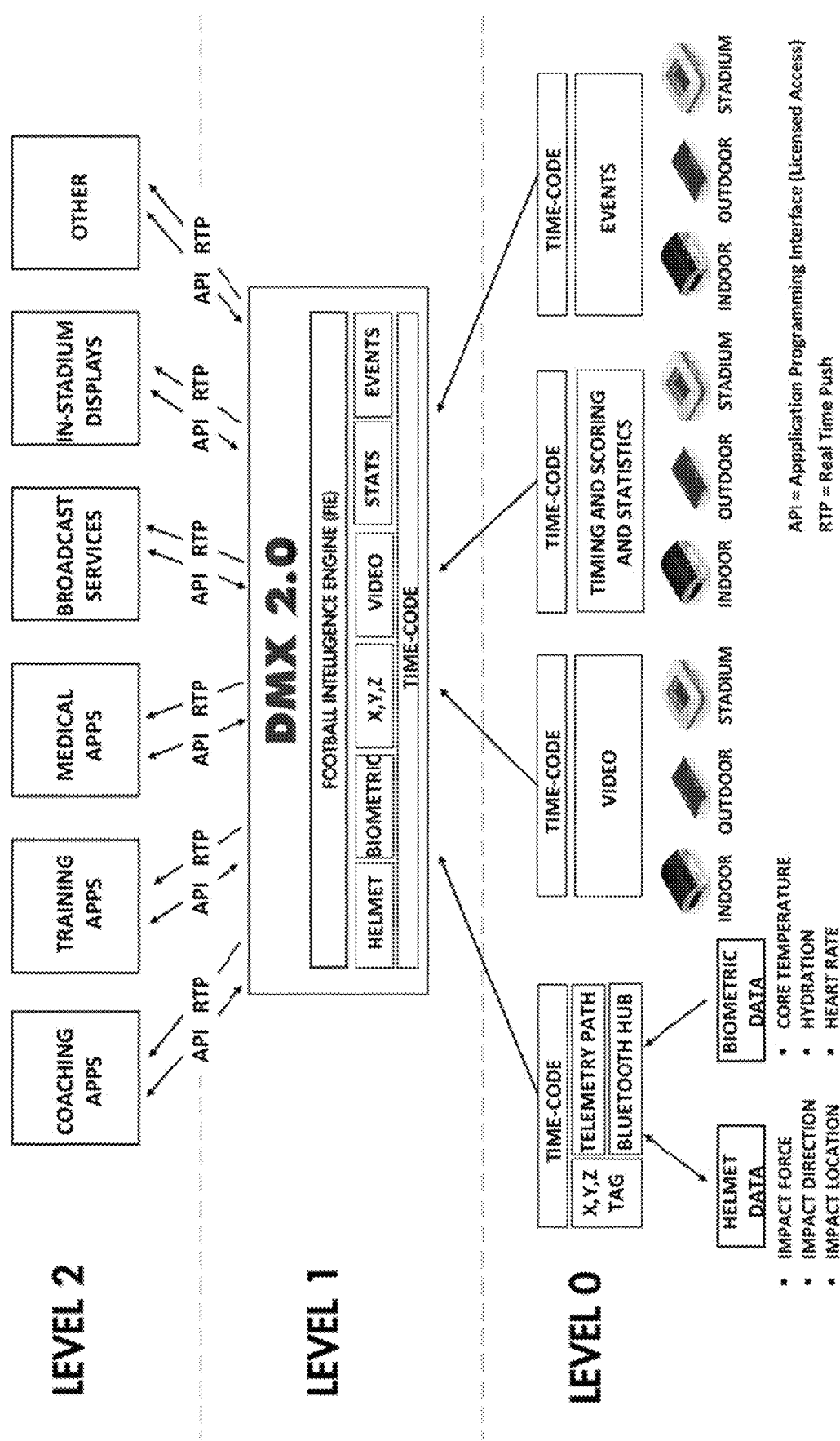
FIG. 1 an architecture diagram of an integral system for data collection and analytics for sports activities according to one embodiment of the present invention.
Figure 2:
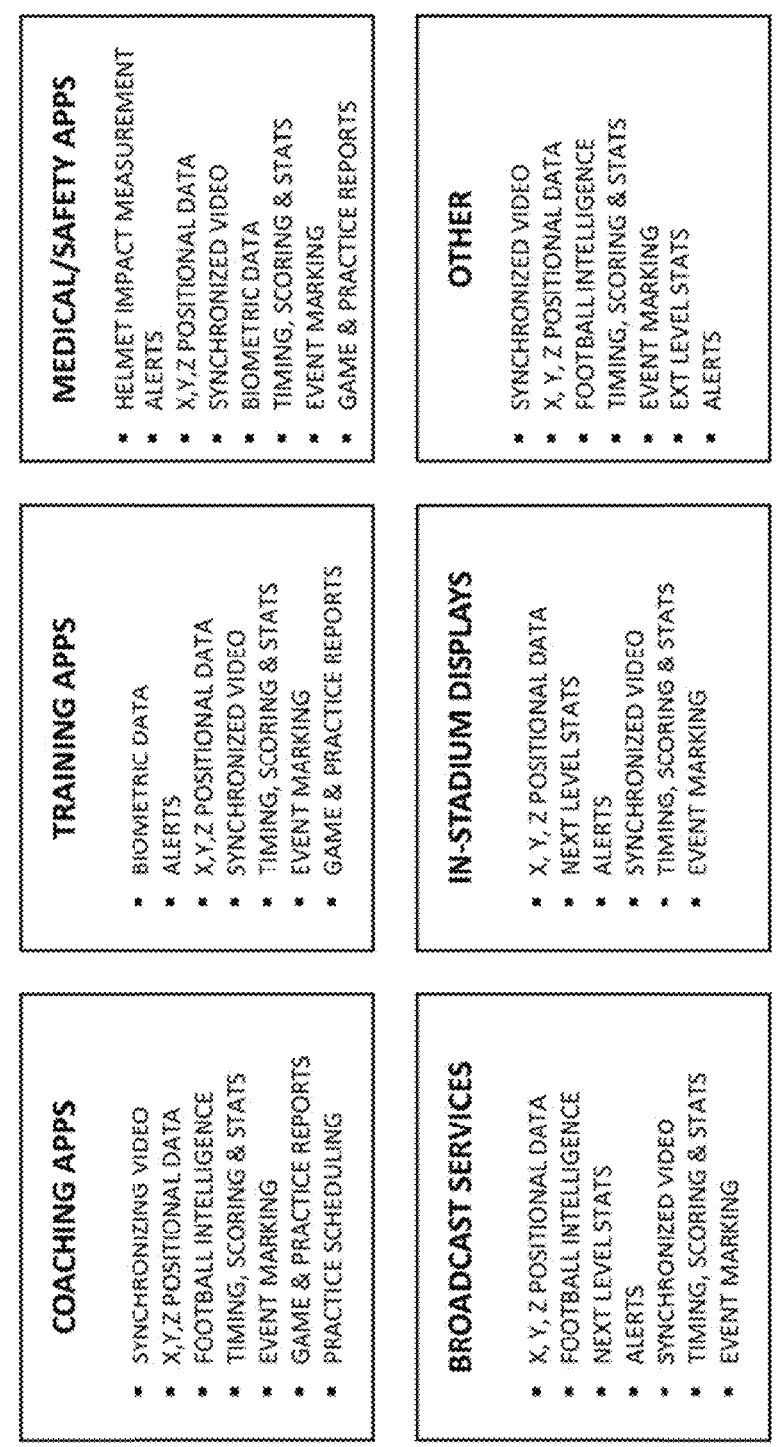
FIG. 2 is a detailed diagram of level 2 in FIG. 1.
Figure 3:
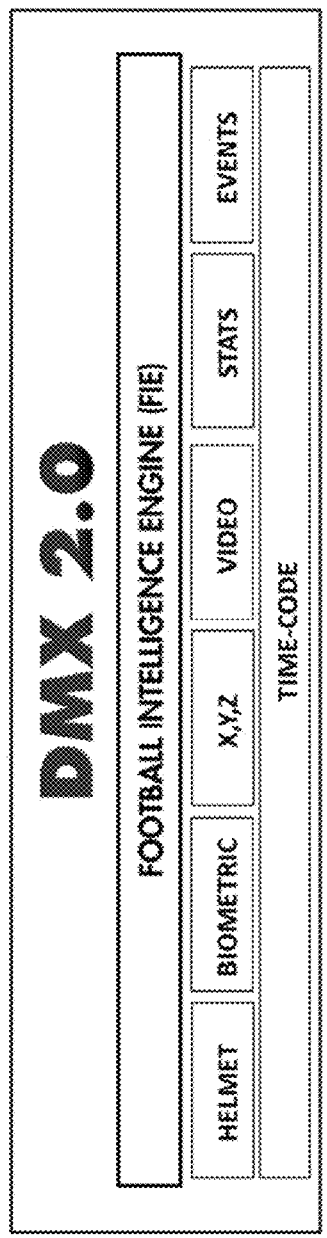
FIG. 3 is a separate diagram of level 1 in FIG. 1.
Figure 4:
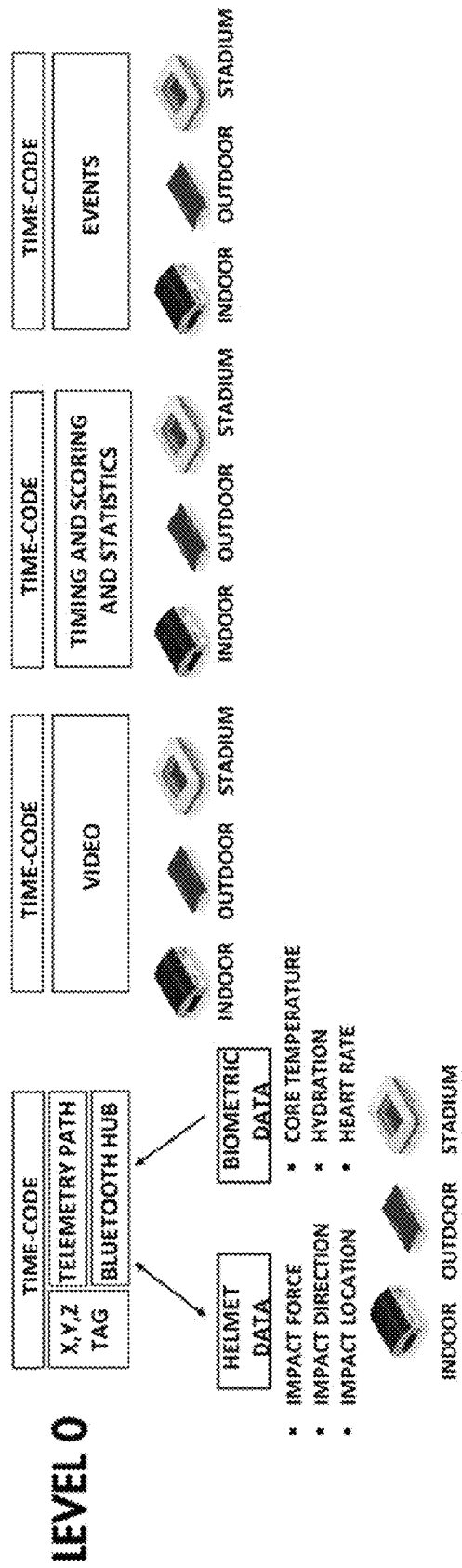
FIG. 4 is a separate diagram of level 0 in FIG. 1.
Figure 5:
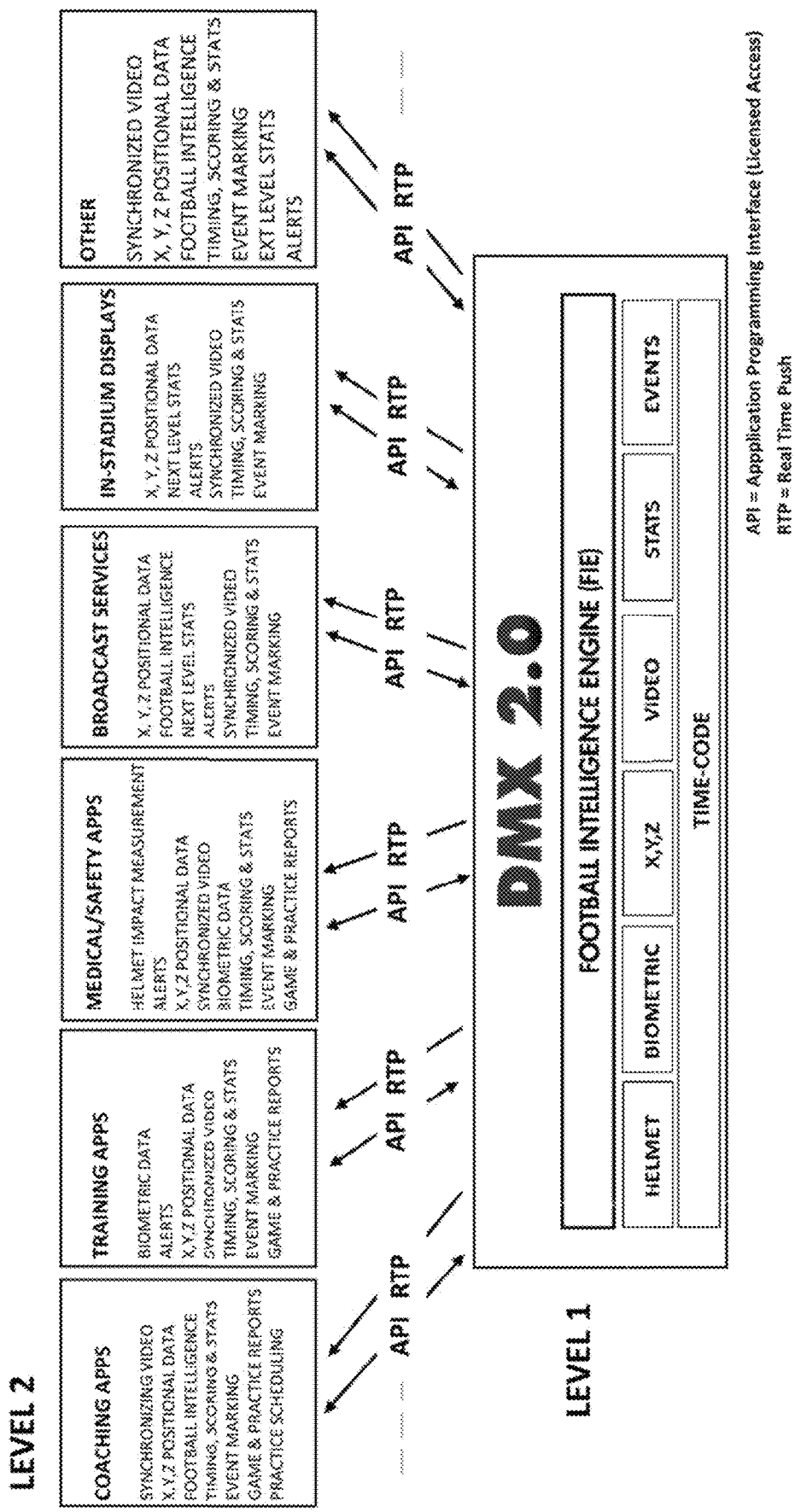
FIG. 5 is an illustration of the interactions between level 1 and level 2 in FIG. 1.
Figure 6:
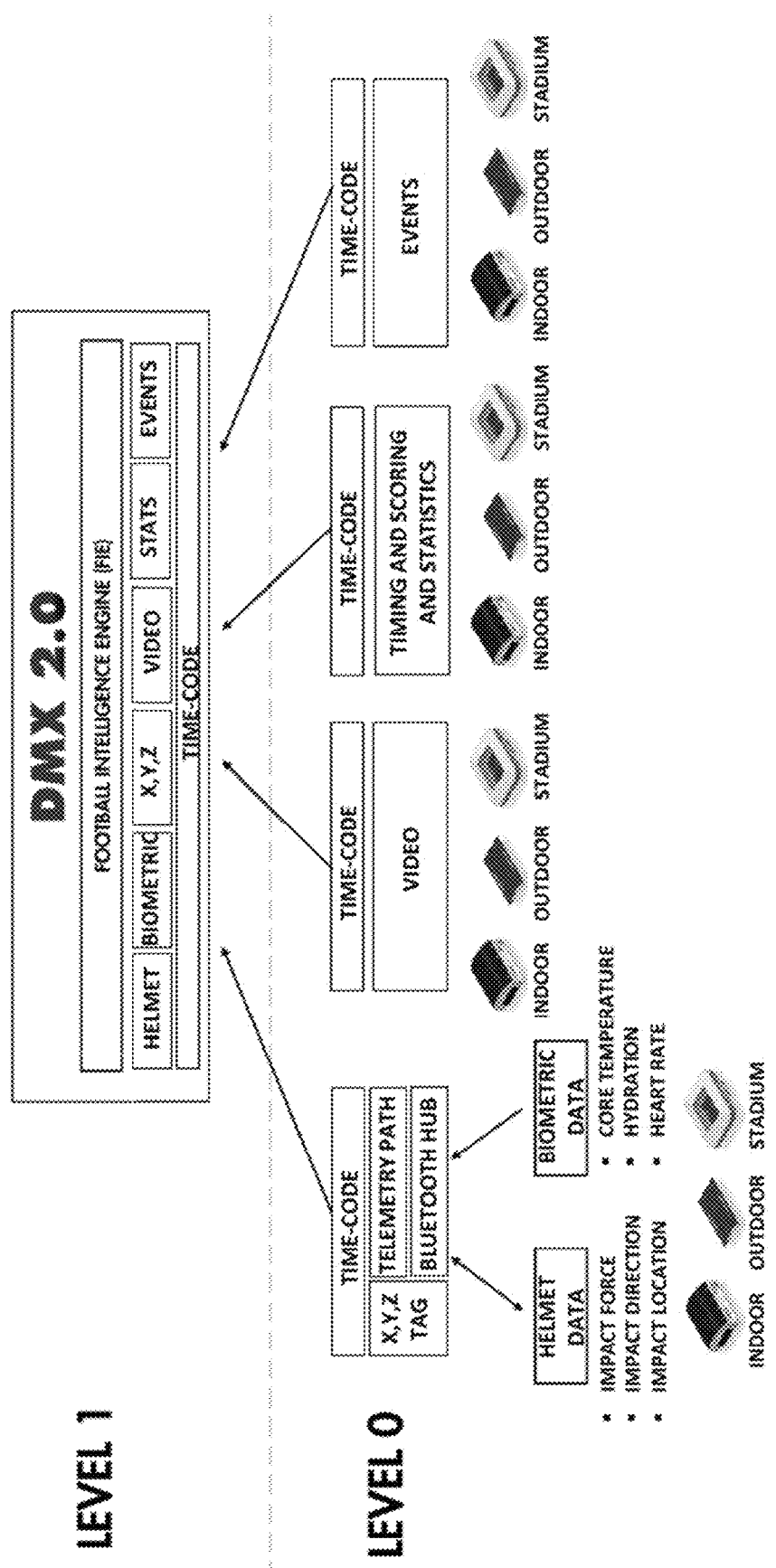
FIG. 6 is an illustration of the interactions between level 0 and level 1 in FIG. 1.

FIG. 1 shows an architecture diagram illustrating an integral system for data collection and analytics for sports activities according to the present invention. The sports activities in the present invention can be sports events, sports games, practice, training sessions, and other sports related activities. There are three levels in the integral system. Level 0 (L0) is for data collection. Level 1 (L1) is a cloud-based platform providing sports intelligence. Level 2 (L2) is intelligent data subscription by different parties for different purposes including but not limited to coaching, training, medical safety, live announcement, broadcasting, display, analytics, and combinations thereof. At a high level summary, L0 generates data from sensors and/or inputs; L1 collects data from L0 sources and analyzes the data and stores the data; L2 accesses or receives data and/or analytics, and may also analyze. FIG. 2 is a detailed diagram of L2 in FIG. 1. FIG. 3 is a separate diagram of L1 in FIG. 1. FIG. 4 is a separate diagram of L0 in FIG. 1. FIG. 5 is an illustration of the interactions between L1 and L2 in FIG. 1. L1 provides L2 analytics data in real time push, and L2 has licensed access to L1 via Application Programming Interface (API). FIG. 6 is an illustration of the interactions between L0 and L1 in FIG. 1. L0 transmits generated data from sensors and/or inputs to L1.

Tracking technologies and wearable technologies are developing fast and changing paradigms of many traditional industries. As applied for sports practices or competitions, or for games (e.g., virtual sports or gaming), each player's or participant's location, movements, and/or vital signs or other biometric data are sensed and tracked and the location data, movement data, and/or biometric data are collected and transmitted in real time with a time code associated with each of them for more intelligent and time-sensitive (real-time or near-real-time) analytics. The outputs and analytics from the data stored at the L1 platform level are applied to improve individual player or participant performance, team performance, broadcasts, viewer experience, predictive analytics of the sport or game, and combinations thereof Level 0: Data Capture, Generation, Inputs, and Collection from Data Sources At least one data source or sensor is provided for generating data, capturing data, receiving inputs, and/or collecting data; in every case, the data automatically receives a time code that is inextricably linked with the data, which is preferably real-time or near-real-time data. In a preferred embodiment of the present invention, the data is associated with at least one athlete or player or participant for at least one sport or game (including but not limited to a virtual reality game or video game). At Level 0, at least one sensor is placed on different areas of the player or participant body(ies) to measure movement, location, and/or biometric data for each player or participant.

Traditionally, optical tracking systems with cameras are deployed to track objects in soccer and basketball games. Comparatively, more complicated sports, for example American football, there are a multiplicity of complex offensive and defensive sets as well as constant player substitution throughout a practice or competition. These higher levels of activity, variables, and complexity in the sport or game practice and competition make it impossible for humans to simply use optical tracking systems with cameras without more advanced tracking technology and automated analytics.

Furthermore, Global Positioning System (GPS) technology for civilian use has a maximum horizontal location accuracy of three meters, which is not accurate enough to know where exactly a player is on the sports field, particularly if the goal is to assess proximity to another player, e.g., in American football, a cornerback in man-to-man coverage. While some GPS systems can use additional technologies to refine accuracy further, it's not adequate standalone. Radio-Frequency Identification (RFID) is accurate up to six inches. In a preferred embodiment of the present invention at L0, RFID technology is used for location tracking of a multiplicity of players in a sport or a game.

The present invention provides for use of RFID technology as well as GPS for location tracking. In one illustrative embodiment for American football, every National Football League (NFL) stadium has about 20 RFID receivers, as part of a location tracking system designed by Zebra Technologies, placed around the field for receiving data transmitted by RFID tags attached to players' uniforms.

In one exemplary embodiment, two small tags housing RFID chips are removably attached to each of the multiplicity of players' uniforms to wirelessly communicate location data; more particularly, each of the RFID chips is removably attached to and equipped into each of two shoulder pads for each American football player. The small tags also contain an accelerometer for measuring speed. The sensor chips, about the size of a quarter in diameter and about two quarters thick, run on small, watch-type batteries that provide a power supply for the tags for operation for up to about one year. Also, while the tags are removably attached, their robust design is preferably water-resistant and impact-resistant to provide for inclement weather exposure, sweat, and washability, and to incur hard hits without breaking or impairing operation.

System receivers are pinged by the two RFID tracking sensors on each player to identify the location, motion, and direction of every player throughout a game. Motion is tracked in sub-seconds and a player's location is identifiable within about six inches accuracy. The sensor tags operate to blink up to 85 times per second and transmit motion within 120 milliseconds, thereby providing real-time or near-real-time data.

The RFID tracking sensors are operable to provide data or information on player movements during the game, for example but not limited to location, speed, acceleration, deceleration, player orientation, braking force, change of direction, for every player at every play with extreme accuracy. The RFID tracking sensors are operable to provide real-time (or near-real-time) statistics for every movement of every player on every inch of the field in every NFL game or other sport or game. Further, these inputs and their corresponding data transmitted to the L1 platform for analytics and database storage are operable to provide more intelligence and insight into the sport or game than ever before in the prior art, including but not limited to player distance traveled, maximum and average speeds, and accelerations and decelerations.

These inputs, for example, movement data can be combined, integrated and correlated or otherwise associated with other data, by way of example and not limitation, activity trackers, sleep trackers, diet apps to log caloric intake, and combinations thereof, to better monitor and evaluate players' physical performance continuously. Advantageously, the present invention uniquely provides for the analytics of any of the multiplicity of inputs and corresponding time code for synchronization.

In one embodiment, RFID tags also have Bluetooth transmitters or radios, which make the RFID tags expandable. The RFID tags enabled with Bluetooth are operable to precisely connect other wearables and collect more data with time code in real-time (or near-real-time) and transmit to the cloud-based platform of the present invention.

One example of commercially available RFID tracking technology (from Zebra) is provided in the following issued U.S. issued patents or pending application: U.S. Pat. Nos. 9,002,485, 9,014,830, 9,180,357, 20150148129, 20150149837, 20150356332, and 20150375083, each of which is incorporated by reference herein in its entirety.

Wearables includes any sensory wearables attached to different parts of the body, by way of example but not limitation, Fitbit heart rate monitors, hydration patches, fluid or sweat sensors, optical sensors, etc. Wearables also include clothing and personal sports gears embedded with sensors, by way of example and not limitation, helmet with impact sensors, mouth guard with temperature sensor and hydration sensor, garments with various biometric sensors. Biometric data includes, by way of example and not limitation, heart rates, lung capacities, core body temperatures, hydration, respiration, impact metrics, etc.

Figure 10:
FIG. 10 is a list of potential partners providing consumable products having biometric data capturing function.

FIG. 7 is a list of potential partners providing wearable clothing having biometric data capturing function. FIG. 8 is a list of potential partners providing wearable bands having biometric data capturing function. FIG. 9 is a list of potential partners providing wearable patches having biometric data capturing function. FIG. 10 is a list of potential partners providing consumable products having biometric data capturing function. FIG. 11 is a table comparing potential partners providing wearable and consumable products having biometric capturing function.

FIG. 12 is a list of potential partners providing head impact sensing systems.

External environmental data are also collected, by way of example but not limitation, temperature, humidity, chemicals, and other environmental factors and hazardous conditions.

All these sensory data at a granular level allow improved assessment of player(s) and team performance, health or medical status, competitive intelligence across teams, and combinations thereof, based on real-time (or near-real-time) quantitative data, which provides significant advantages over the prior art.

In addition to the sensory data described hereinabove, cameras or video capture devices are used to provide inputs.

Video data is time-coded and transmitted to the cloud-based platform at L1 for synchronization with any of the multiplicity of inputs from L0. Meanwhile, timing and scoring and statistics information related to the sports game is also collected and time-coded and transmitted to the cloud-based platform at L1. For example, timing and scoring information includes but not limited to, timeouts, shot clock, power plays and inning. Statistics includes individual statistics, for example but not limited to scores, attempts and assists; statistics further includes team statistics, for example but not limited to total shooting, total assists and total penalties. Further, different events happening during the sports game are also collected as data input to the cloud-based platform at level 1. For example but not for limitation, different events include whistles, snaps, flags, warnings, etc.

This detailed description of the present invention includes inserting content into an image sequence and video event statistic tracking, including the following issued U.S. patents by common assignee SportsMedia Technology: U.S. Pat. Nos. 5,504,312, 7,116,342, and 7,868,914, each of which is incorporated by reference in its entirety herein.

The above-depicted sensors may transmit sensor signals via one or more wired or wireless communication protocols. For example, any proprietary or standard wireless protocol Ultra-Wide Band (UWB) (e.g., IEEE 802.15.4), near field communication (NFC), Bluetooth, Wi-Fi (e.g., a 802.11 protocol, etc.), ISO/IEC 18000, radio frequency systems (e.g., 900 MHz, 1.4 GHz, and 5.6 GHz communication systems), Zigbee, infrared, mobile broadband, GSM, GSM plus EDGE, CDMA, quadband, and other cellular protocols, Voice Over Internet Protocol (VOIP), and/or any other suitable protocol.

Communication protocols and data collection systems are selected based on the location of the sport event, by way of example and not limitation, indoor, outdoor, or stadium.

Level 1: Data Processing, Integration, Analytics, and Storage

In the present invention, the cloud-based platform at level 1 (L1) includes different rules engines to provide sports intelligence based on various data collected from level 0 (L0).

Many sensor devices of the prior art and available commercially for use in sports and/or games that may be used at L0 in the systems and methods of the present invention are not operable to cross-communicate with each other, and very often the data formats are different as well, and may be incompatible. This is one of the biggest challenges in any industry, and is a longstanding, unmet need in the field of athletics, sports, and gaming. Traditionally in the prior art, only similar data sets are accepted that provide the same kind of information or data and operate with the same language or communications protocol. If there are different data sets, then the prior art requires data collation and synchronization to be done manually. The cloud-based platform is operable to automatically aggregate, correlate and synchronize multiple on-site data feeds with time code from different devices at L0 into a proprietary database. The cloud-based platform is vendor agnostic and sensor agnostic, which means it complements any sensor product from any vendor for data collection. The cloud-based platform is operable to provide customizable data integration product for a variety of client events.

The proprietary database is operable to store all the live and historical sensory data, video, stats, and events. In one embodiment, the cloud-based platform is operable for automatic comparison of various live data and historical data for a player, a team and/or a game. In one embodiment, the cloud-based platform is operable to build player profile and game profile based on various live and historical data stored in the proprietary database. In one embodiment, the cloud-based platform is operable to provide intelligent statistics for a player, a team, and a game based on various live and historical data stored in the proprietary database. In one embodiment, the cloud-based platform is operable to integrate with social media and extract social media feeds related to a player, a team or a game during a predetermined time period.

The cloud-based platform is operable to query and retrieve in and from the proprietary database for intelligent analytics. In one embodiment, the cloud-based platform is operable to provide advanced sports analytics and trends for relevant parties. For example but not for limitation, the cloud-based platform is operable to provide answers to the following questions: How far did that player actually run to gain four yards? How fast? When, exactly, did he start running out of steam? In one embodiment, the cloud-based platform is operable to build a predictive model for prediction, by way of example and not limitation, what actions coaches, trainers, and/or medical staff are required based on player profile and current statistics.

In one embodiment, the biometric data are transmitted from multiple sensors, the cloud-based platform is operable to synchronize the biometric data with time code and perform analytics for the inter-relationship of the biometric data, not just analytics for their independent values.

The analytics performed by the cloud-based platform can provide insights for teams about players and future match-ups, improve player performance and team performance, prevent injuries, improve fan engagement and view experience. Thus, the cloud-based platform creates significant value to coaches, players, trainers, medical staff, broadcasters, and fans.

With improved data and analytics provided by the present invention from L1, coaches, trainers, and any authorized third party can access the data from L1 to L2 via API to customize training sessions for each player or groups of players having at least one common factor, such as position on a team, essentially personalizing practice around the different requirements for the different positions or roles on the team, for example in American football, nose tackles versus wide receivers. While athletic performance personnel associated with any team may have a different subjective answer for why a player's performance varies, the athletic performance personnel (e.g., coaches or trainers) can use the outputs from L1 at L2 for developing and deploying tailored, customized training plans for individual players and positions based on their strengths and weaknesses and the quantitative data associated with each player from practices and/or competitions or games. In another example at L2, medical staff as well as coaches and trainers, can receive alerts for each of the multiplicity of players, e.g., if a player is dehydrated, or if their heart rate is too elevated, or if the impact on the player is above a threshold, etc.

The cloud-based platform in the present invention provides complete integration of dynamic statistical data and graphical content created specifically for each client broadcast. Fans and viewers are able to experience a new level of engagement like never before with the combination of historical and live stats, real-time video, clock-and-score, social media posts and hashtag battles. By way of illustrative example, fans and viewers will be able to see more complex information, such as how quickly and how far linemen were able to push back a defensive player to make a hole for a running back, and even social media feeds which are popping up on the in-stadium display or apps.

FIG. 13 is a list of features of level 1 according to one embodiment of the present invention. The present invention is used in football, and L1 includes a Football Intelligence Engine (FIE). The FIE stores information for each player, for example number of plays for a player in a game and in a season and biographical data for a player (height, weight, etc.); integrates data from L0, for example, live and season to date location data, position on the field at the start, during a play and at the end of a play; integrates manual event markers from marking apps; integrate linear timecode data; and integrates statistical data.

FIG. 14 is a list of events marked for a marking application program ("app") according to one embodiment of the present invention. The marking app marks time for start of play, end of play, time of hand off and/or quarterback release, start of run with ball, end of run with ball, quarterback release of pass, start of route, end of route, reception, first contact and tackle. The marking app also marks players, for example targeted receiver on pass, ball carrier on run, and tackler.

Level 2: Data Application and Subscription for Access to Data

The analytics performed by the cloud-based platform can provide actionable data for different parties (for example, coaches, trainers, medical staff, live announcer, broadcast, in-stadium display, fans, viewers, etc.) involved in a sport or game.

In one embodiment, an application program ("app") is provided for a certain party or specified or predetermined use with licensed access to subscribe to receive relevant actionable data in real time push from the cloud-based platform and/or interact with the cloud-based platform via Application Programming Interface (API). Apps at level 2 (L2) are operable to repackage the data from L1 and provide to different parties, including but not limited to coaches, trainers, medical staff, live announcers, broadcasters, displays, viewers, fans, and combinations thereof. Each of the certain party apps are customized for the use and format of the data for the specified or predetermined use (limiting use based upon what type of data is used, what if any analytics are used, who is authorized, privacy, authentication, data format, etc.).

In another embodiment, the cloud-based platform also provides licensed access to the proprietary database. Third party analytics providers can obtain licensed access to the various data stored in the proprietary database; these third party analytics providers may generate complementary analytics independently from the platform at L1.

For example, coaches have a coaching app on their tablets or smart phones or other computing devices. The coaching app is operable to receive and/or request videos in real time from the cloud-based platform. The videos have inserted real-time data or statistical data collected from L0. The coaching app is also operable to replay certain parts of the video with inserted real time data or statistical data. The coaching app provides data and/or analyzed data outputs within interactive graphic user interface (GUI) formats that enable coaches to make decisions based on current situation during a sports competition and/or practice or training.

Also, for example, trainers have a training app operable on remote mobile devices or computing devices, e.g., on tablets, smart phones, computers, or other computer devices, with interactive real-time GUIs. The training app is operable to receive and/or request biometric data and videos in real-time or near-real-time or at predetermined times or events or triggers. The training app is also operable to request historical biometric data statistics and player profiles. The training app enables trainers to make personalized training plans for individual players and improve their performances in practice, as well as in the sport events or competitions, or virtual games.

Also, for example, medical staff have a medical safety app on their tablets or smart phones or other computing devices, e.g., on tablets, smart phones, computers, or other computer devices, with interactive real-time GUIs. The medical safety app is operable to receive movement data and biometric data for individual players in real-time or near-real-time from the cloud-based platform. The medical safety app provides medical safety alerts to medical staff via interactive GUI, for example, as illustrated in the figures, and the medical staff can take actions or request players to take actions based on the alerts, triggers, or notifications, so that injury, overexertion, dehydration, fatigue and other unwanted conditions may be prevented or ameliorated.

For example, live announcers have a corresponding app on a mobile computing device e.g., on tablets, smart phones, computers, or other computer devices, with interactive real-time GUIs. The live announcer's app is operable to receive and/or request videos in real-time or near-real-time. The videos have inserted real-time data or statistical data collected from level 0. The live announcer's app keeps live announcers updated with graphics and data in real time so that live announcers can make their announcements in a more accurate and timely manner.

For example, broadcasters have a corresponding app operable on a mobile computing device, e.g., on tablets, smart phones, computers, or other computer devices, with interactive real-time GUIs. The broadcaster's app is operable to receive videos and location data in real-time or near-real-time and/or replay certain parts of the videos with inserted data. The broadcaster's app enables broadcasters to do telestration more timely and effectively and make better broadcast.

For example, in-stadium display also has a specific application program, not just showing the videos in real time for the viewers but also displaying rich inserted data at the same time, including but not limited to events during a sports game, player profile, location and movement data and biometric data and alerts for individual players. This solution provides for the on-site viewers' experience to be improved significantly.

In one embodiment, the present invention is used in football.

FIG. 15 is a list of features for a talent prompter at level 2 according to one embodiment of the present invention. The talent prompter in FIG. 15 provides offense information, including personnel group information and personnel group alert information. The personnel group information includes player number for each offense possession, number of plays of grouping during game, total yards gained with grouping, and average yards gained with grouping. Similarly, the talent prompter in FIG. 15 also provides defense information. The talent prompter in FIG. 15 further provides main screen alerts including key matchups, which is predetermined before start of game, first time on field for offense, mismatches for positions, sizes and/or speeds. FIG. 24 is a sample screenshot for a talent prompter screen.

FIG. 16 is a list of features for a research prompter at level 2 according to one embodiment of the present invention. The research prompter in FIG. 16 provides for offense information and defense information.

Figure 35B:
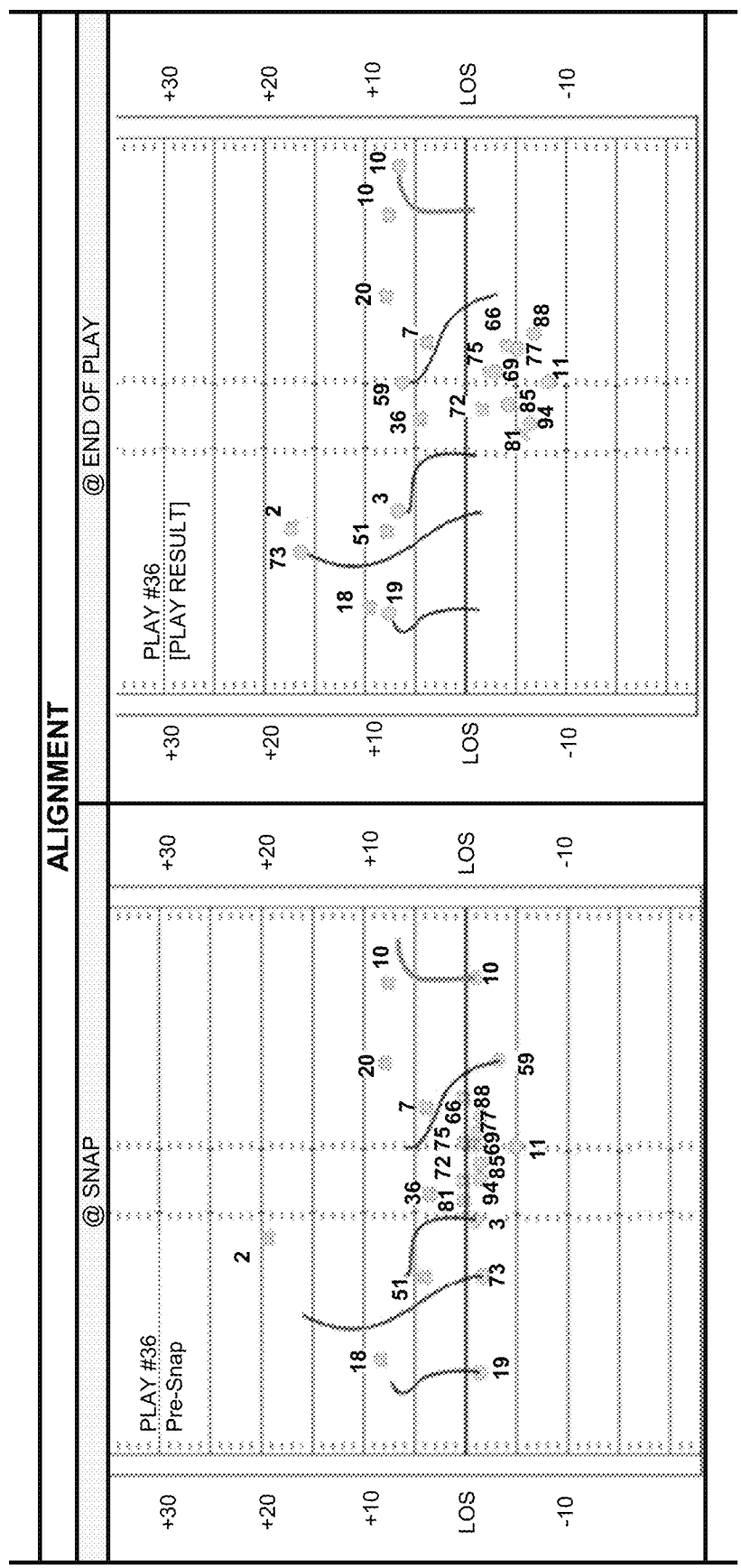

FIG. 17 is report as a product of level 2 according to one embodiment of the present invention. Detailed report templates and examples are provided in FIGS. 25A-35. FIGS. 25A and 25B is an offense summary template for game. FIGS. 26A and 26B is an offense summary template for practice. FIG. 27 is a defense summary template for game. FIG. 28 is a defense summary template for practice. FIGS. 29A and 29B is a play summary template for game. FIG. 30 is a play summary template for practice. FIG. 31 is a grouping summary template for game. FIG. 32 is a grouping summary template for practice. FIG. 33 is an activity summary template for game. FIG. 34 is an activity summary template for practice. FIGS. 35A and 35B and 35C is an example of play summary for game.

FIGS. 18A and 18B is a list of features for telestration and sports Character Generator (CG) for offense according to one embodiment of the present invention. The telestration and sports CG for offense include information for running play, passing play and special team play. FIGS. 21A and 21B illustrate how to use telestration and sports CG for offense in a broadcast according to one embodiment of the present invention.

FIGS. 19A and 19B is a list of features for telestration and sports CG for defense according to one embodiment of the present invention. FIG. 22 illustrates how to use telestration and sports CG for defense in a broadcast according to one embodiment of the present invention.

FIG. 20 is a list of features for sports CG for participation according to one embodiment of the present invention. FIG. 23 illustrates how to use sports CG for participation in a broadcast according to one embodiment of the present invention.

FIG. 36 is a list of potential partners at level 2 providing software for coaching. For example, DVSport provides software that can be used in football, hockey, basketball, and lacrosse. It also provides replay systems for officials, medical staff and sideline. The football coaching software provided by DVSport allows coaching staff to analyze video from games and practices. There is no time code. Also for example, XOS provides software for football, hockey, basketball, and other sports. It also provides recruiting and officiating solutions. The football coaching software provided by XOS allows coaching staff to analyze video from games and practices. There is no time code.

FIG. 37 is a list of potential partners at level 2 providing hardware and analytical software for training. The training software is used by trainers and strength coaches utilize the software to track performance, fitness and fatigue. The hardware is a wearable GPS device tracking movement and come biometrics. The software analyzes activity and produces reports on distance, speed, load, and etc. It is not in real time, nor it works indoors.

Figure 38:
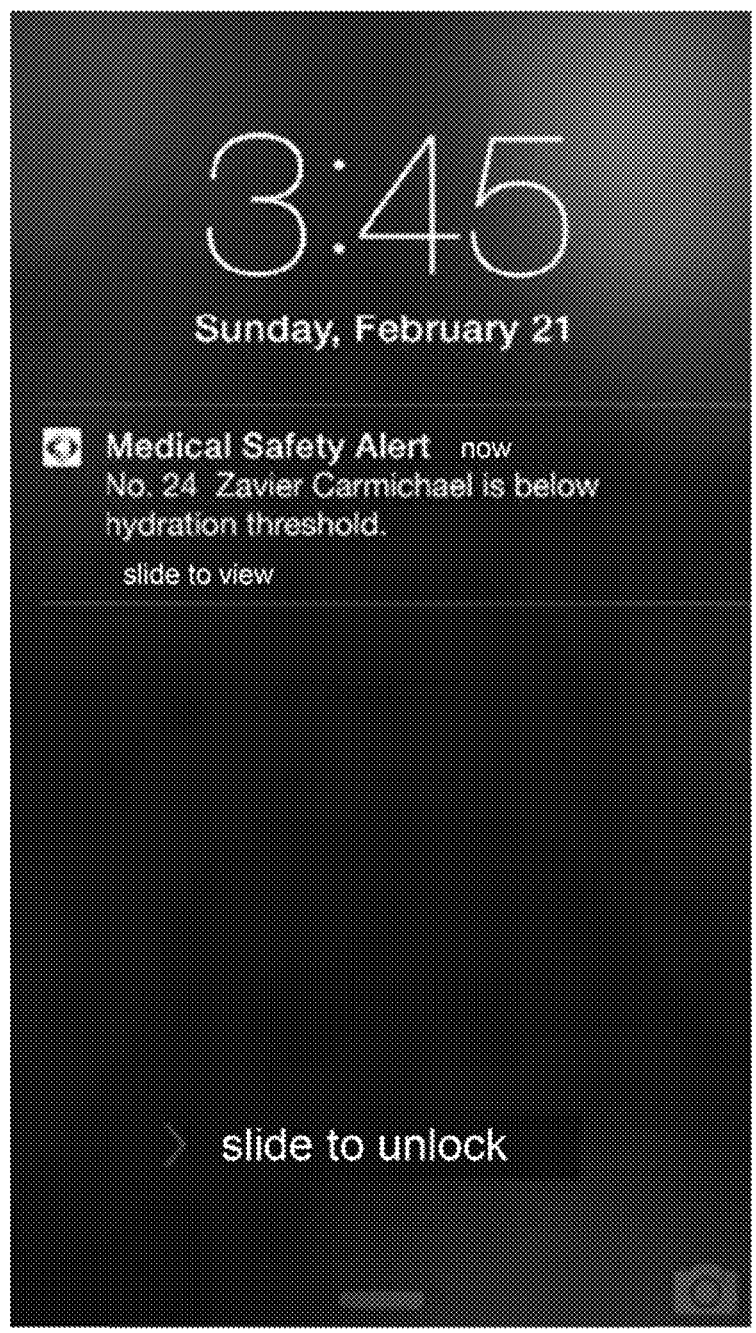
FIG. 38 is a medical safety alert received over a mobile phone showing player No. 24 is below hydration threshold.
Figure 102:
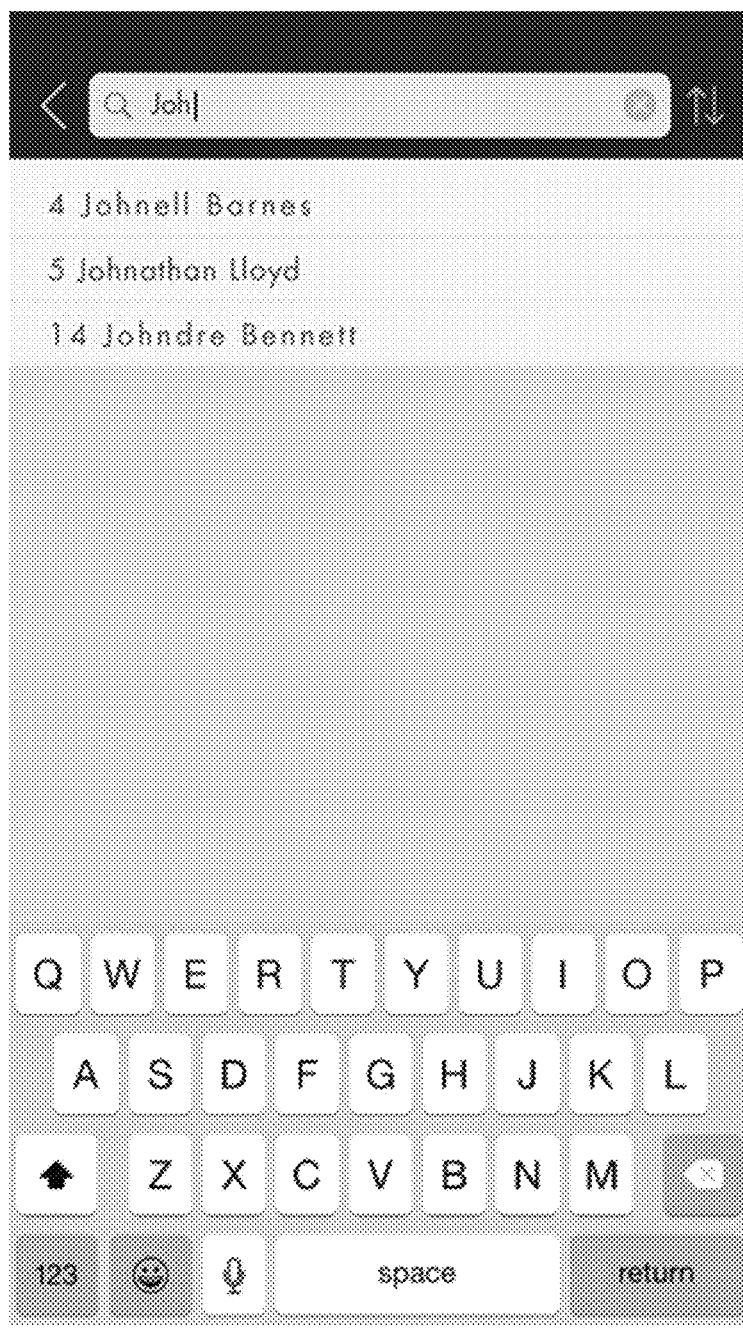
FIG. 102 is a screenshot for typing and searching for a player.

FIGS. 38-102 illustrate an application program used by medical staff of a sports team. The application program enables medical staff to receive medical safety alerts regarding individual players.

FIG. 38 is a medical safety alert received over a mobile phone showing a player is below hydration threshold.

Figure 39:
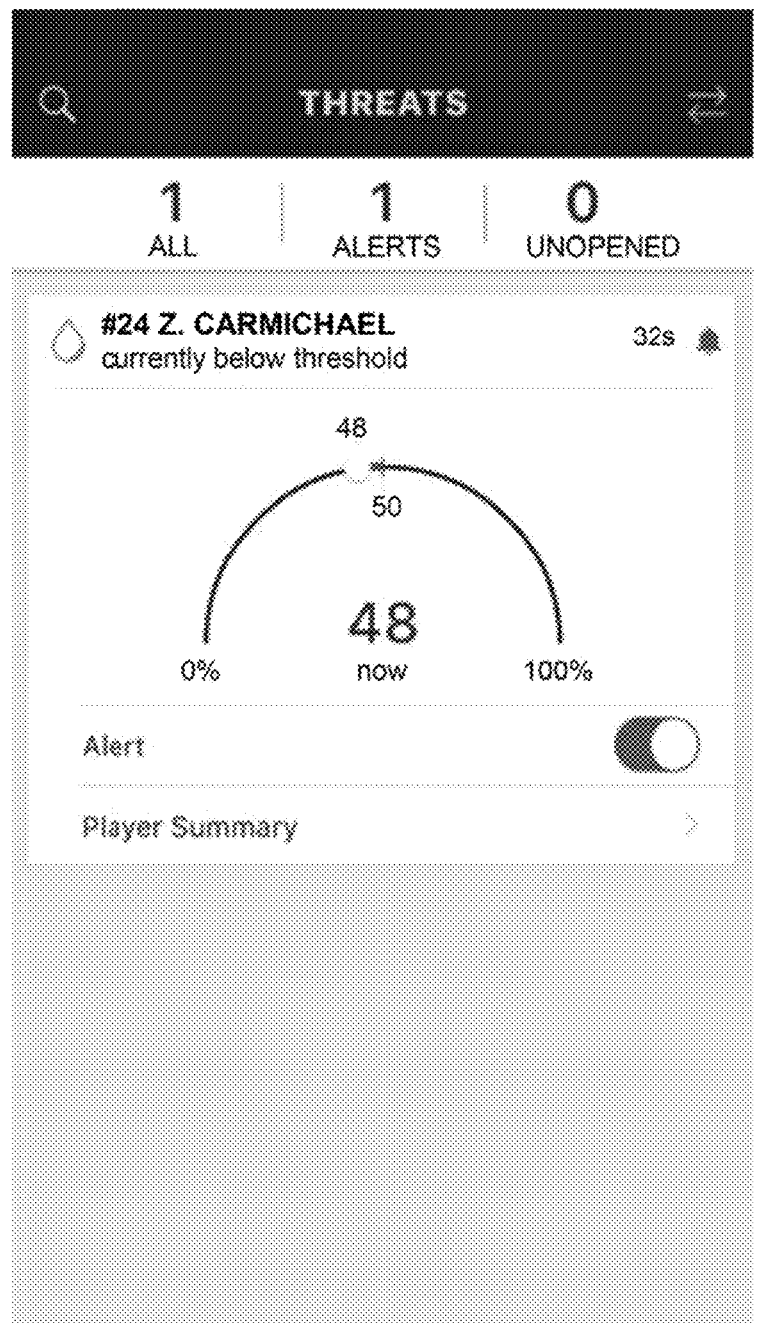
FIGS. 39-41 are screenshots for one embodiment of an application program displaying hydration level below a threshold for player No. 24.
Figure 40:
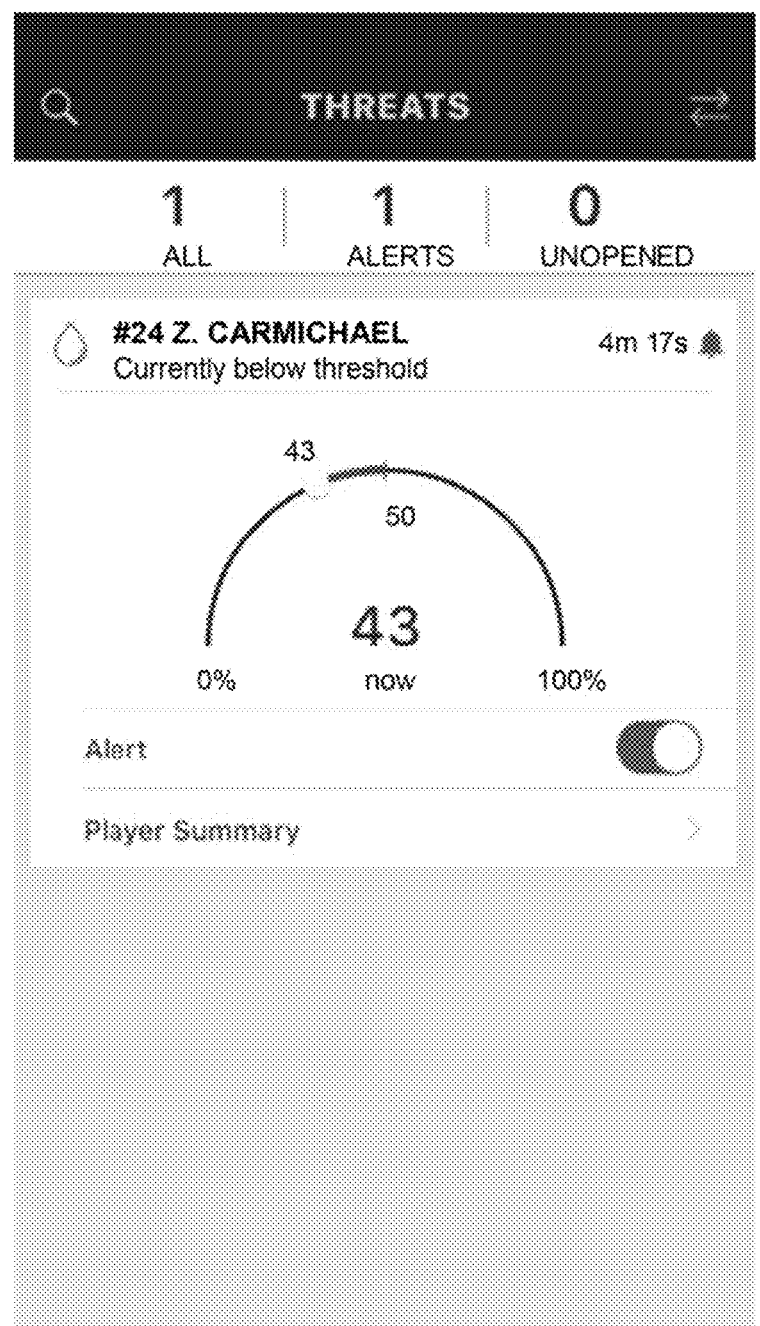
Figure 41:
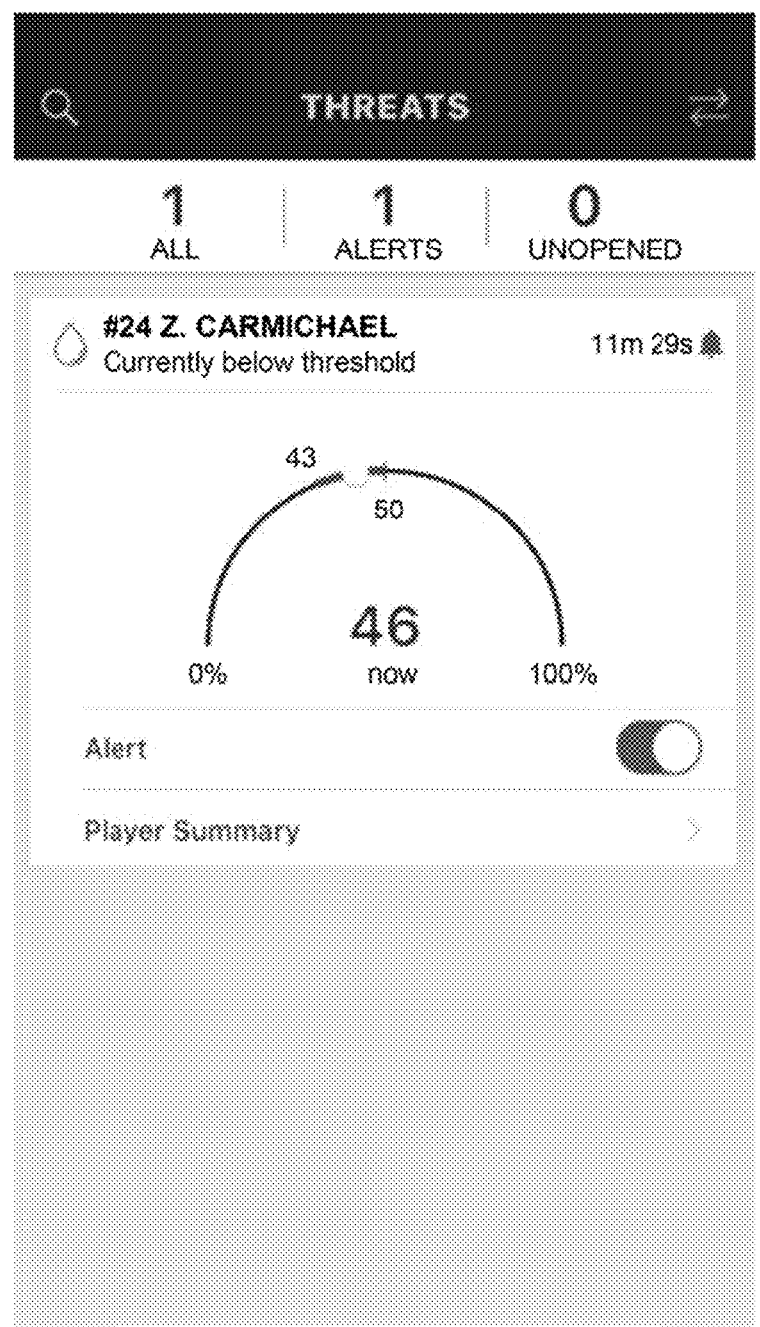
Figure 42:
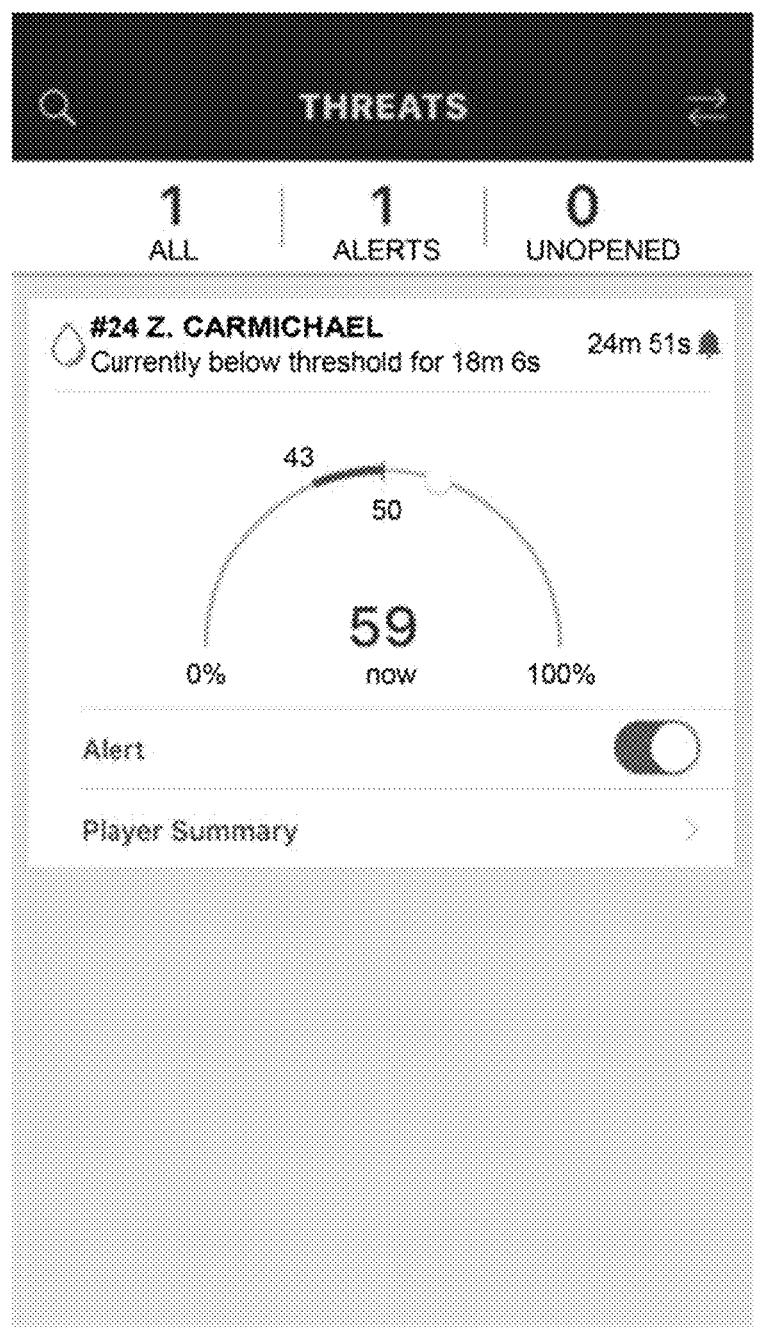
FIG. 42 is a screenshot for one embodiment of an application program displaying hydration level above a threshold for player No. 24.

One embodiment of a medical safety app is shown in FIG. 39. The hydration level is illustrated along a curve from 0% on the left end to 100% on the right end. The threshold is 50% in the middle. The current hydration level for player No. 24 is 48%. If the alert is in red. The hydration level is below threshold at 32s. Similarly, FIGS. 40 and 41 are showing different hydration levels which are also below threshold. FIG. 42 shows that at 24 minutes 51 seconds, the hydration level for player No. 24 is 59%, which is above threshold.

Figure 43:
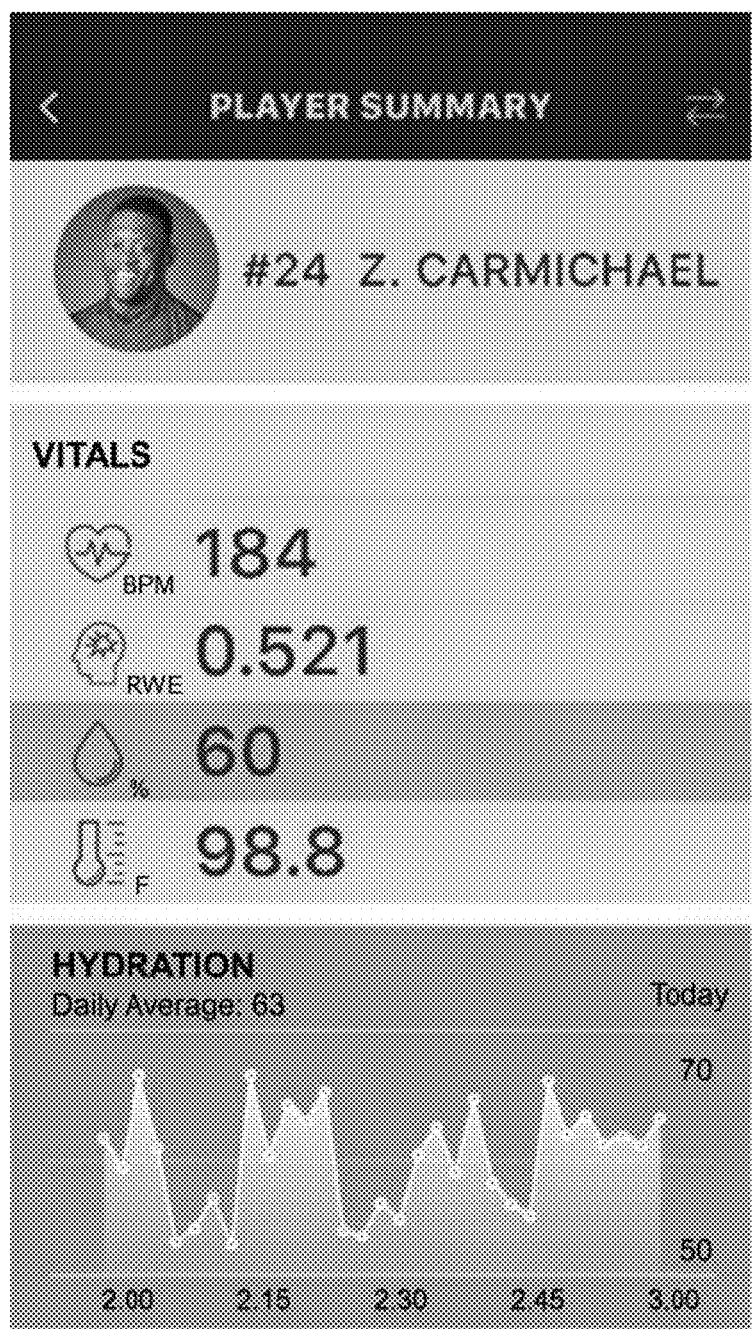
FIG. 43 is a screenshot for displaying player summary for player No. 24.

Player vitals include heart rate, head impact metric, hydration, and core body temperature. FIG. 43 is a screenshot for displaying player summary for player No. 24. His heart rate is 184 Beats per Minute (BPM). The head impact metric is Risk Weighted Cumulative Exposure (RWE). His RWE is 0.521. His hydration level is 60%. His core body temperature is 98.8° F. A diagrammatic view of the hydration level during a time period is also shown in a curve displayed at the lower section of the GUI display when the hydration level is selected, and the real-time data is automatically updated and pushed to the remote mobile device via wireless communication network for automatic updated display on the GUI, and the daily average hydration level is also indicated, shown at 63%.

Figure 44:
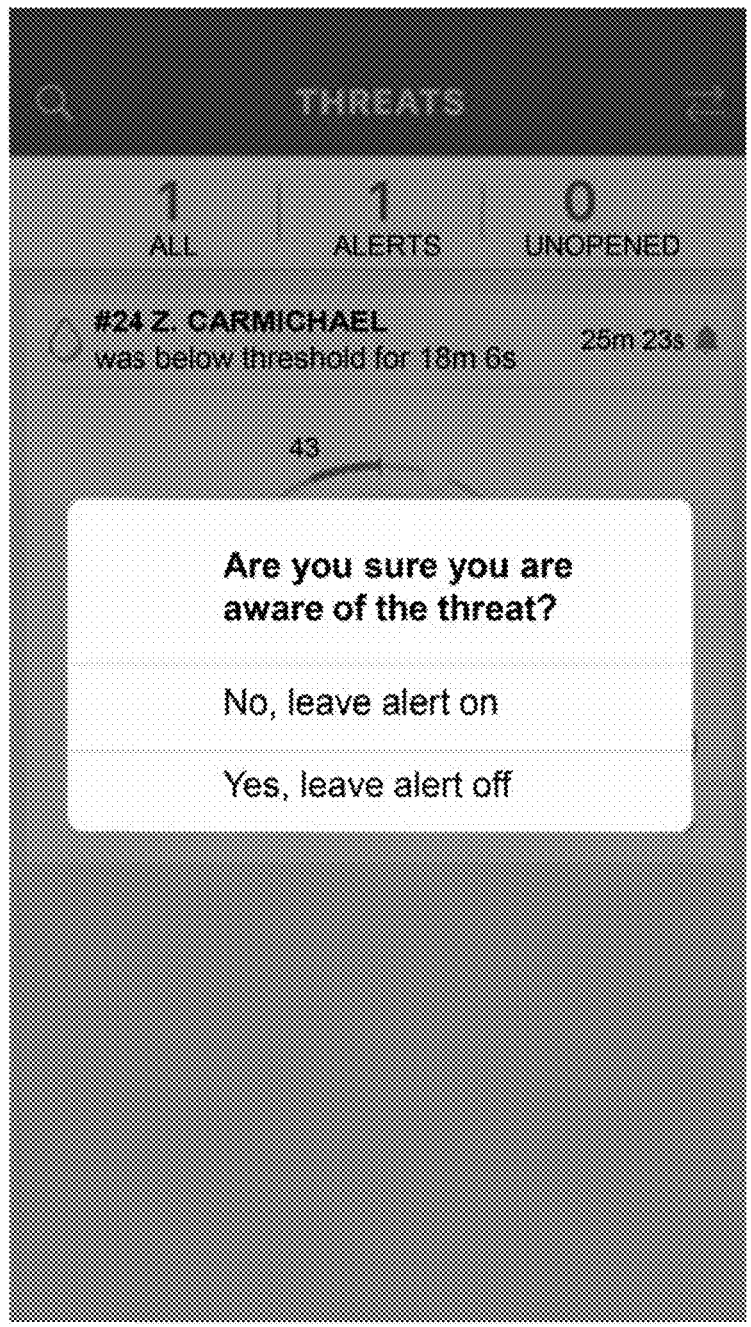
FIG. 44 is a screenshot displaying options of leaving alert one and turning alert off.
Figure 45:
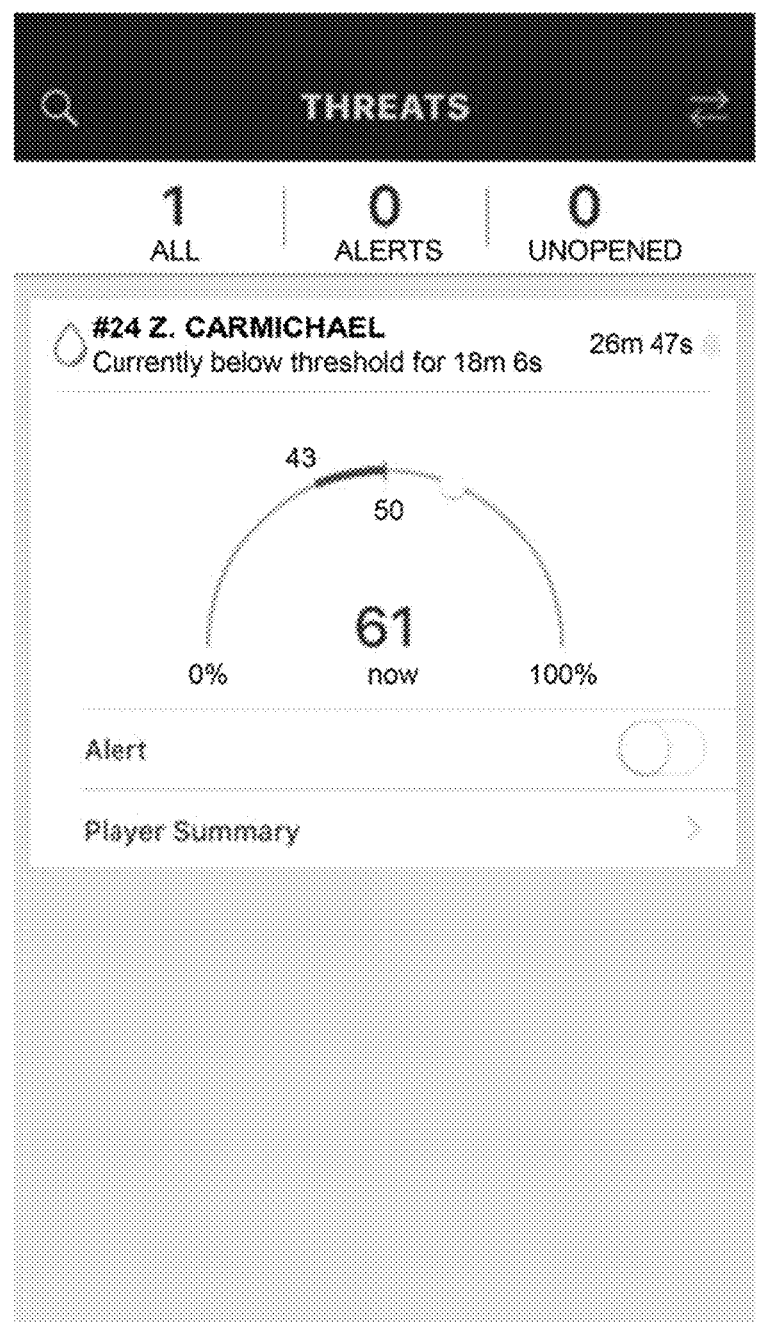
FIG. 45 is a screenshot displaying a medical safety alert is off for player No. 24.

FIG. 44 is a screenshot displaying options of leaving alert one and turning alert off for one embodiment of the application program. FIG. 45 is a screenshot displaying a medical safety alert is off.

Figure 46:
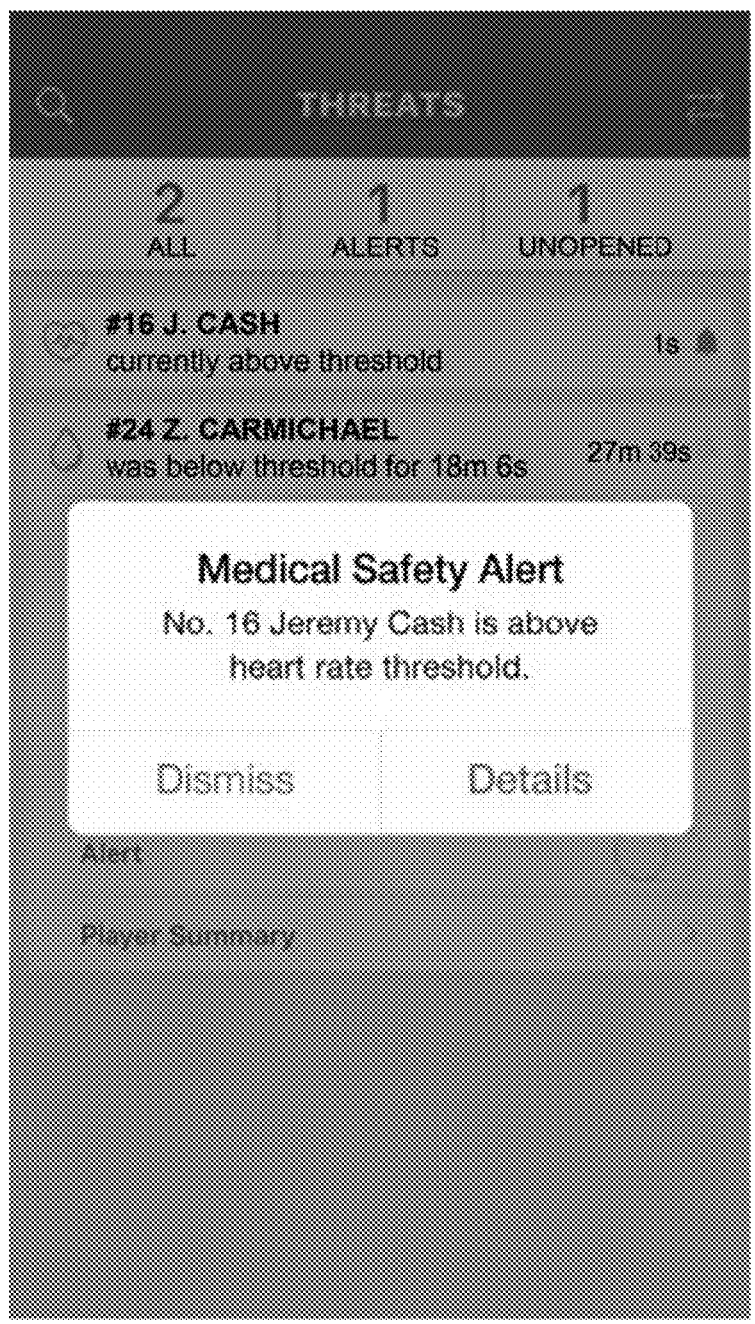
FIG. 46 is a screenshot displaying a medical alert showing player No. 16 is above heart rate threshold.
Figure 47:
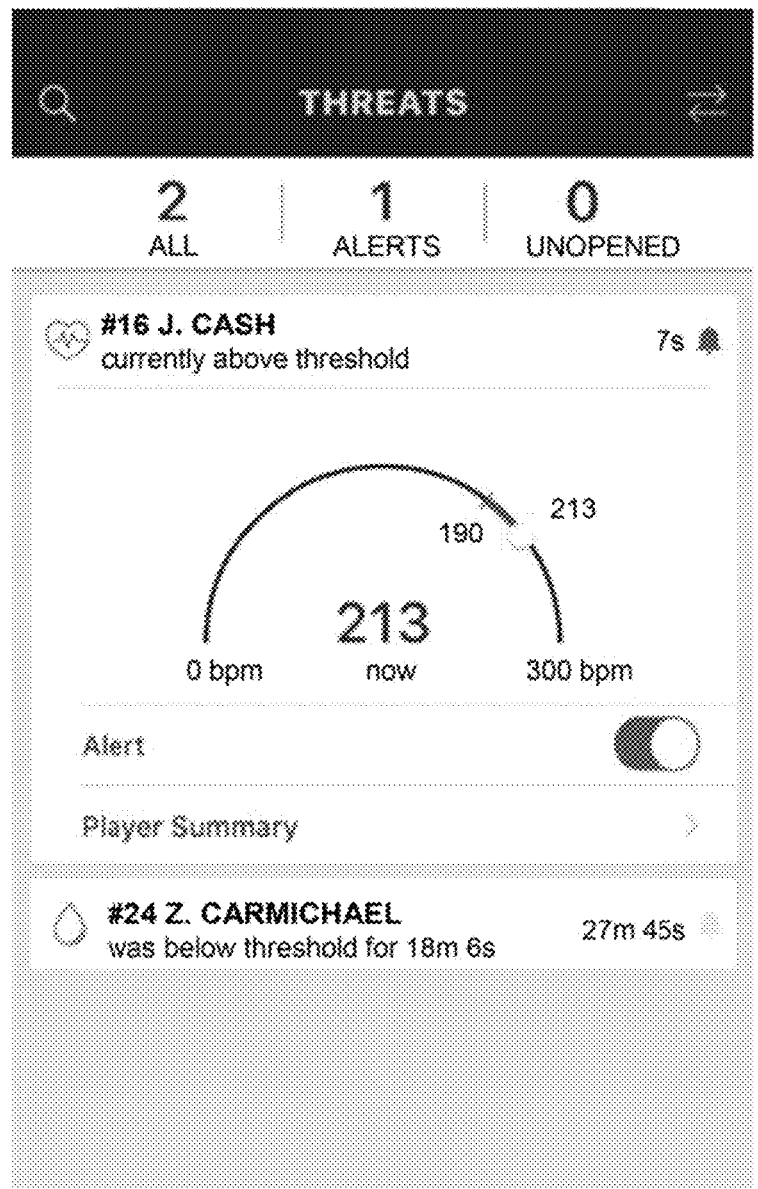
FIGS. 47-49 are screenshots for one embodiment of an application program displaying heart rate level above a threshold for player No. 16.
Figure 48:
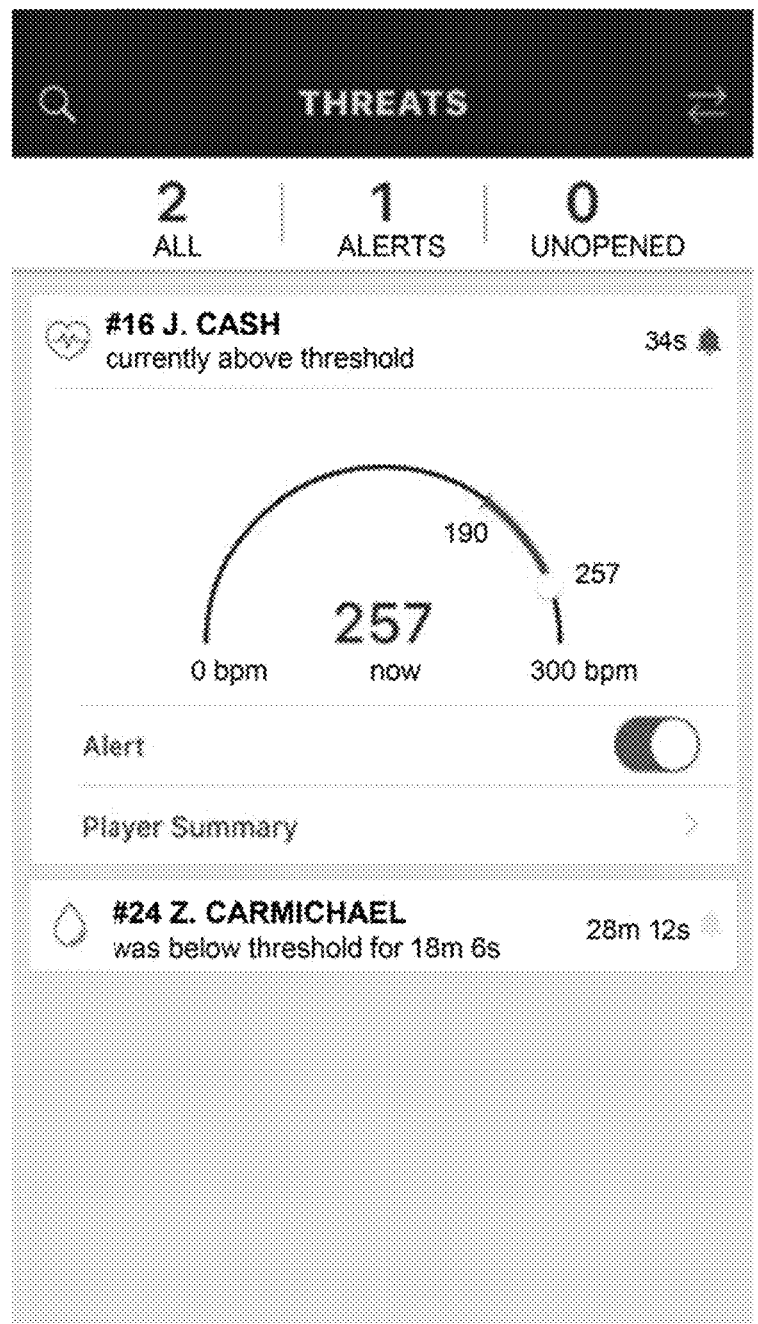
Figure 49:
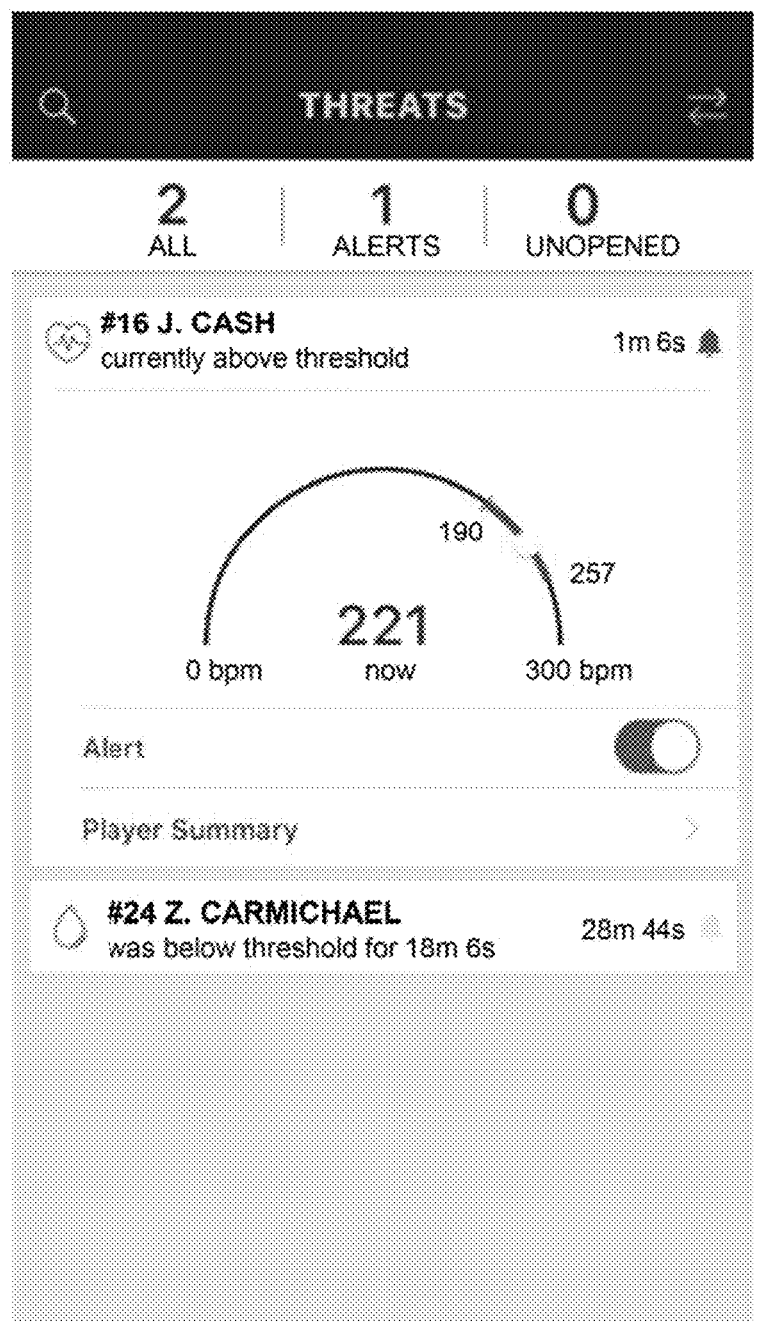
Figure 50:
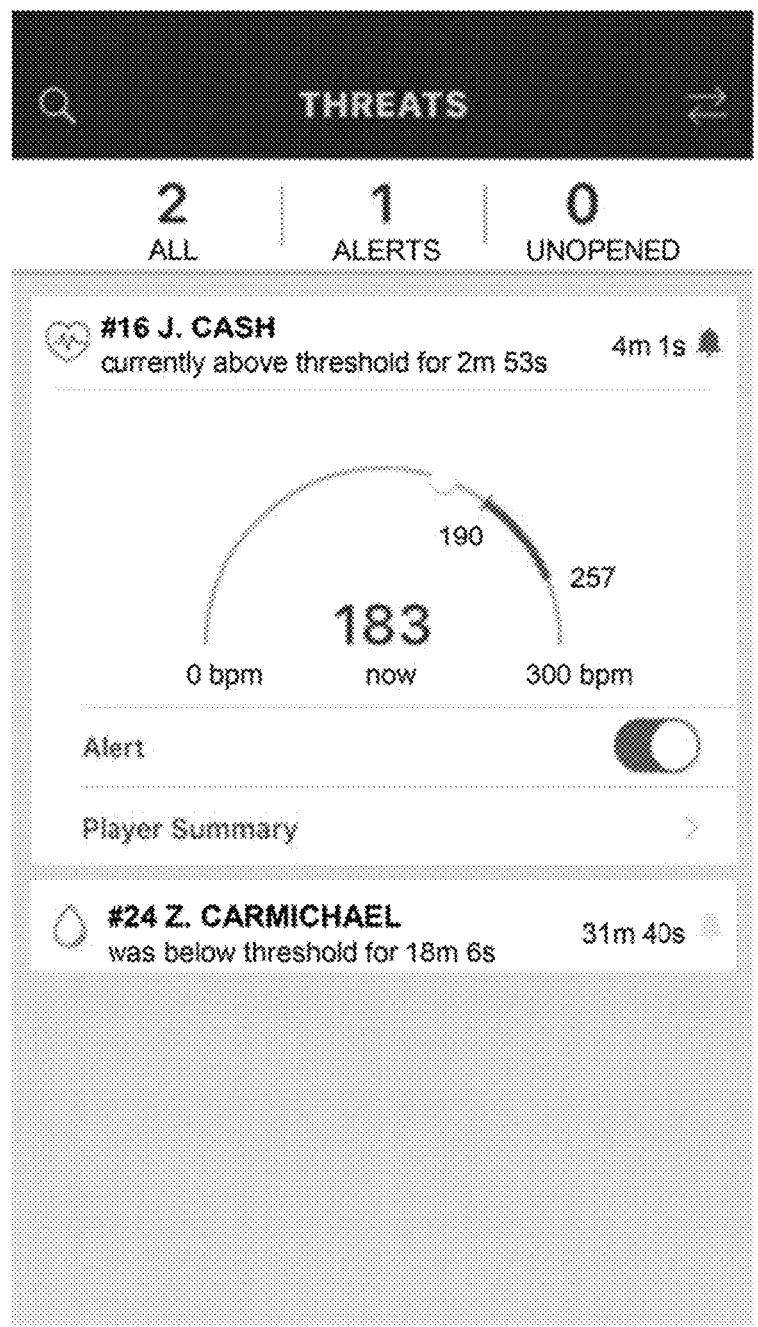
FIG. 50 is a screenshot for one embodiment of an application program displaying heart rate level below a threshold for player No. 16.

FIG. 46 is a screenshot displaying a medical alert showing player No. 16 is above heart rate threshold for one embodiment of an application program. There is an option for dismiss, and an option for details. FIG. 47 shows the details of the heart rate alert. The heart rate is illustrated along a curve from 0 BPM on the left end to 300 BPM on the right end. The threshold is 190 BPM. The heart rate for Player No. 16 is 213 BPM, which is above the threshold. The player name is in red. The heart rate data shown is indicated above threshold at 7 s. Similarly, FIGS. 48 and 49 are showing different heart rates which are also above threshold. FIG. 50 shows that at 4 minutes 1 second, the heart rate for player No. 16 is 183 BPM, which is below threshold. At this time, the player name is in black.

Figure 51:
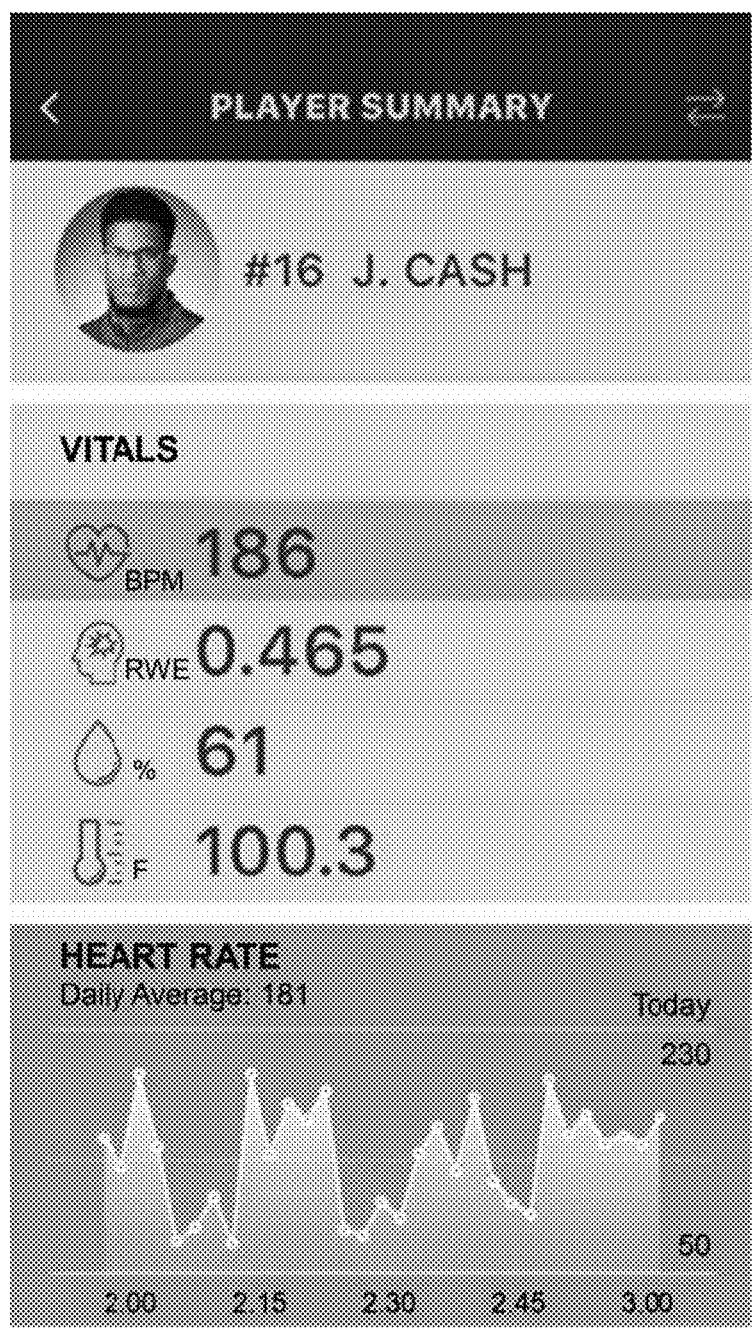
FIG. 51 is a screenshot for displaying player summary for player No. 16.

FIG. 51 is a screenshot for displaying player summary for player No. 16, his heart rate is 186 Beats per Minute (BPM). His RWE is 0.465. His hydration level is 61%. His core body temperature is 100.3° F. A diagrammatic view of the heart rate level during a time period is also shown in a curve displayed at the lower section of the GUI display when the heart rate is selected, and the real-time data is automatically updated and pushed to the remote mobile device via wireless communication network for automatic updated display on the GUI, and the daily average heart rate is also indicated, shown at 181 BPM.

Figure 52:
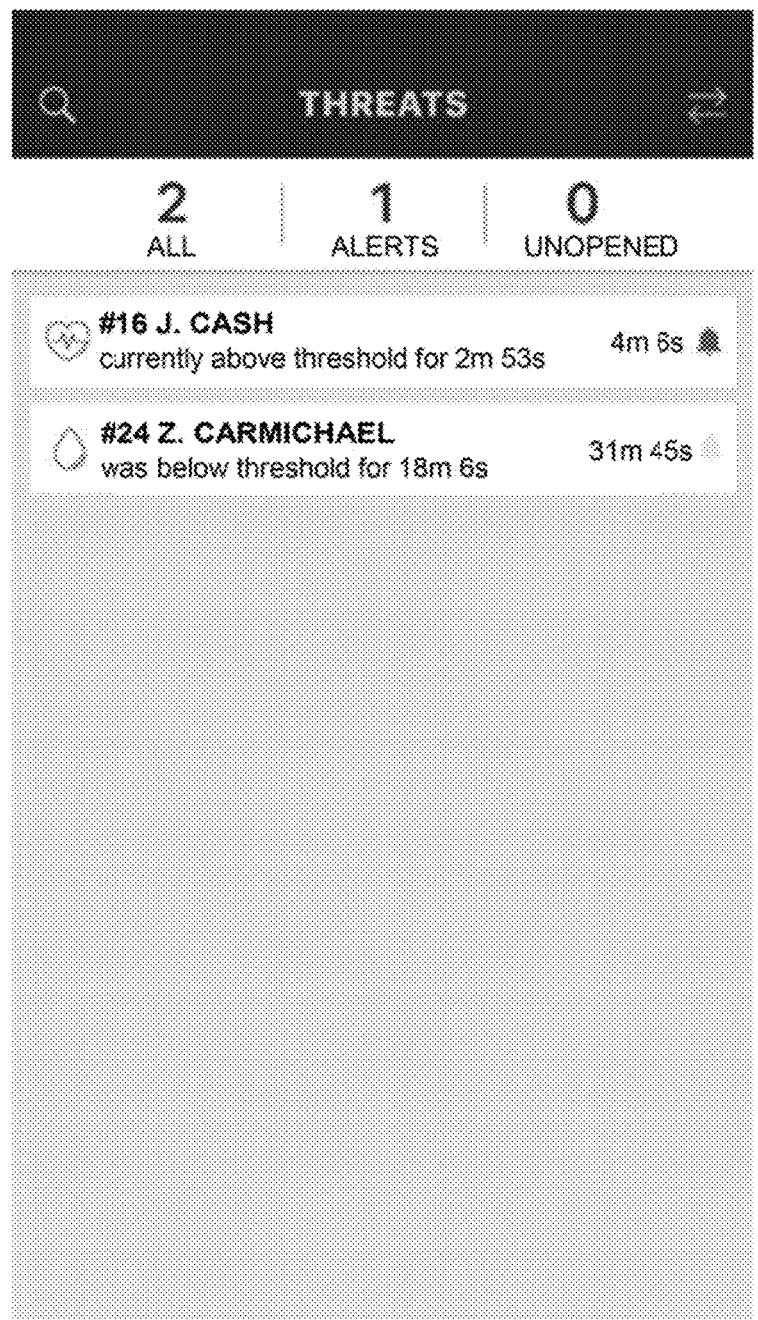
FIG. 52 is a screenshot for displaying all alerts received.

FIG. 52 is a screenshot for displaying all alerts received.

Figure 53:
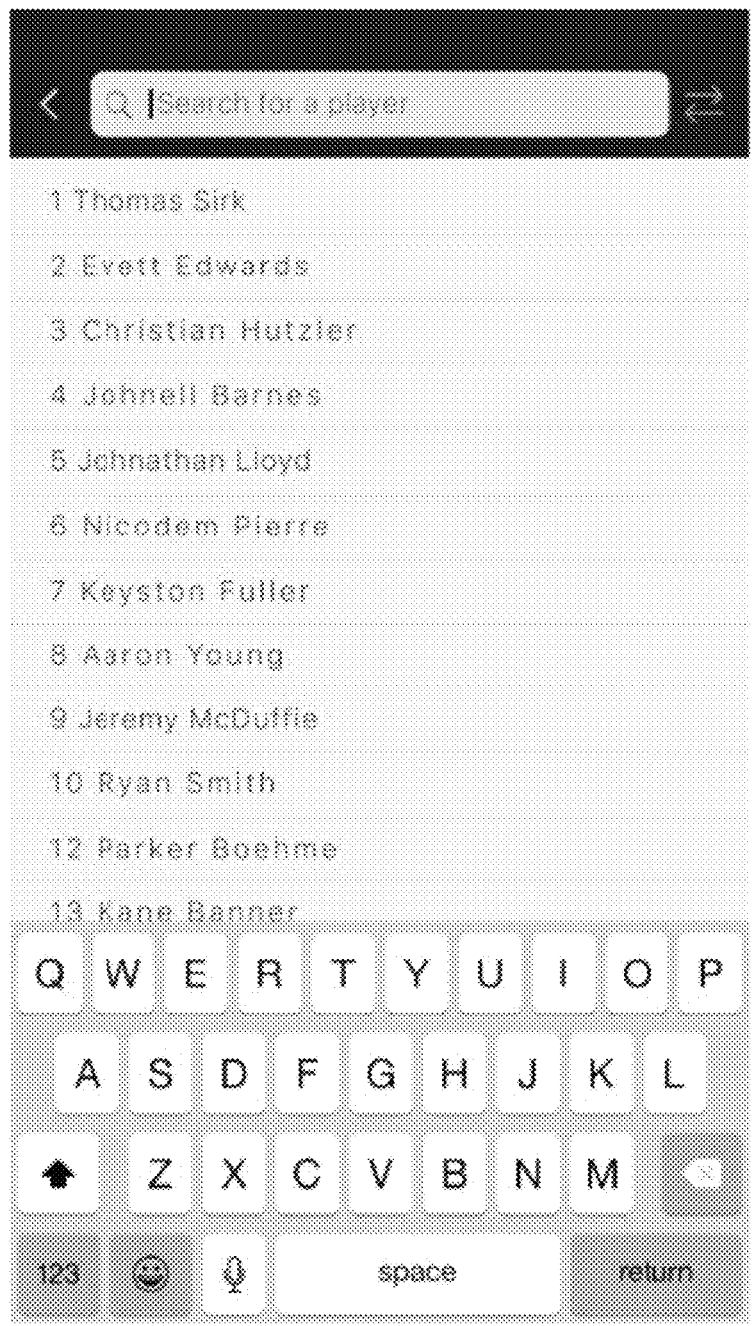
FIG. 53 is a screenshot for searching for a player.

FIG. 53 is a screenshot for searching for a player.

Figure 54:
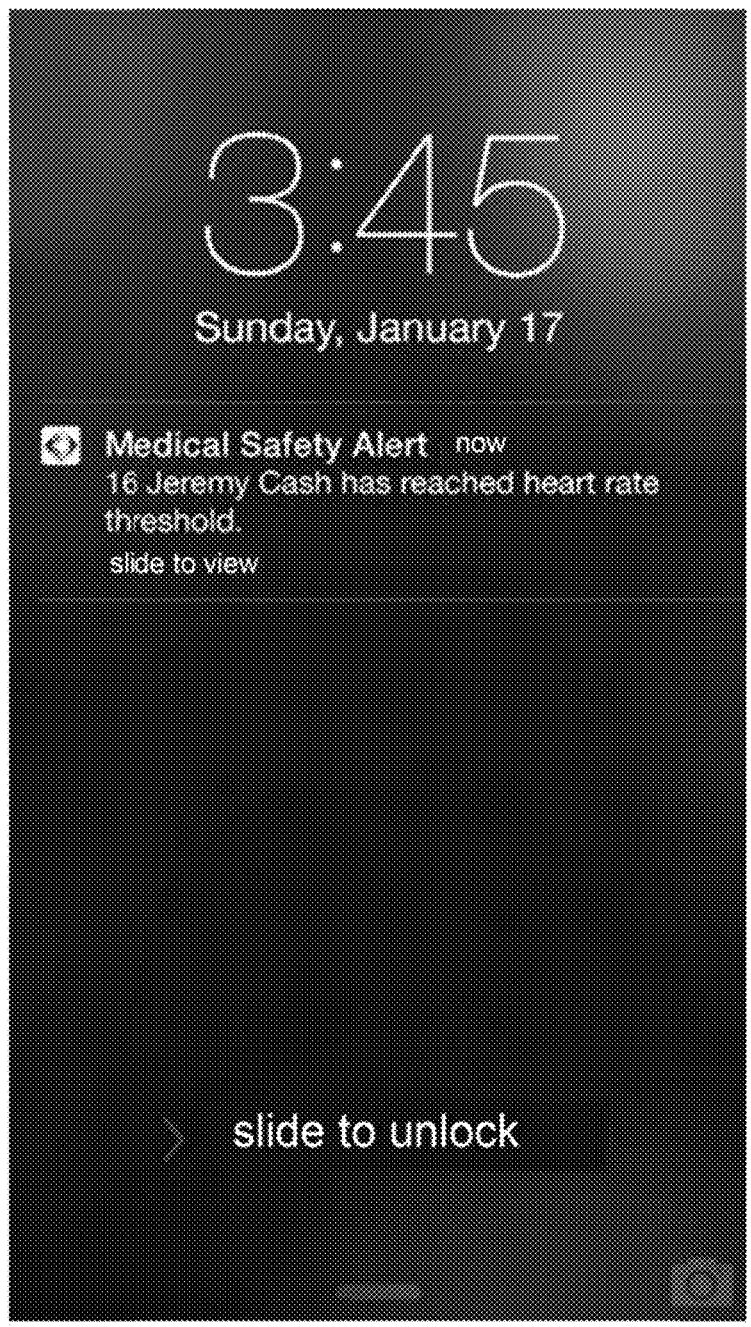
FIG. 54 is a medical safety alert received over a mobile phone showing player No. 16 has reached heart rate threshold.

FIG. 54 is a medical safety alert received over a mobile phone showing player No. 16 has reached heart rate threshold.

Figure 55:
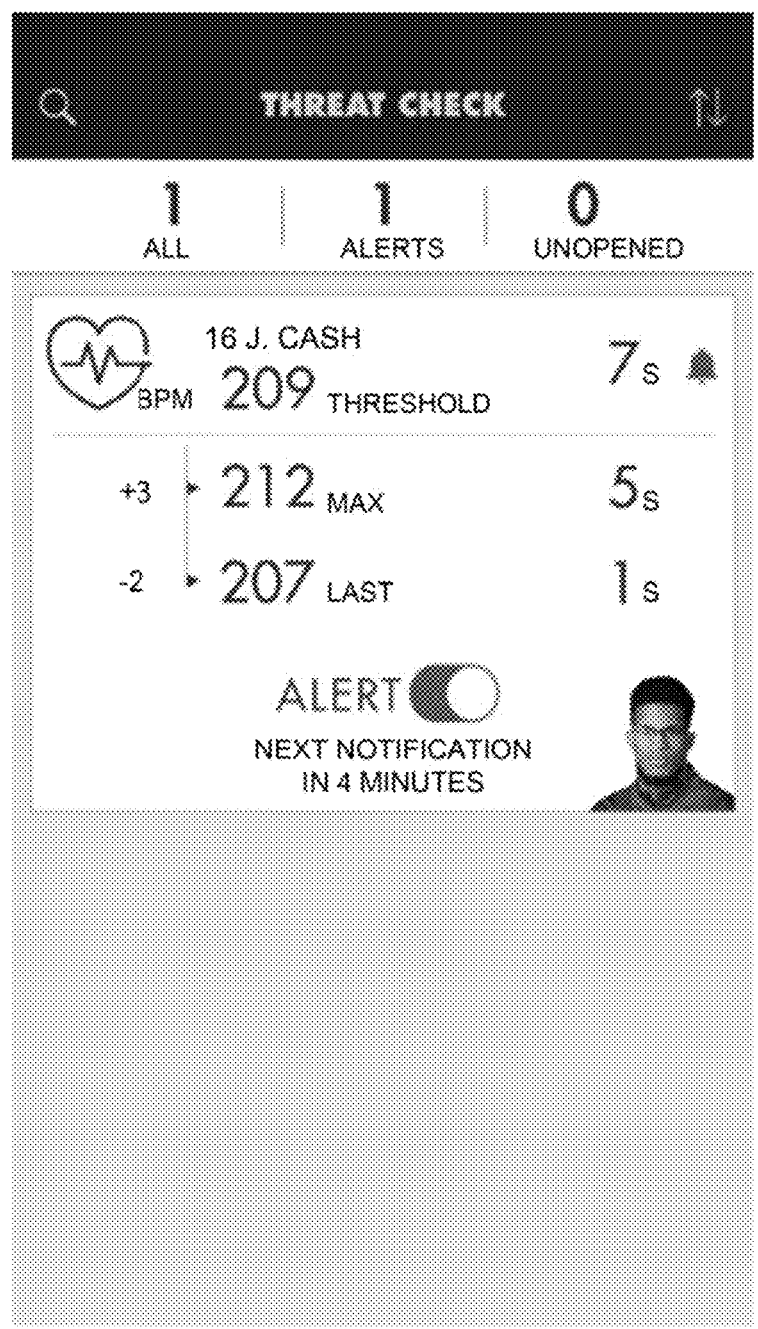
FIG. 55 is a screenshot for another embodiment of an application program displaying heart rate level is above threshold for player No. 16.

Another embodiment of a medical safety app is shown in FIG. 55. FIG. 55 is a screenshot displaying heart rate level is above threshold for a player. The heart rate is illustrated on a vertical axis, where the relative value to the threshold is shown on the left and the absolute heart rate value is shown the right. The time period is shown on the far right side. For player No. 16, the threshold value is 209 BPM. His heart rate is 207 BPM at the last 1 s, which is below threshold 209 BPM.

Figure 56:
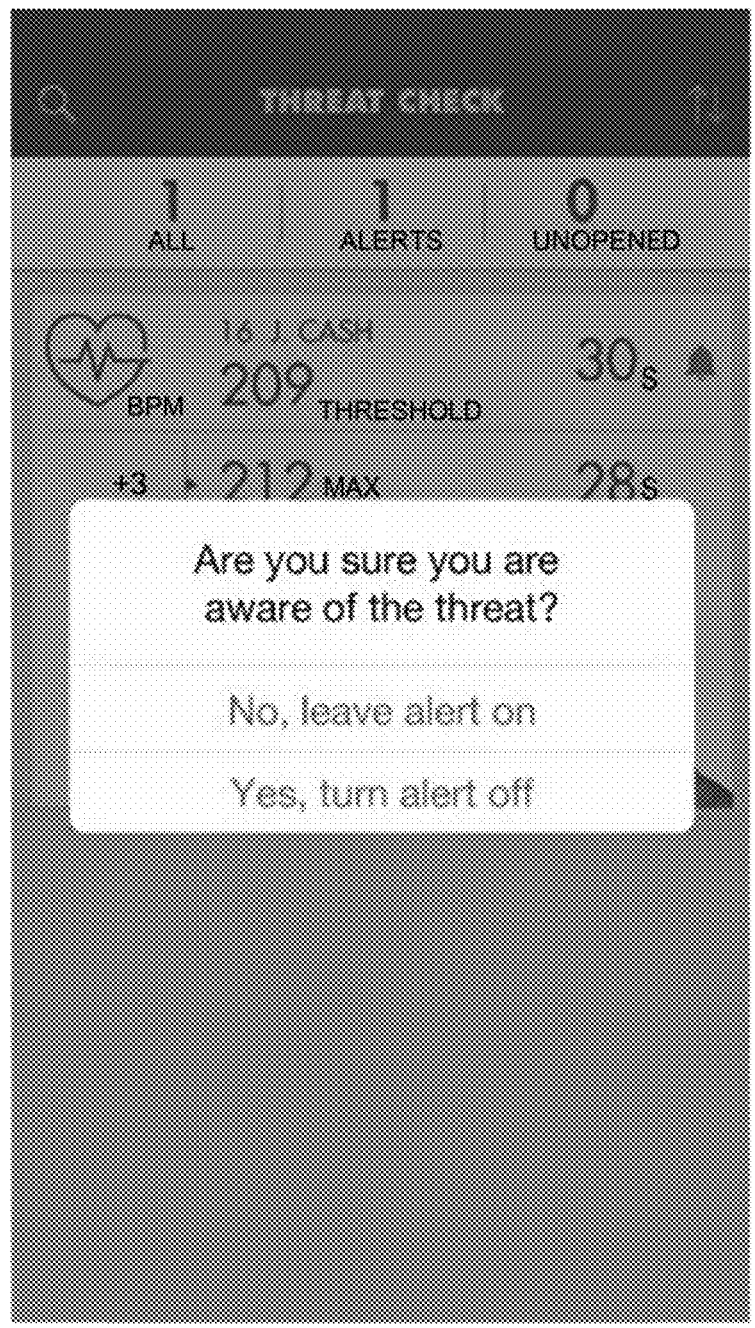
FIG. 56 is a screenshot displaying options of leaving alert one and turning alert off for player 16.
Figure 57:
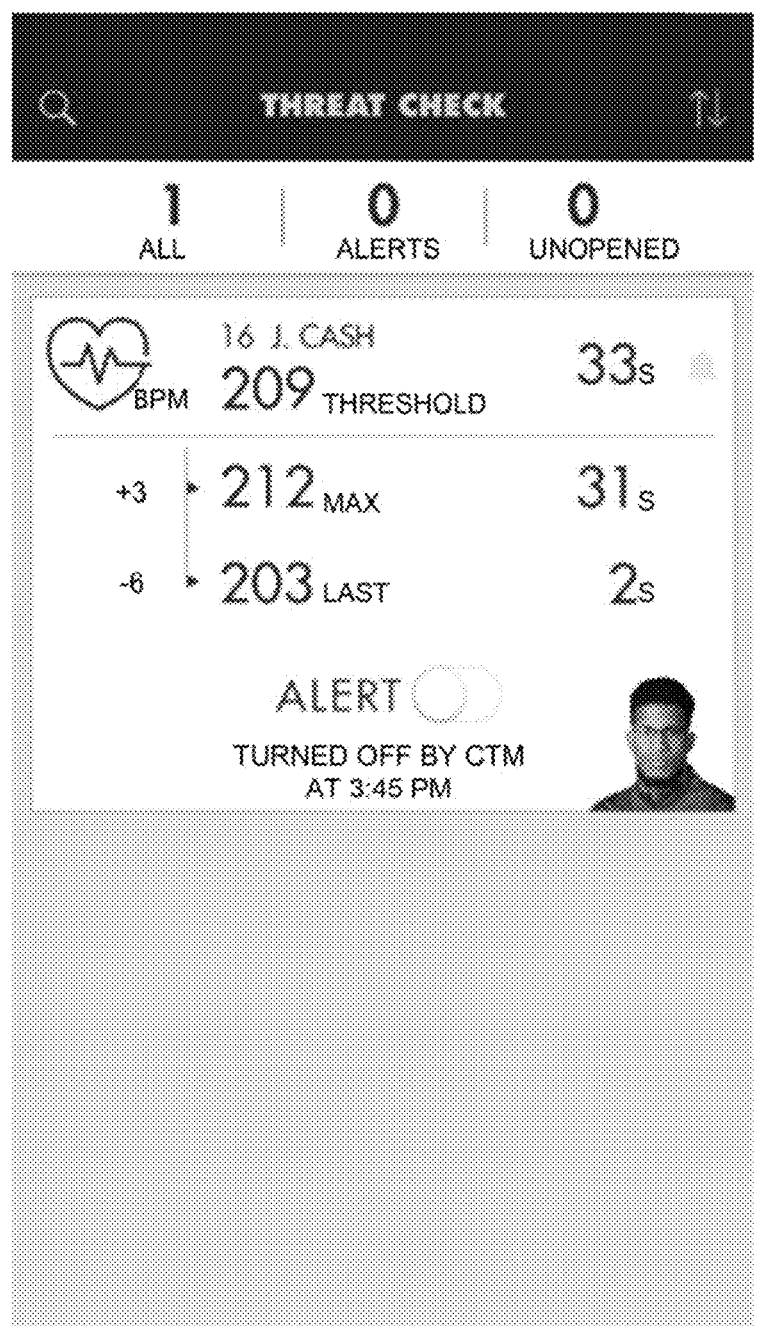
FIG. 57 is a screenshot displaying a medical safety alert is off for player No. 16.

FIG. 56 is a screenshot displaying options of leaving alert one and turning alert off for player 16. FIG. 57 is a screenshot displaying a medical safety alert is off for player No. 16.

Figure 58:
FIG. 58 is a screenshot for receiving a medical alert that player No. 1 has reached heart rate threshold.
Figure 59:
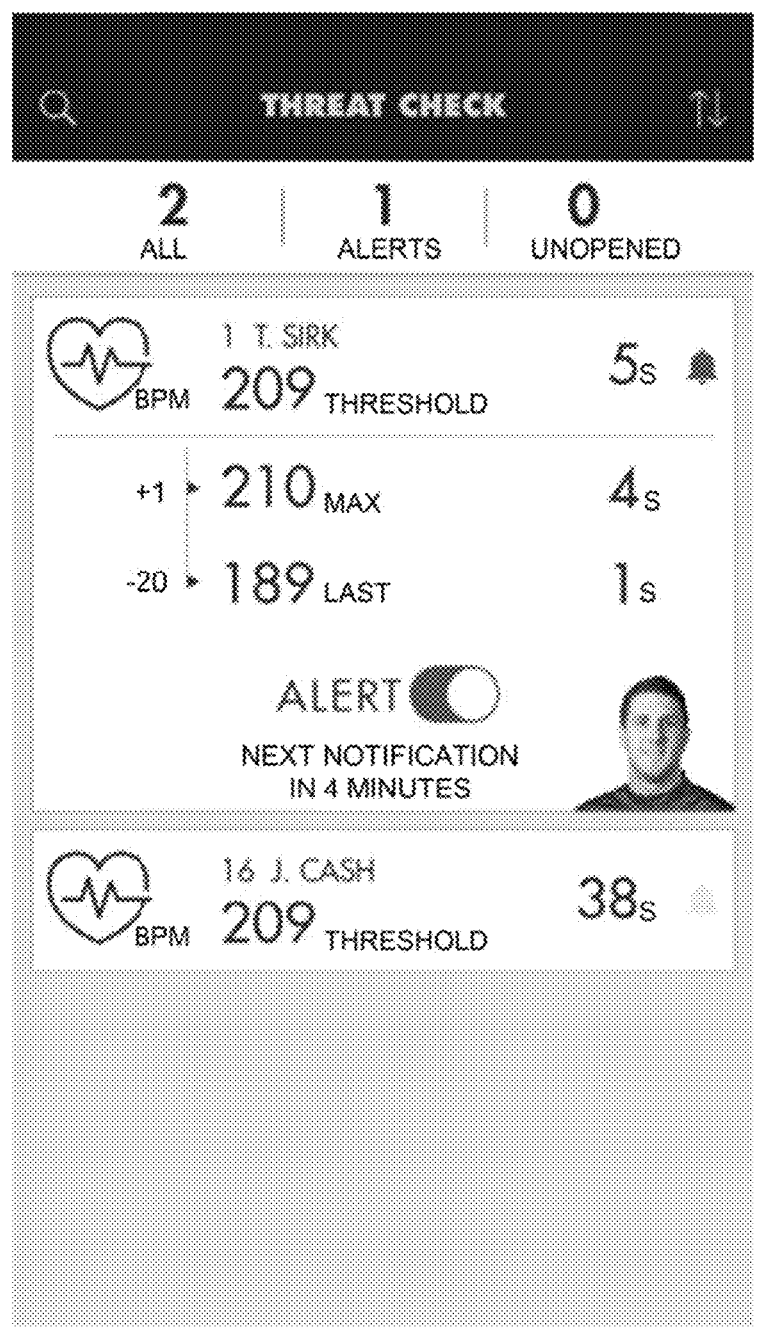
FIG. 59 is a screenshot displaying the medical alert for player No. 1.

FIG. 58 is a screenshot for receiving a medical alert that player No. 1 has reached heart rate threshold. FIG. 59 is a screenshot displaying the medical alert for player No. 1. At the last 1 s, his heart rate is 189 BPM, which is below threshold 209 BPM.

Figure 60:
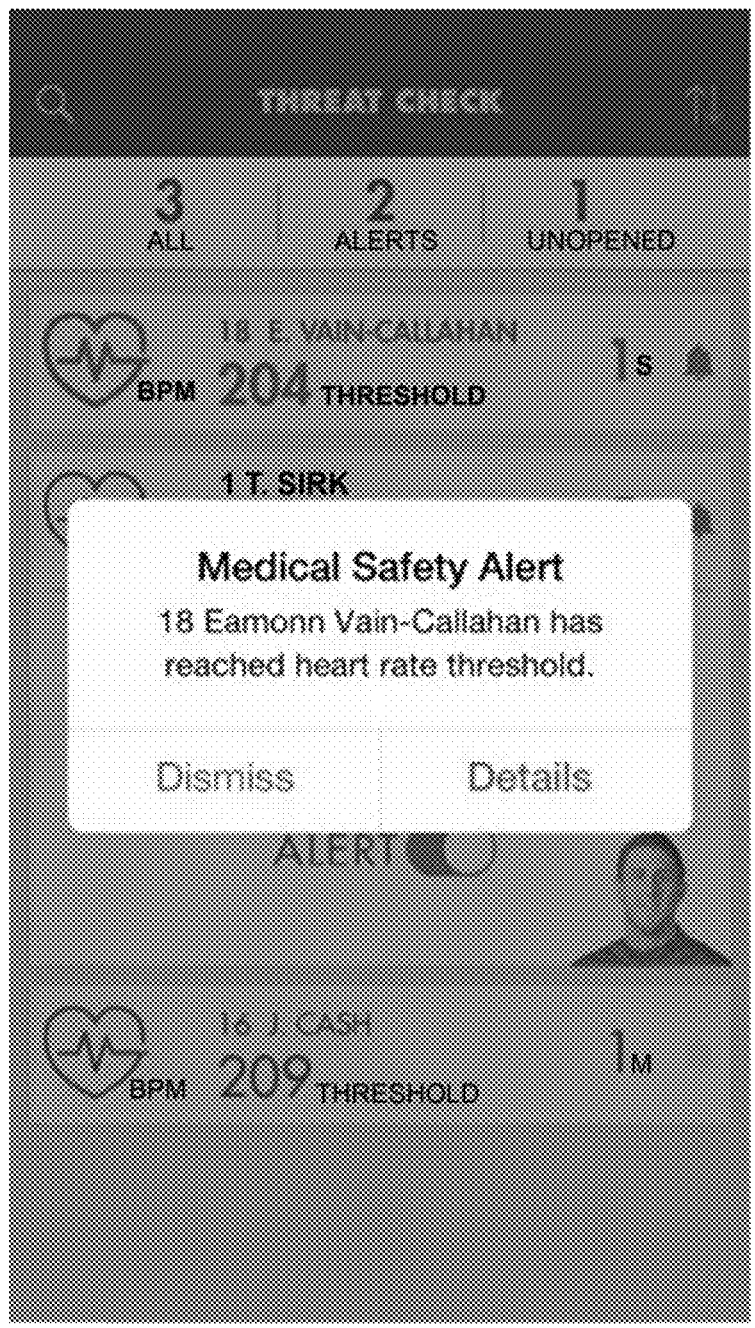
FIG. 60 is a screenshot for receiving a medical alert that player No. 18 has reached heart rate threshold.
Figure 61:
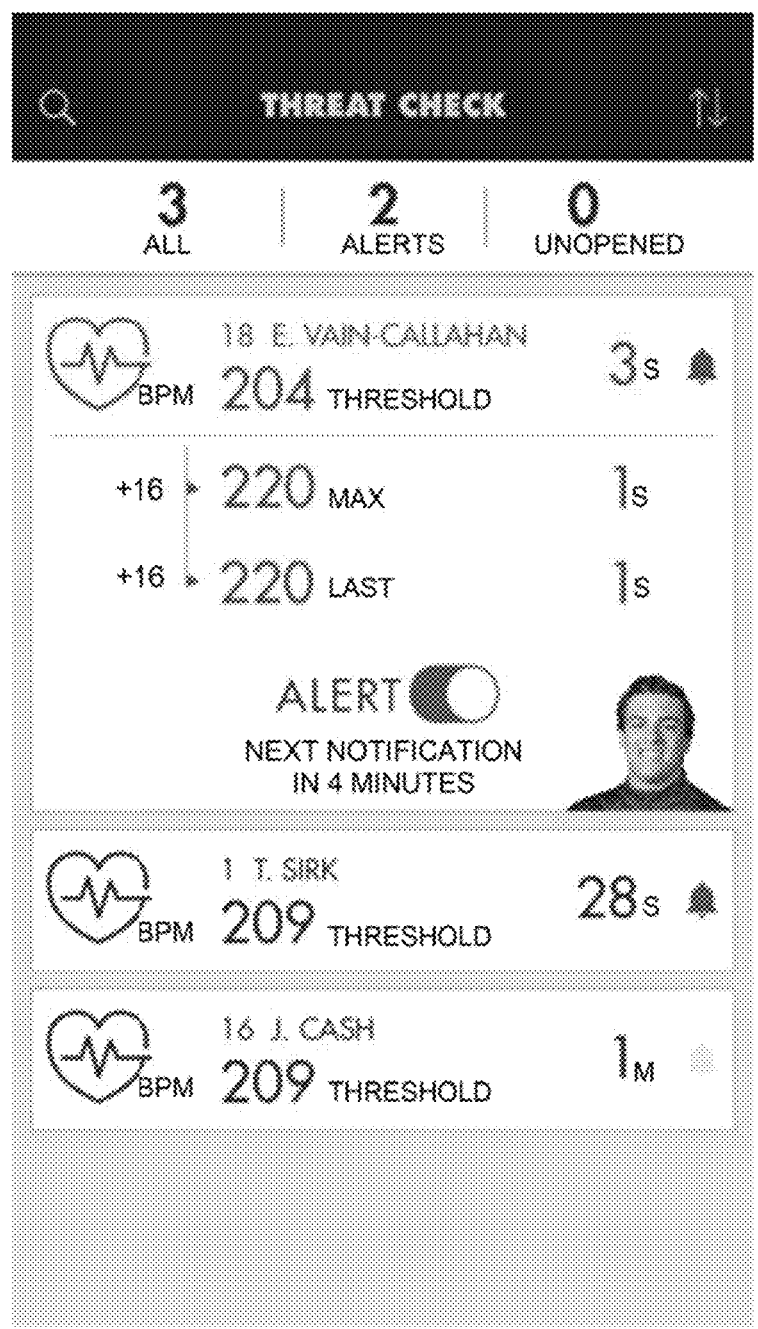
FIG. 61 is a screenshot displaying the medical alert for player No. 18.
Figure 62:
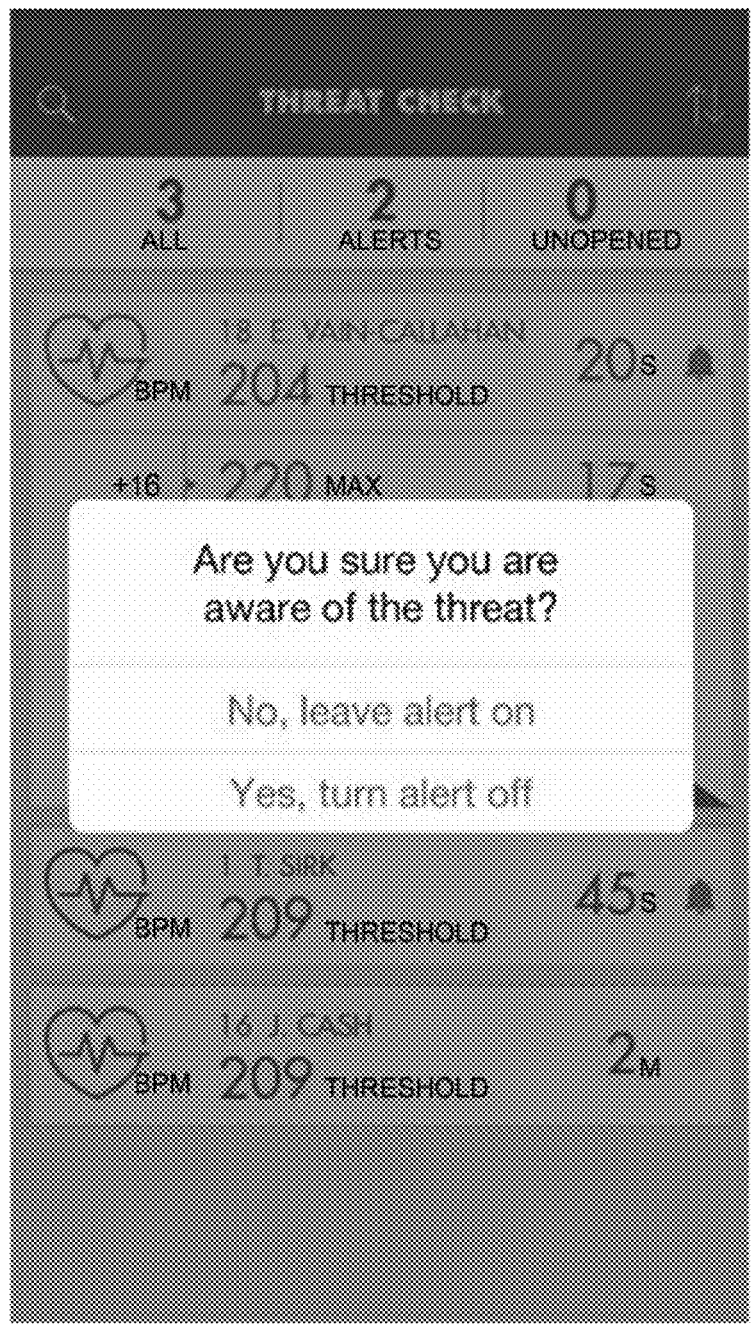
FIG. 62 is a screenshot displaying options of leaving alert one and turning alert off for player No. 18.
Figure 63:
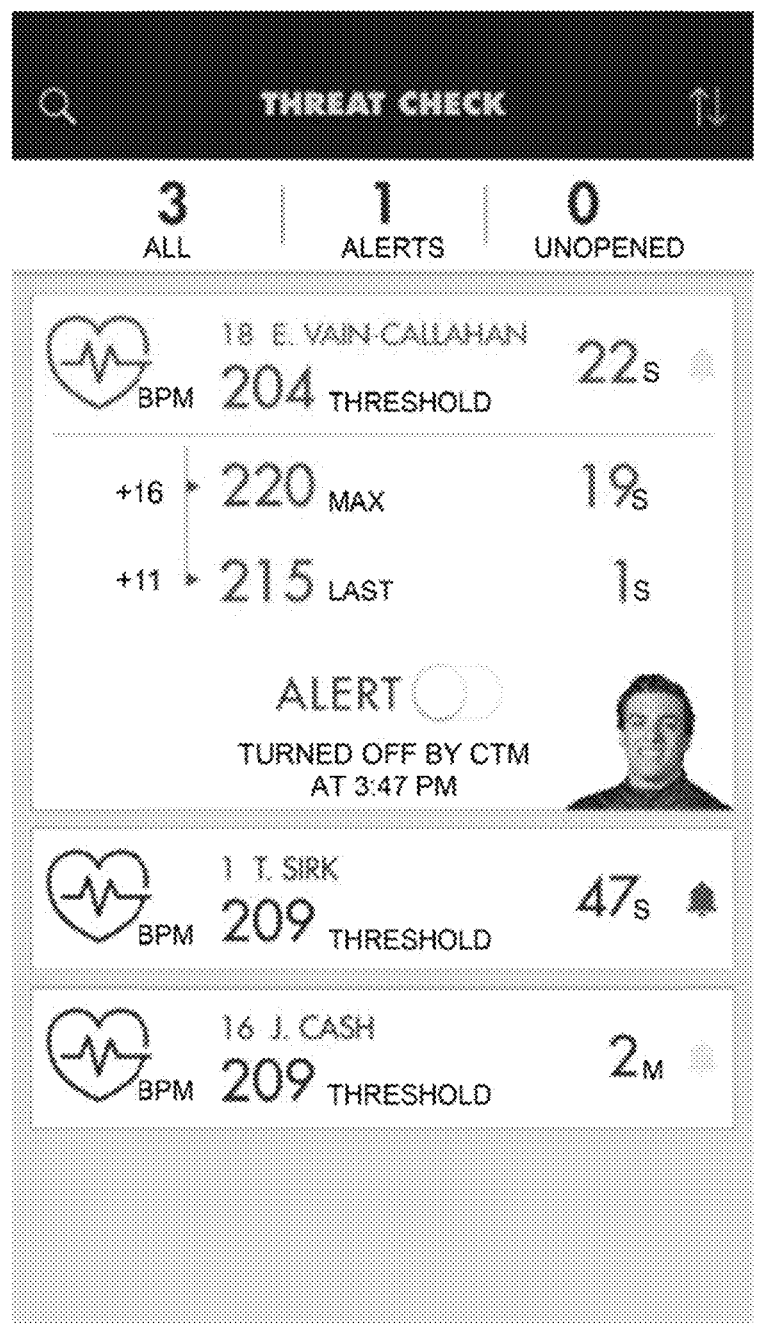
FIG. 63 is a screenshot displaying a medical safety alert is off for player No. 18.
Figure 64:
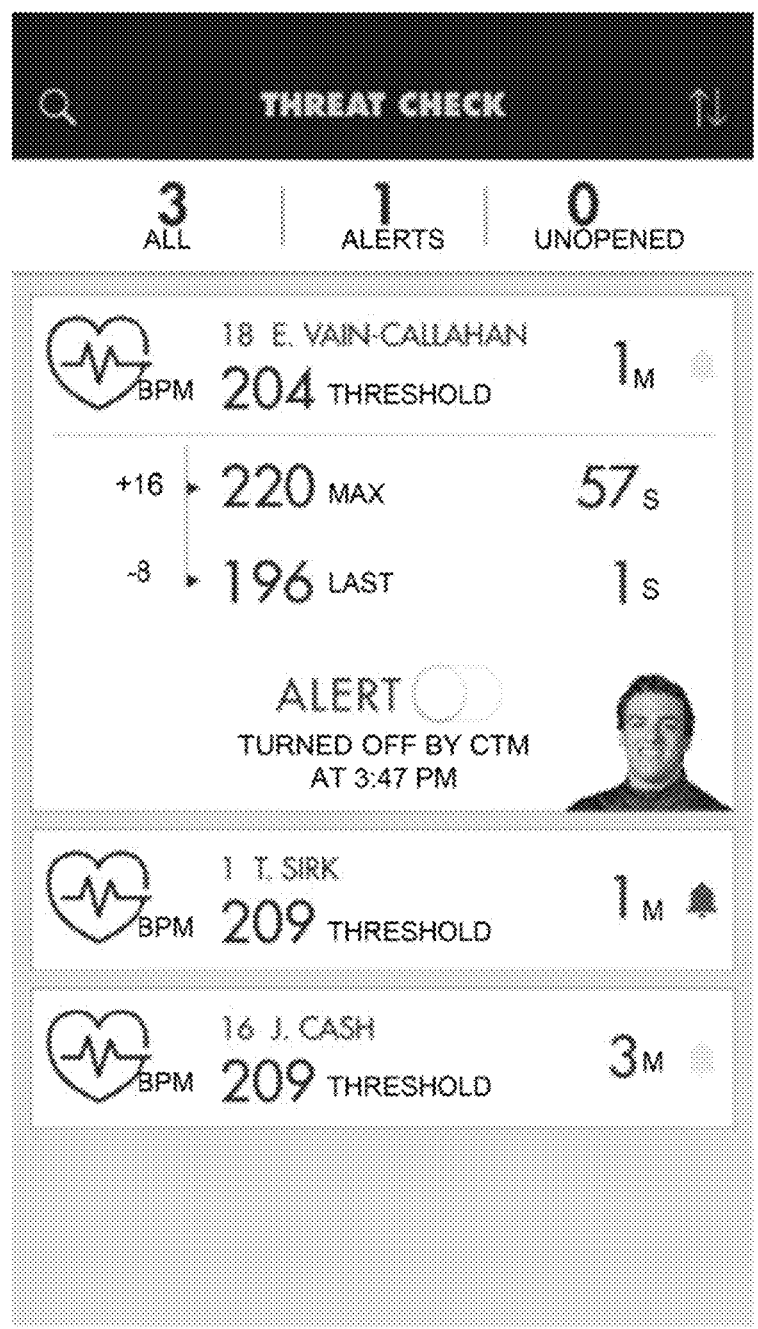
FIG. 64 is a screenshot displaying the heart rate for player No. 18 is below threshold.

FIG. 60 is a screenshot for receiving a medical alert that player No. 18 has reached heart rate threshold. FIG. 61 is a screenshot displaying the medical alert for player No. 18. FIG. 62 is a screenshot displaying options of leaving alert one and turning alert off for player No. 18. FIG. 63 is a screenshot displaying a medical safety alert is off for player No. 18. FIG. 64 is a screenshot displaying the heart rate for player No. 18 is 196 BPM, which is below threshold 204 BPM at the last 1 s.

Figure 65:
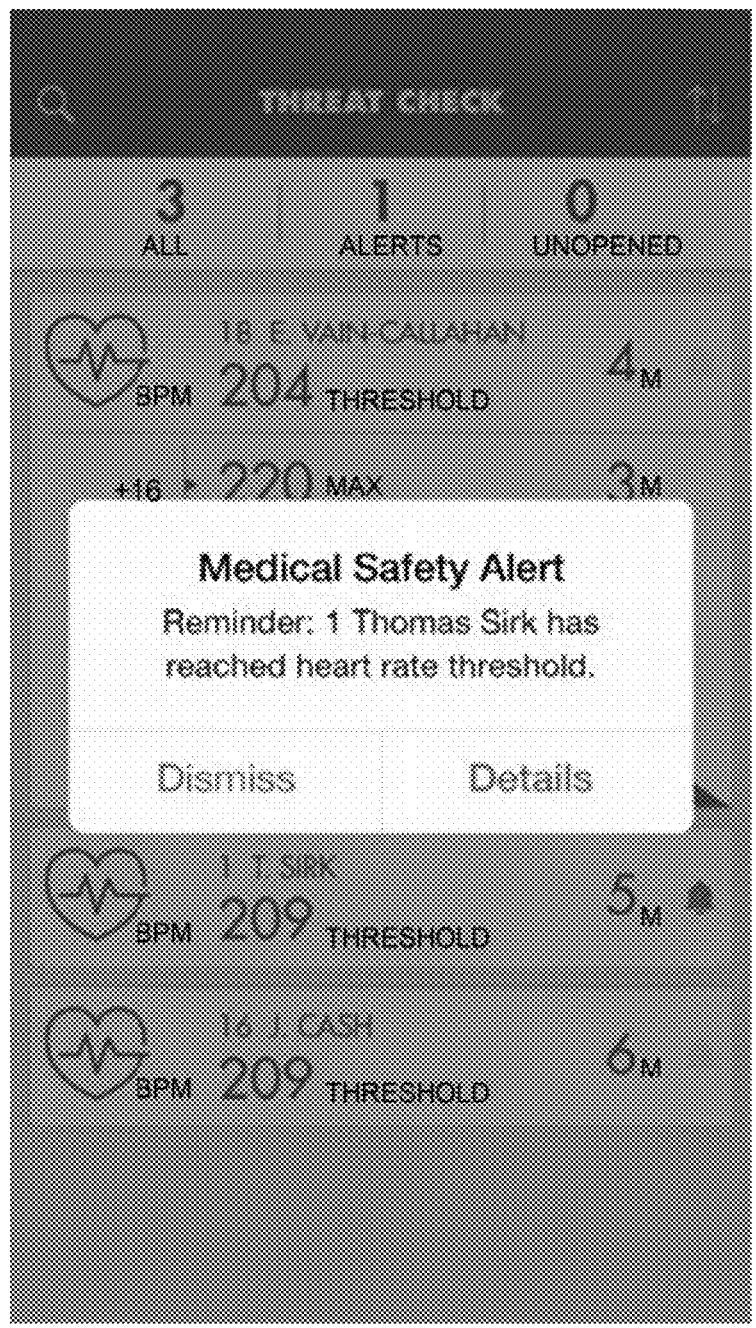
FIG. 65 is a screenshot displaying player No. 1 has reached heart rate threshold.
Figure 66:
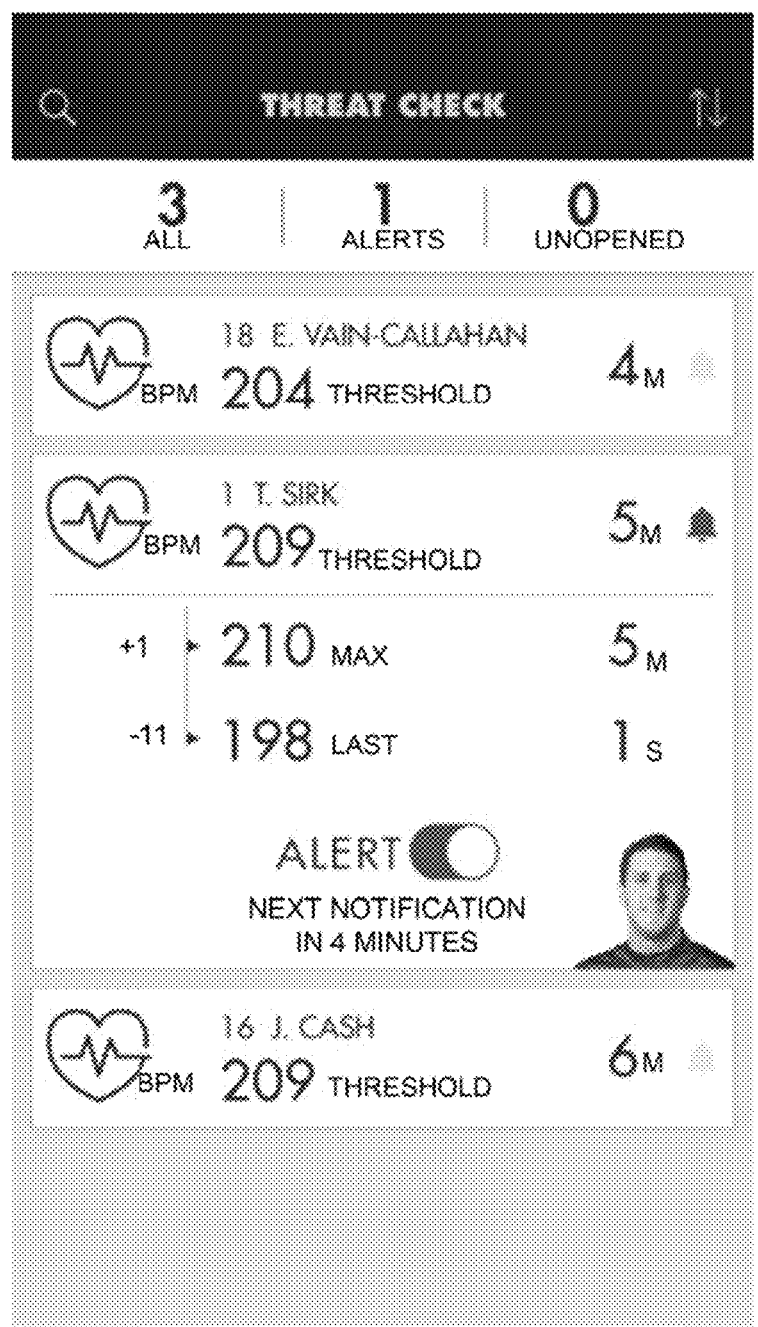
FIG. 66 is a screenshot displayer the heart rate of player No. 1 is below threshold.
Figure 67:
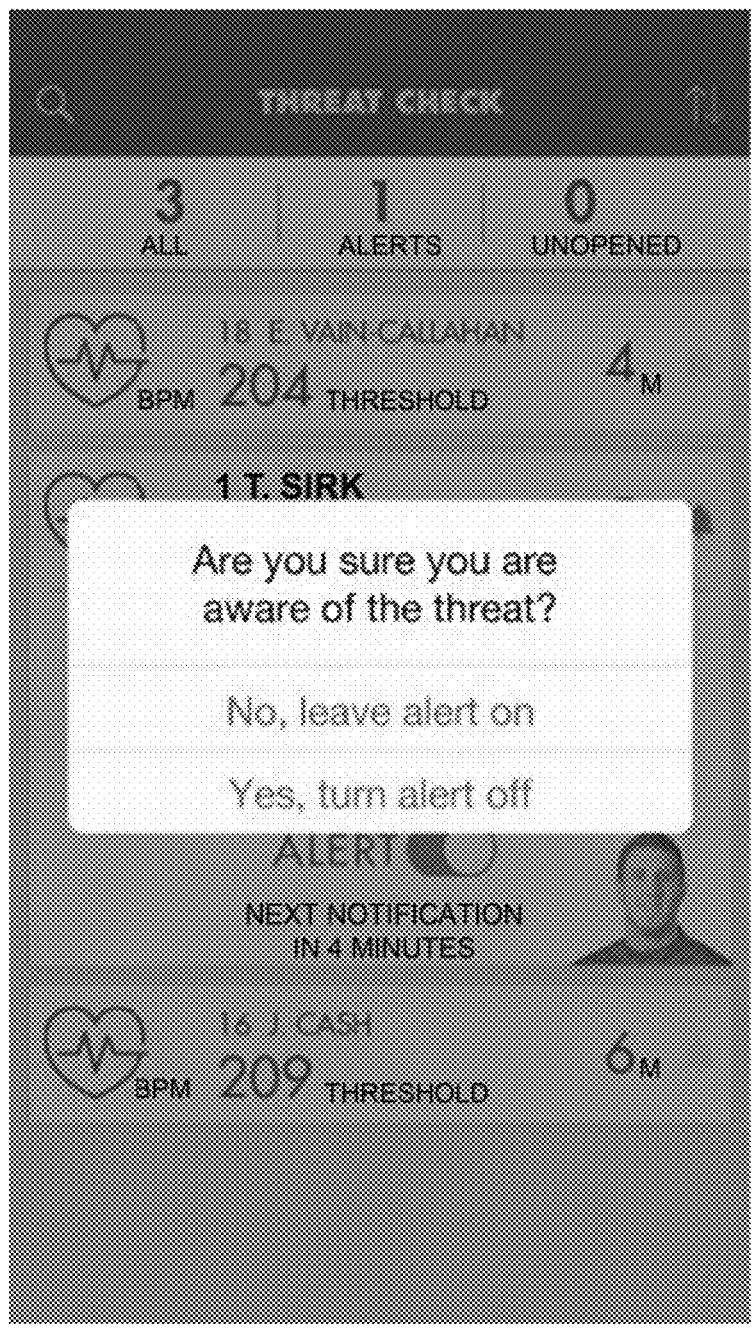
FIG. 67 is a screenshot displaying options of leaving alert one and turning alert off for player No. 1.
Figure 68:
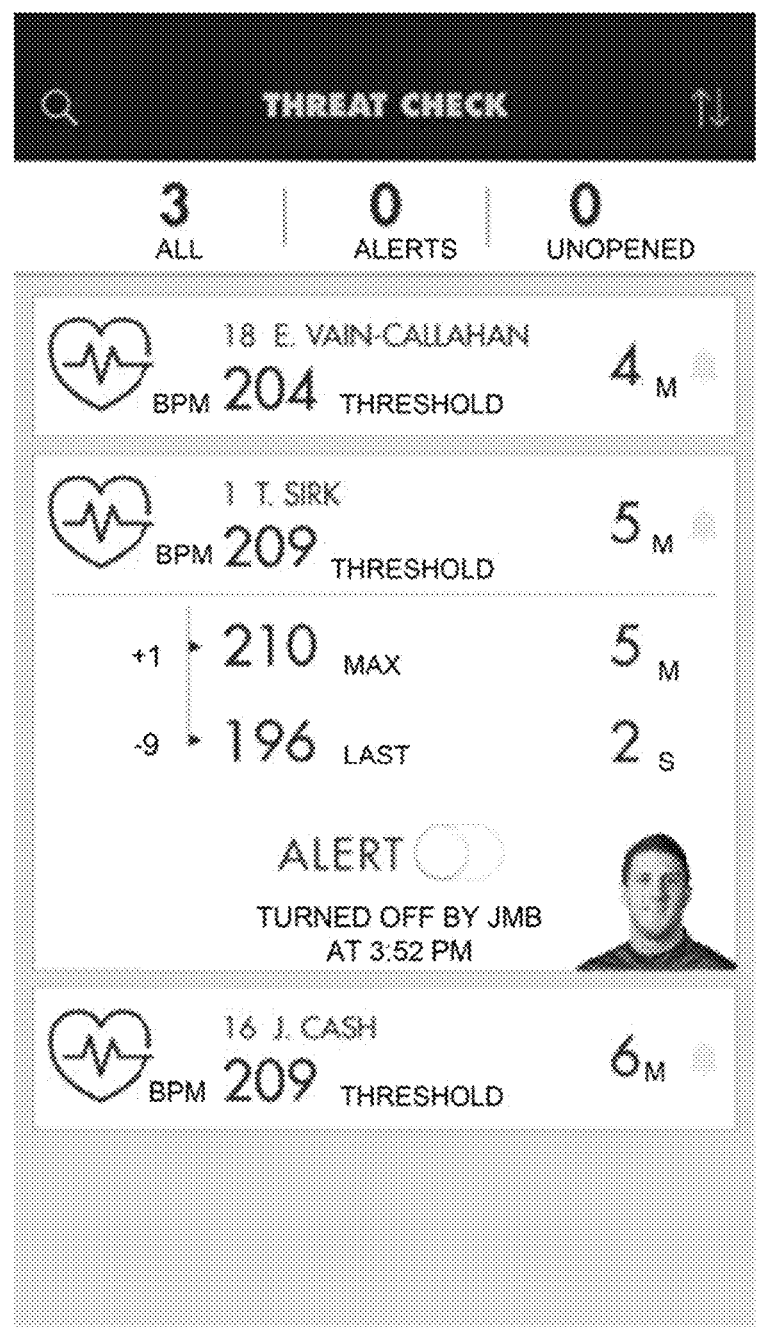
FIG. 68 is a screenshot displaying a medical safety alert is off for player No. 1.

FIG. 65 is a screenshot displaying player No. 1 has reached heart rate threshold. FIG. 66 is a screenshot displayer the heart rate of player No. 1 is 198 BPM, which is below threshold 209 BPM, at the last 1 s. FIG. 67 is a screenshot displaying options of leaving alert one and turning alert off for player No. 1. FIG. 68 is a screenshot displaying a medical safety alert is off for player No. 1.

Figure 69:
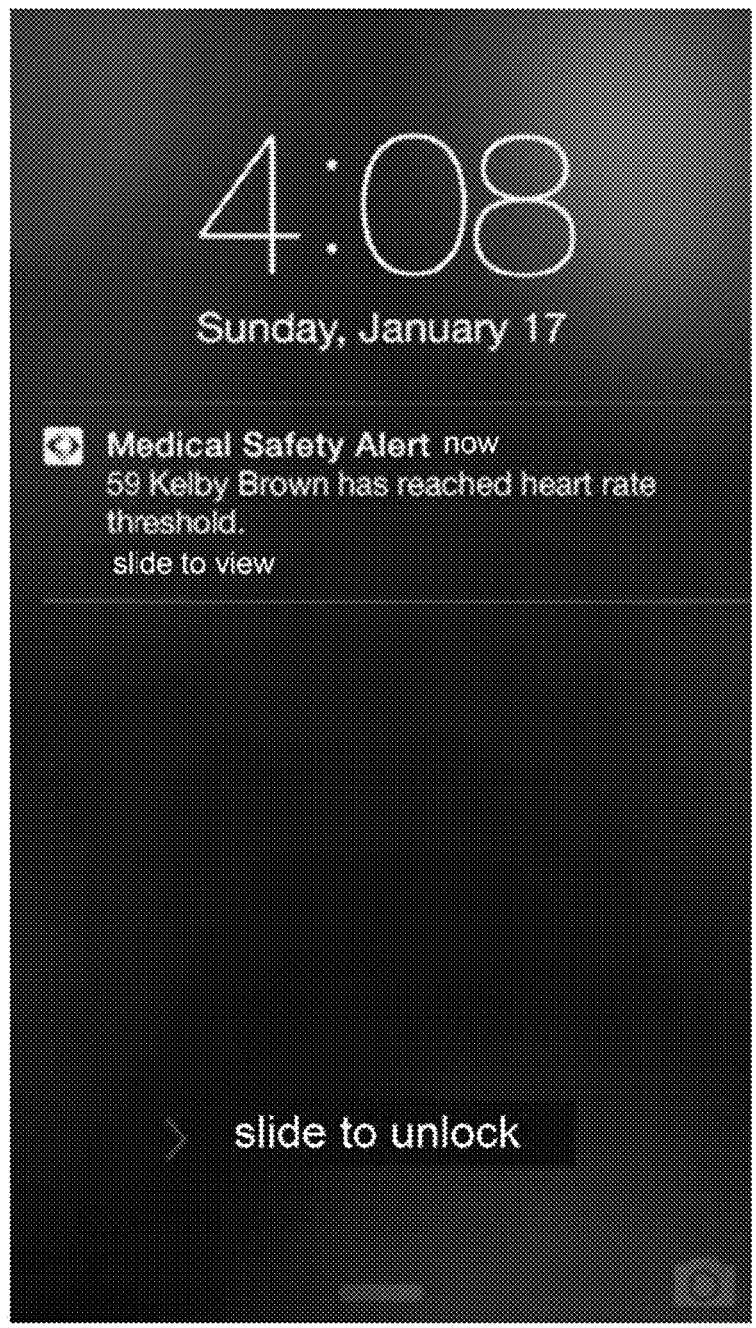
FIG. 69 is a screenshot for one medical safety alert received over a mobile phone showing player No. 59 has reached heart rate threshold.
Figure 70:
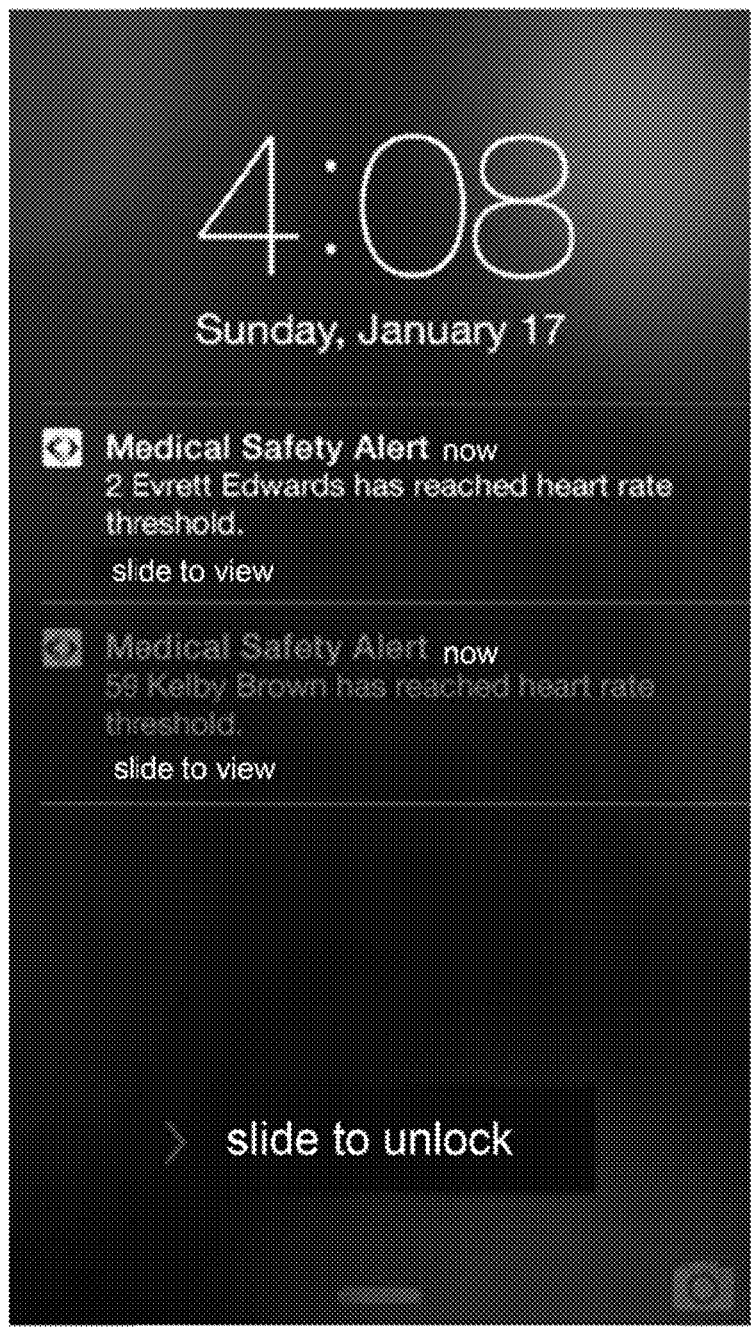
FIG. 70 is a screenshot for two medical safety alerts received over a mobile phone showing player No. 59 has reached heart rate threshold and player No. 2 has reached heart rate threshold.
Figure 71:
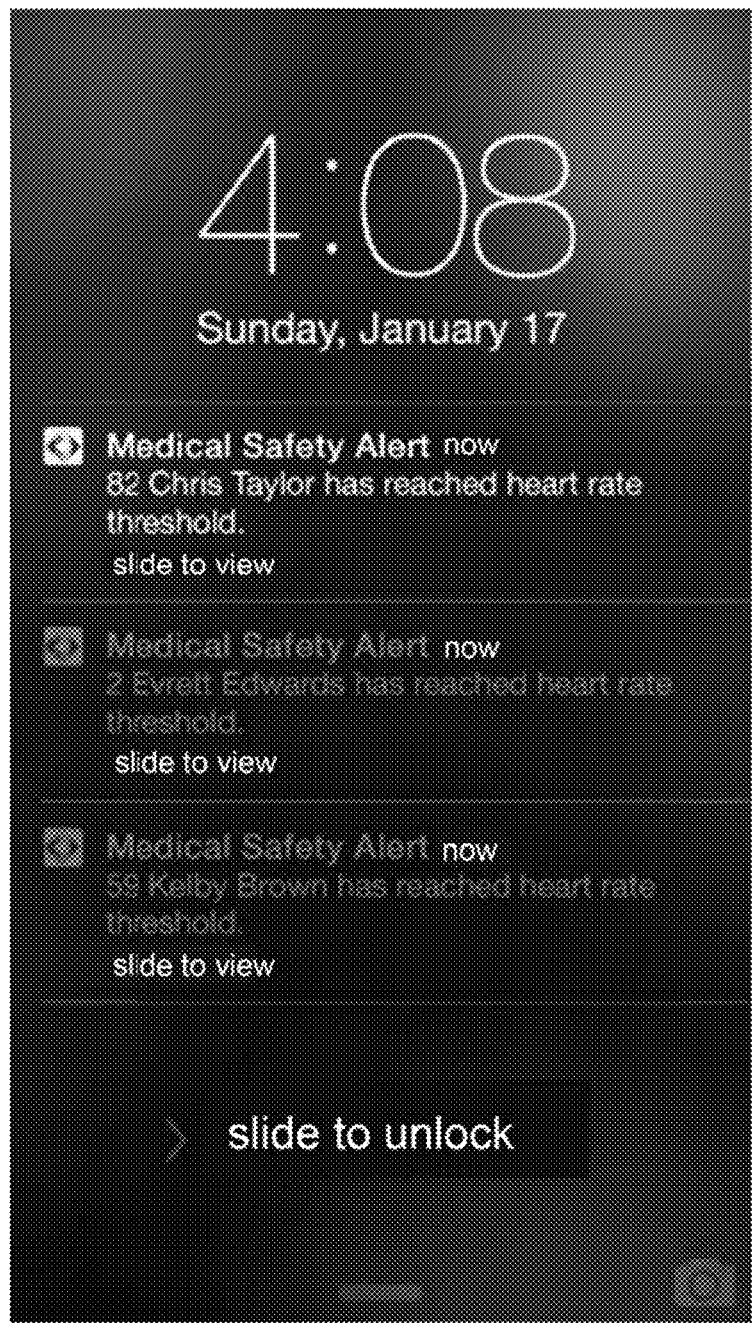
FIG. 71 is a screenshot for three medical safety alerts received over a mobile phone showing player No. 59 has reached heart rate threshold and player No. 2 has reached heart rate threshold and player No. 82 reached heart rate threshold.

FIG. 69 is a screenshot for one medical safety alert received over a mobile phone showing player No. 59 has reached heart rate threshold. FIG. 70 is a screenshot for two medical safety alerts received over a mobile phone showing player No. 59 has reached heart rate threshold and player No. 2 has reached heart rate threshold. FIG. 71 is a screenshot for three medical safety alerts received over a mobile phone showing player No. 59 has reached heart rate threshold and player No. 2 has reached heart rate threshold and player No. 82 reached heart rate threshold.

Figure 72:
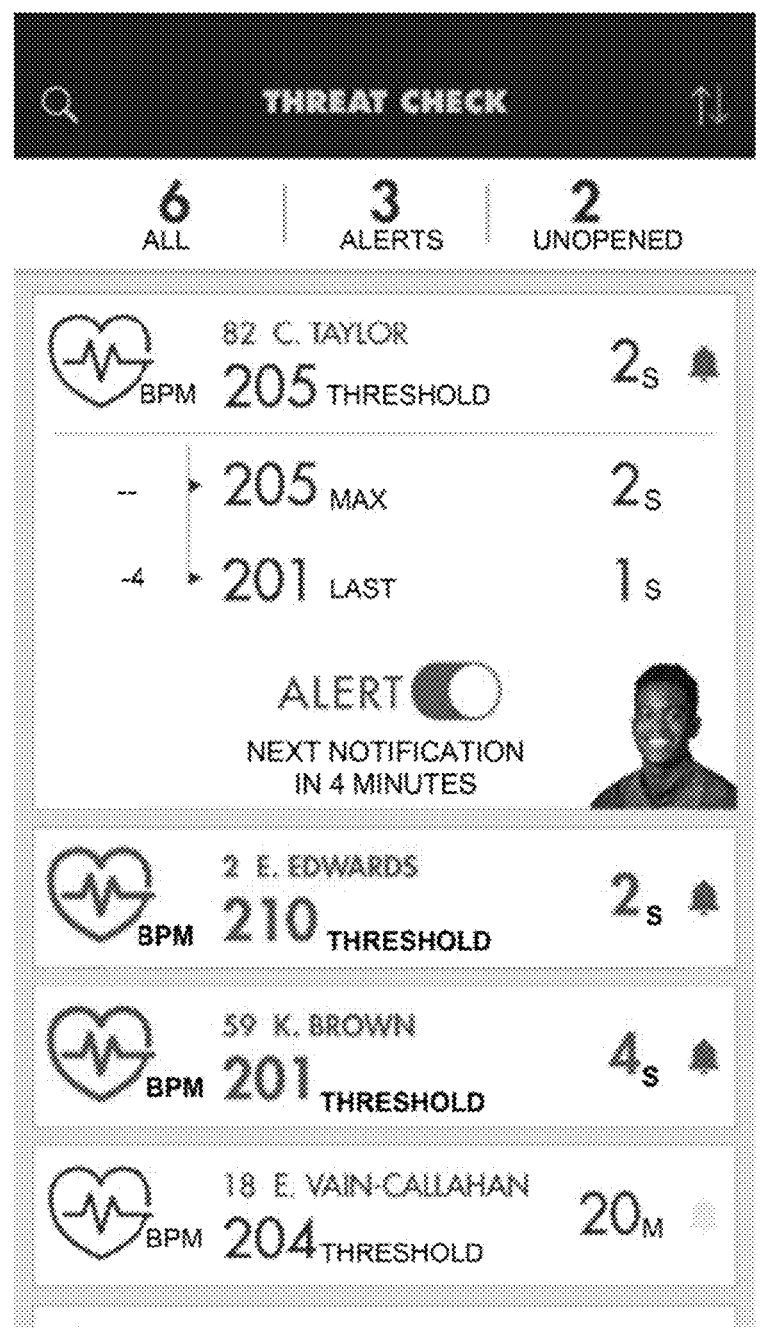
FIG. 72 is a screenshot displaying player No. 82 is below heart rate threshold.

FIG. 72 is a screenshot displaying player No. 82 is below heart rate threshold.

Figure 73:
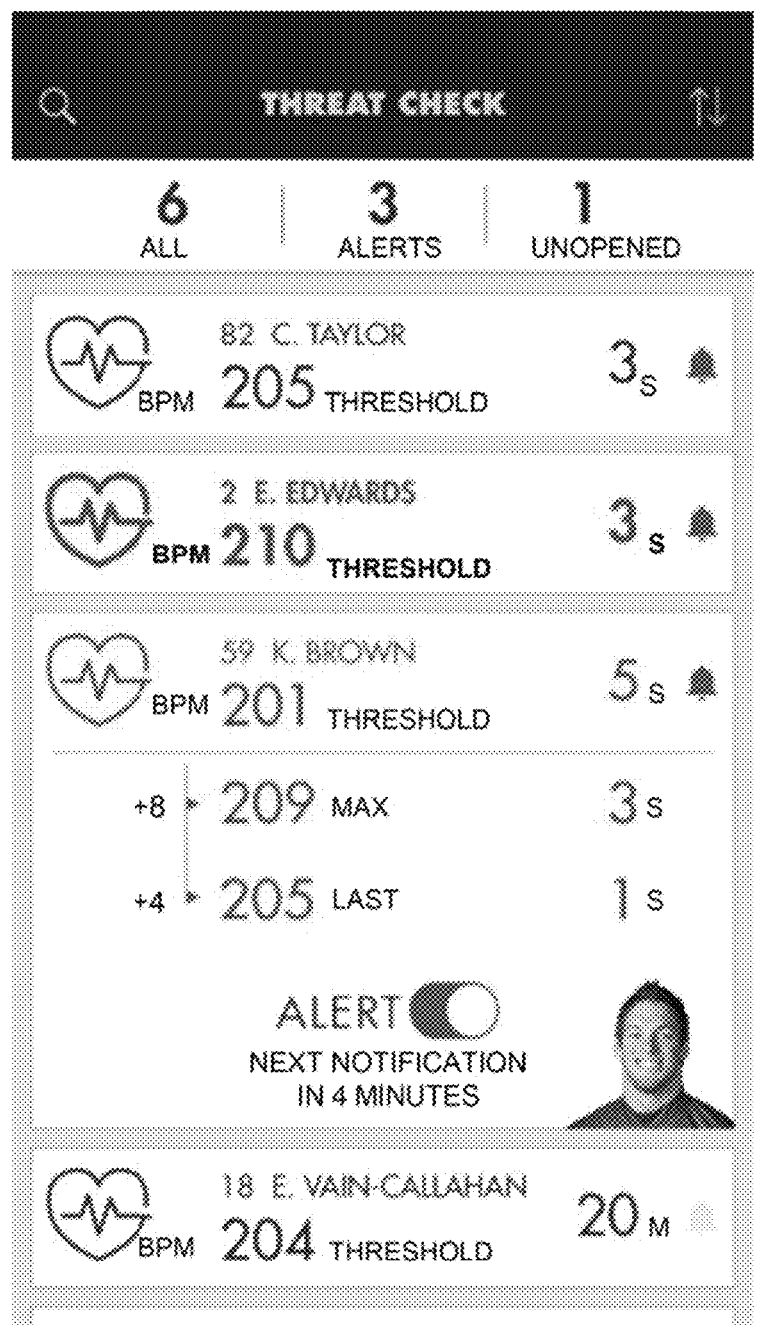
FIG. 73 is a screenshot displaying player No. 59 is above heart rate threshold.
Figure 74:
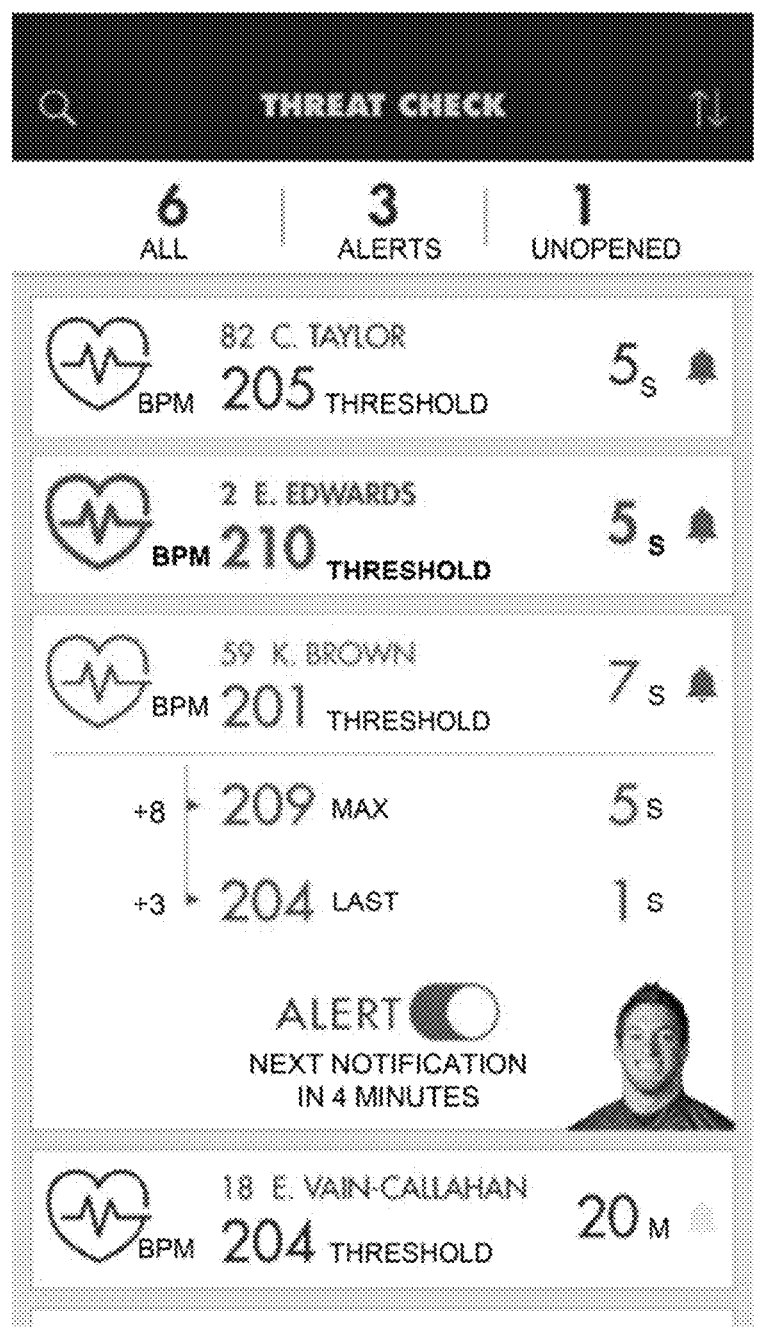
FIG. 74 is a screenshot displaying player No. 59 is above heart rate threshold.
Figure 75:
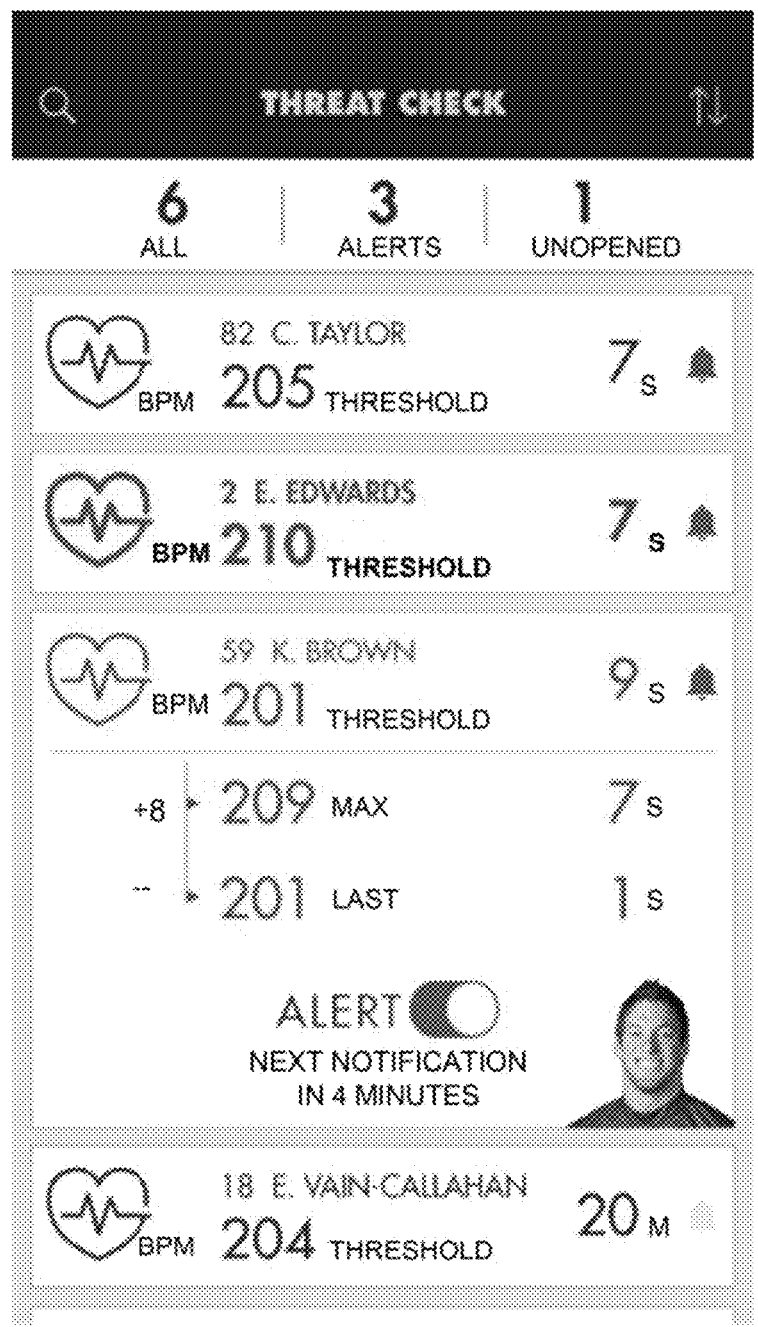
FIG. 75 is a screenshot displaying player No. 59 is above heart rate threshold.
Figure 76:
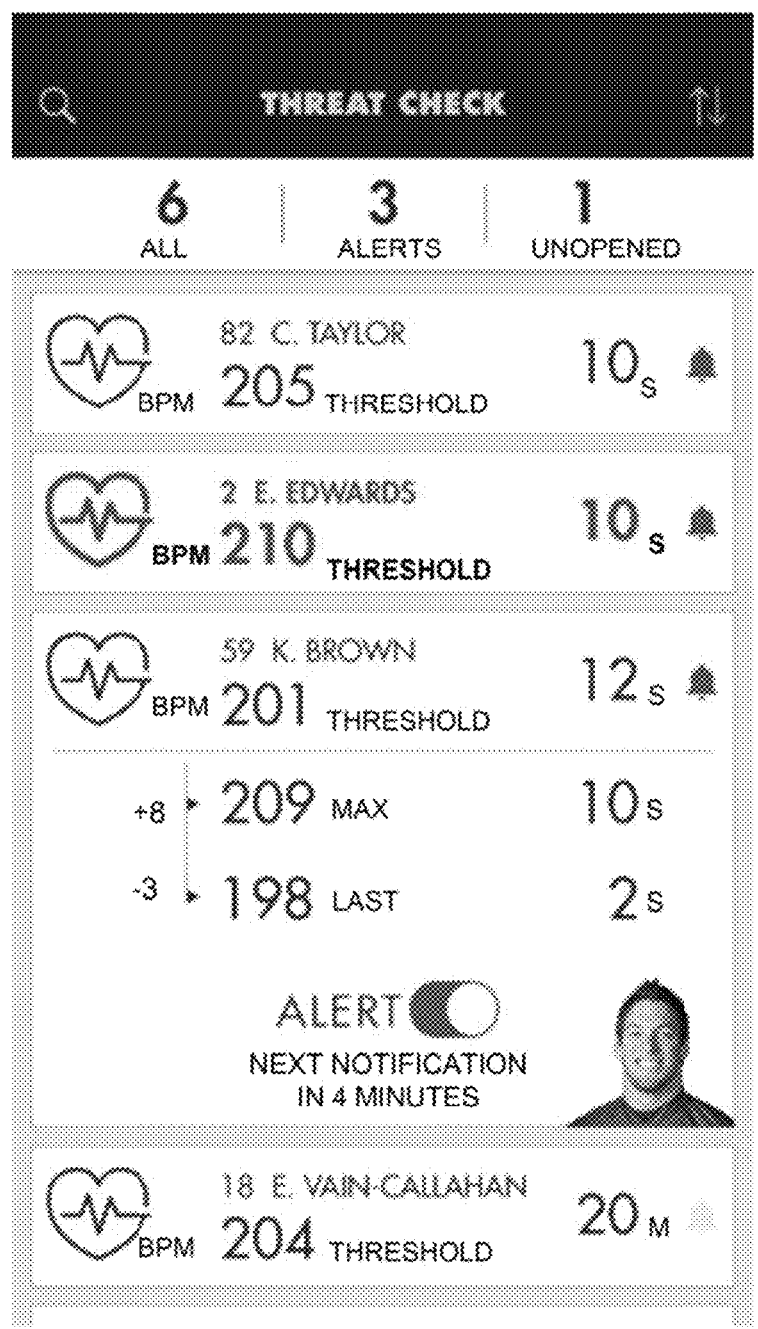
FIG. 76 is a screenshot displaying player No. 59 is below heart rate threshold.
Figure 77:
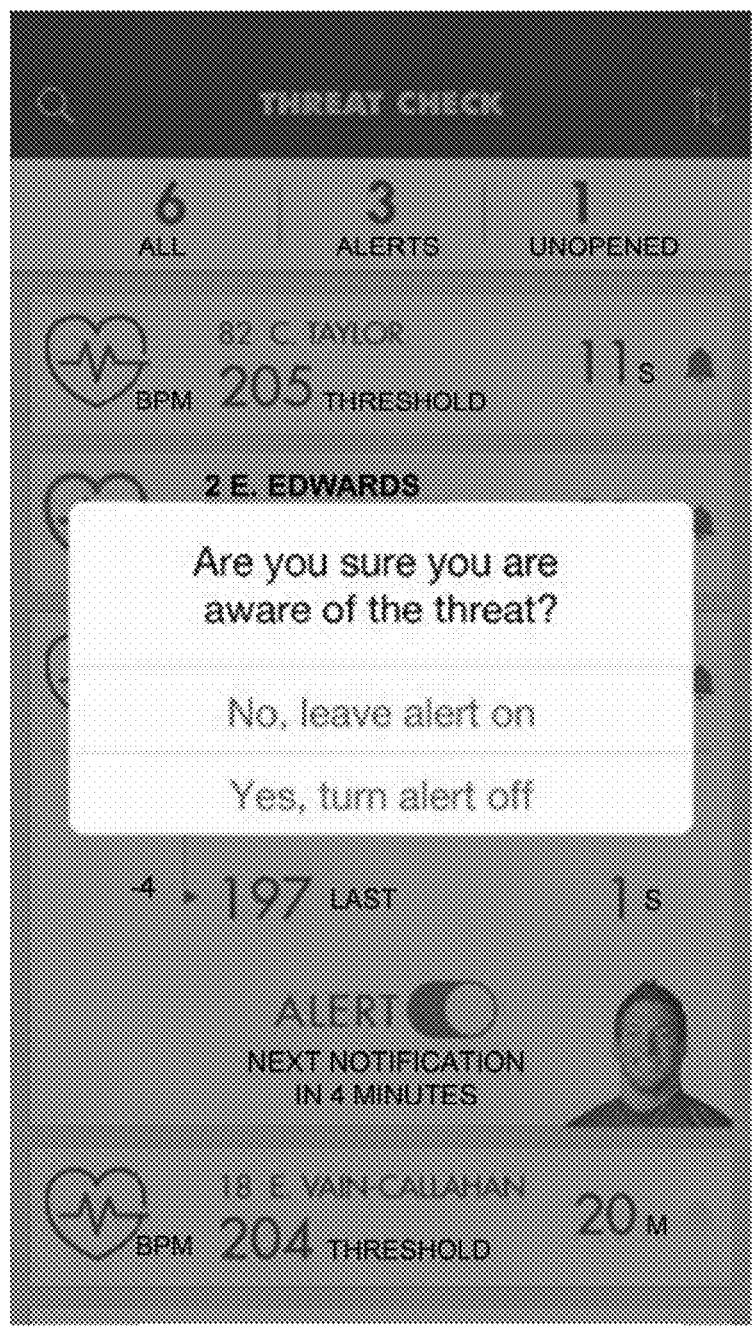
FIG. 77 is a screenshot displaying options of leaving alert one and turning alert off for player No. 59.
Figure 78:
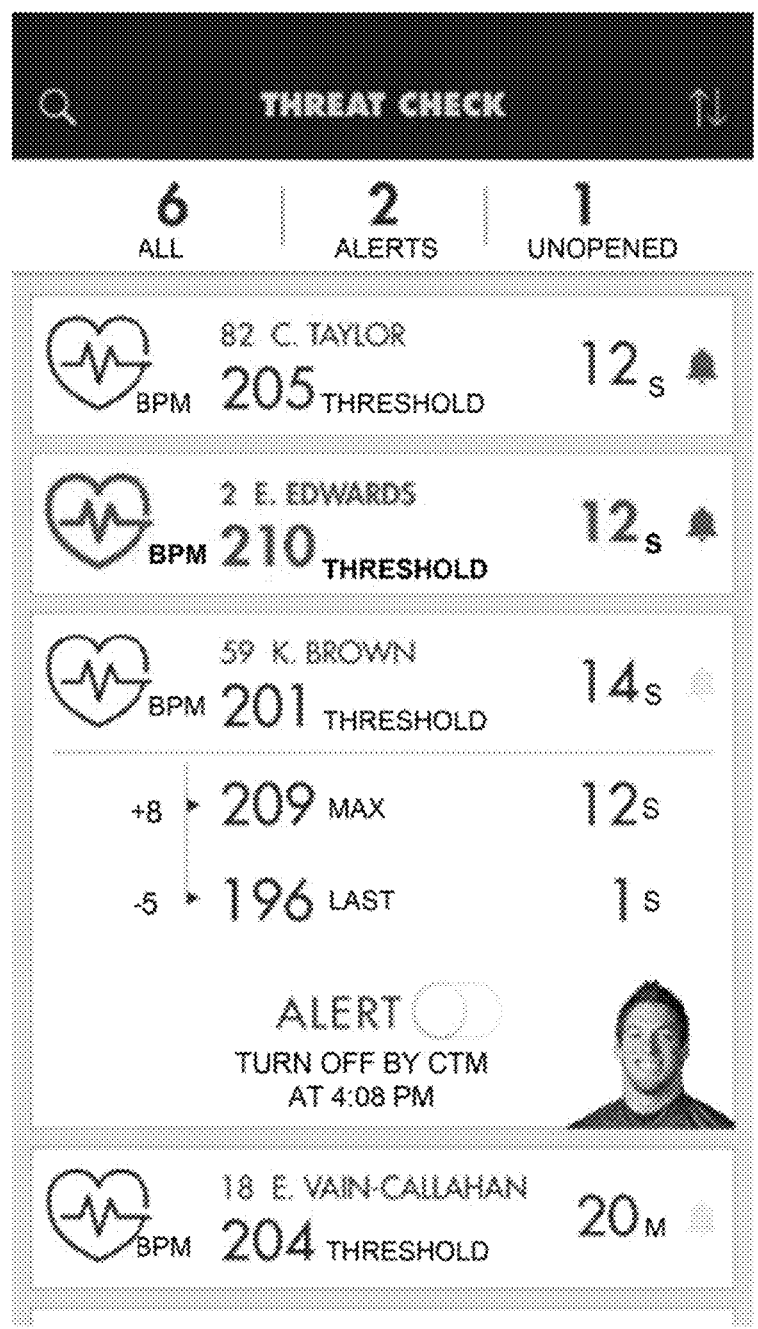
FIG. 78 is a screenshot displaying a medical safety alert is off for player No. 59.

FIGS. 73-75 are screenshots displaying player No. 59 is above heart rate threshold. FIG. 76 is a screenshot displaying player No. 59 is below heart rate threshold at the last 2 s. FIG. 77 shows options for leaving alert on and turning alert off. FIG. 78 shows the alert is turn off for player No. 59.

Figure 79:
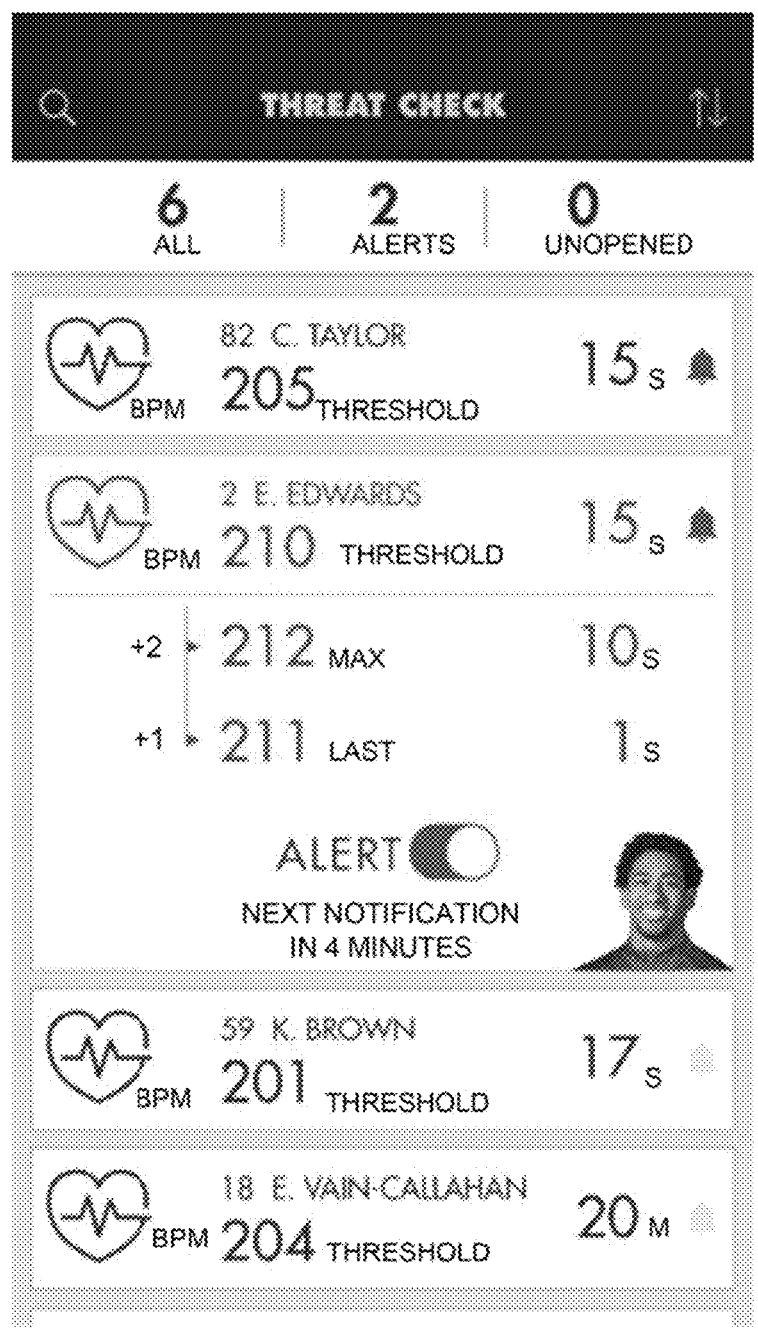
FIG. 79 is a screenshot displaying player No. 2 is above heart rate threshold.
Figure 80:
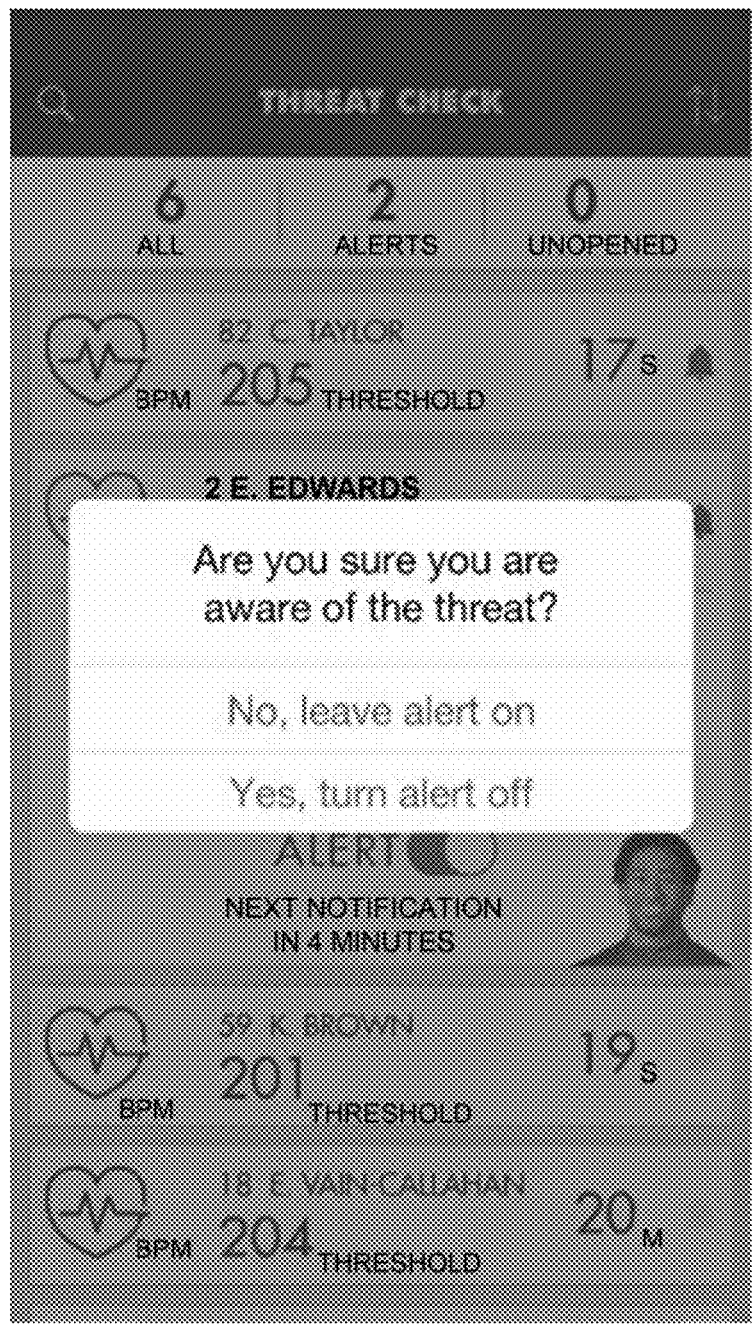
FIG. 80 is a screenshot displaying options of leaving alert one and turning alert off for player No. 2.
Figure 81:
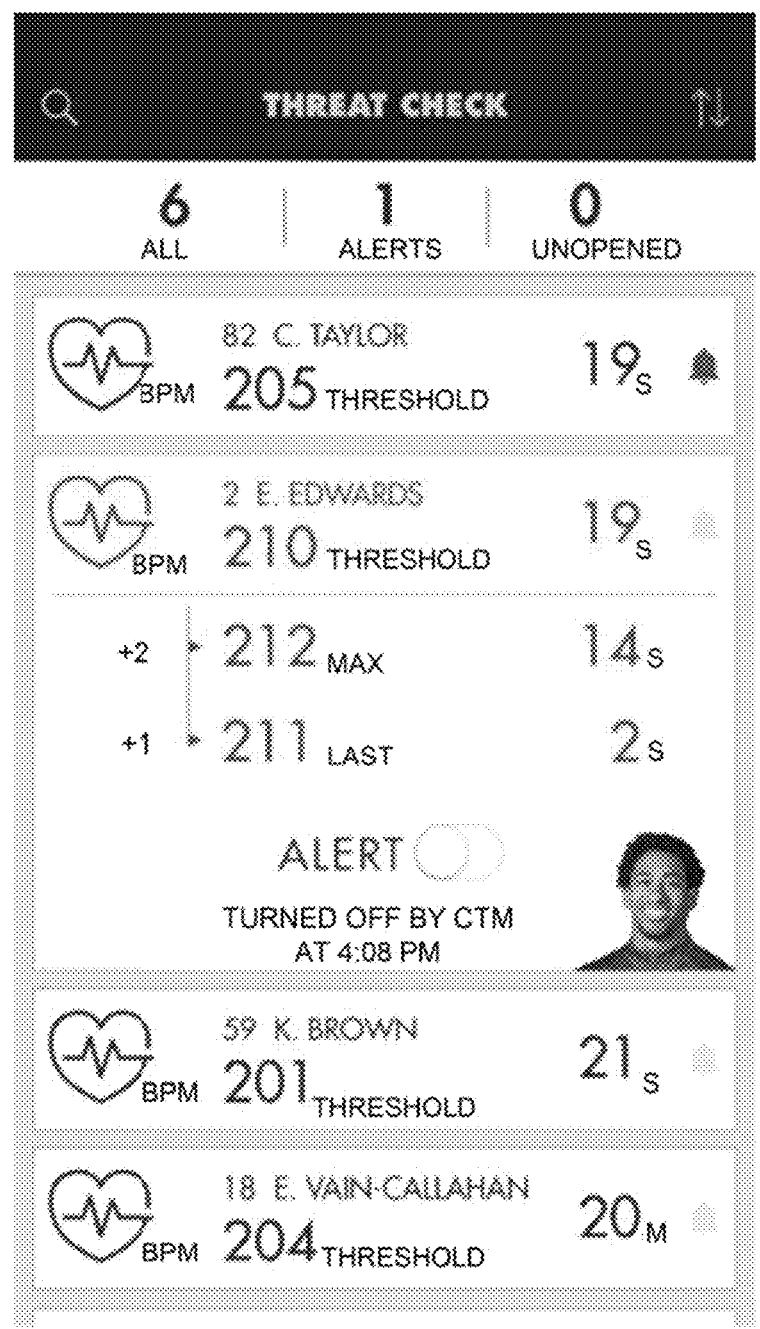
FIG. 81 is a screenshot displaying a medical safety alert is off for player No. 2.

Similarly, FIG. 79 is a screenshot displaying the heart rate alert above threshold for player No. 2. FIG. 80 shows options for leaving alert on and turning alert off. FIG. 81 shows the alert is turn off for player No. 2.

Figure 82:
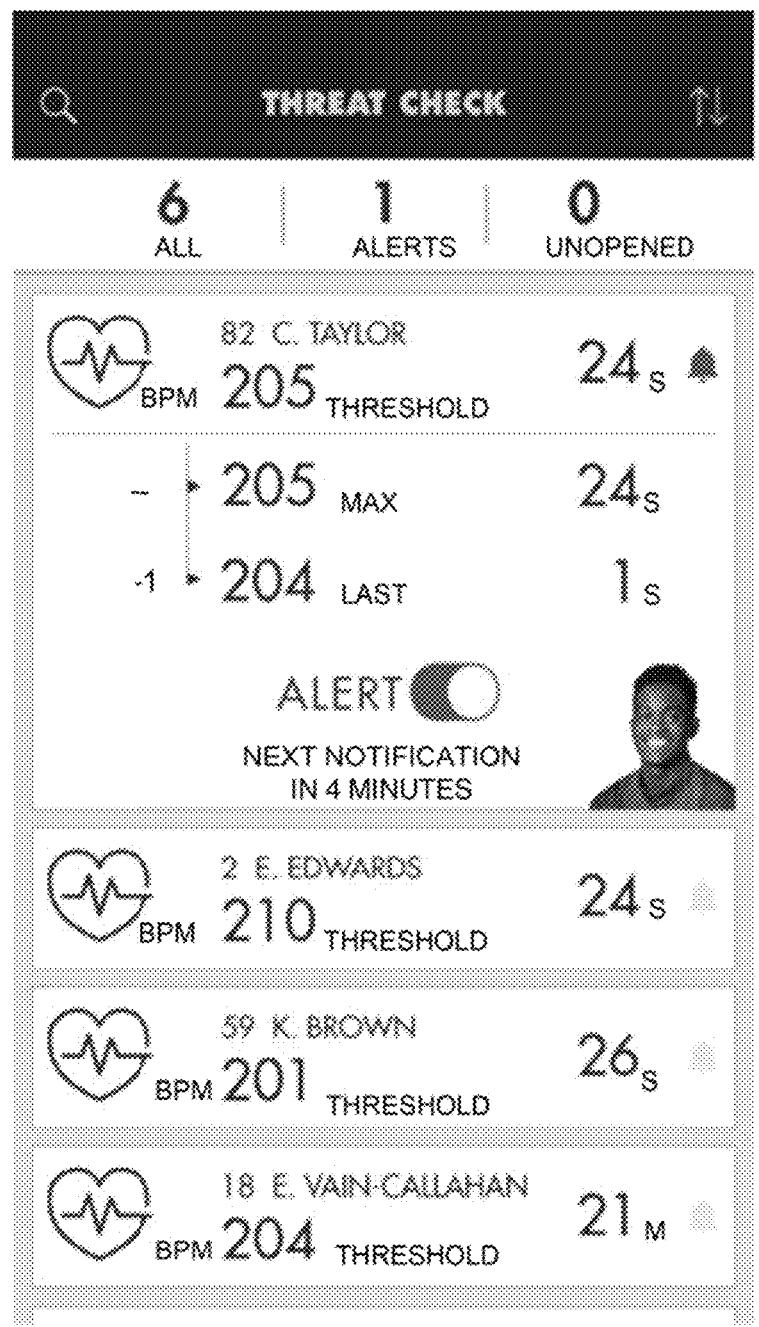
Figure 83:
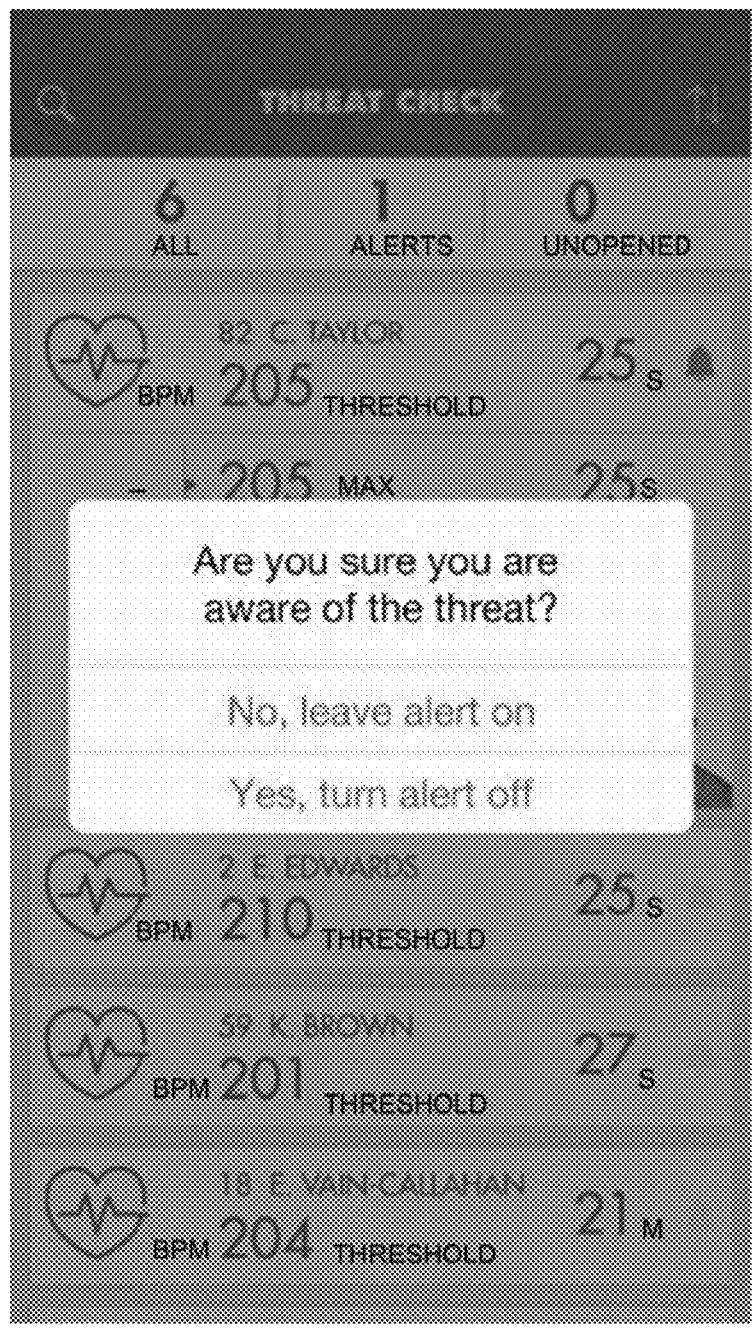
FIG. 83 is a screenshot displaying options of leaving alert one and turning alert off for player No. 82.
Figure 84:
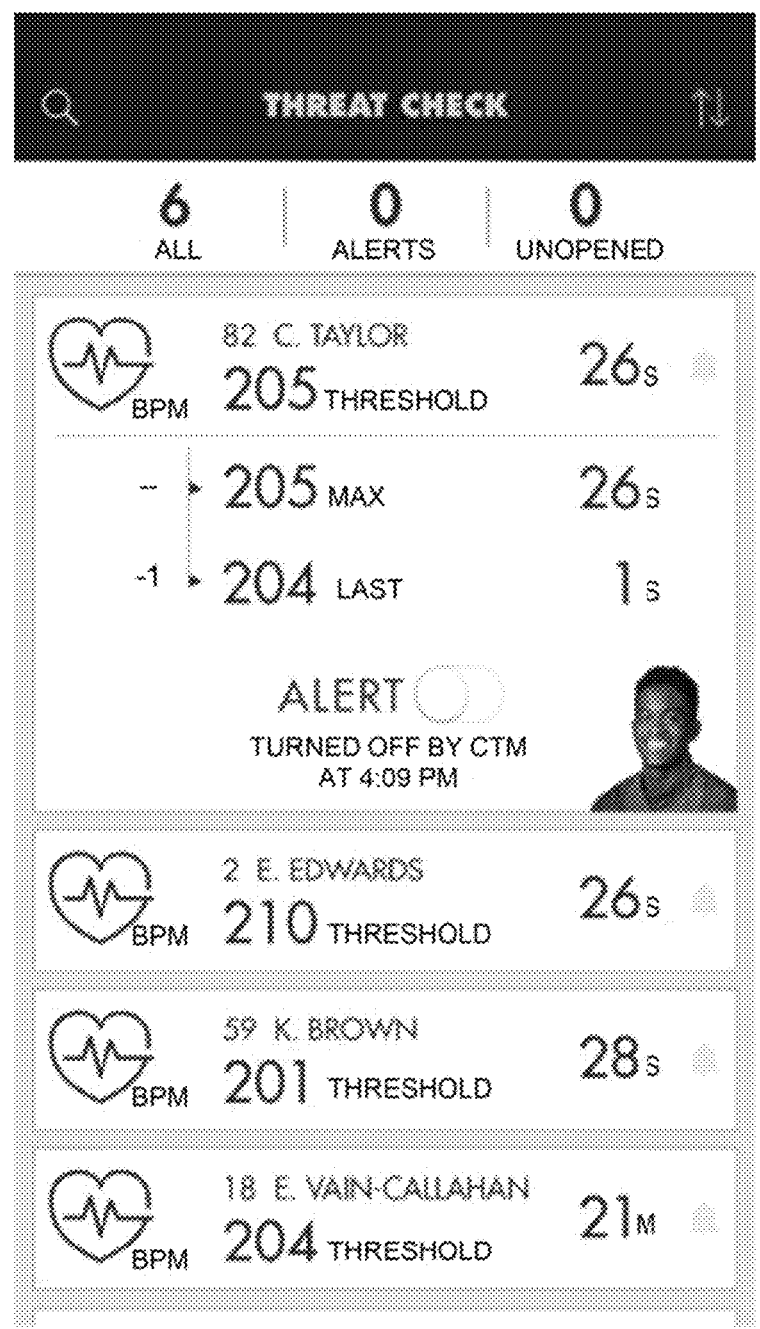
FIG. 84 is a screenshot displaying a medical safety alert is off for player No. 82.
Figure 85:
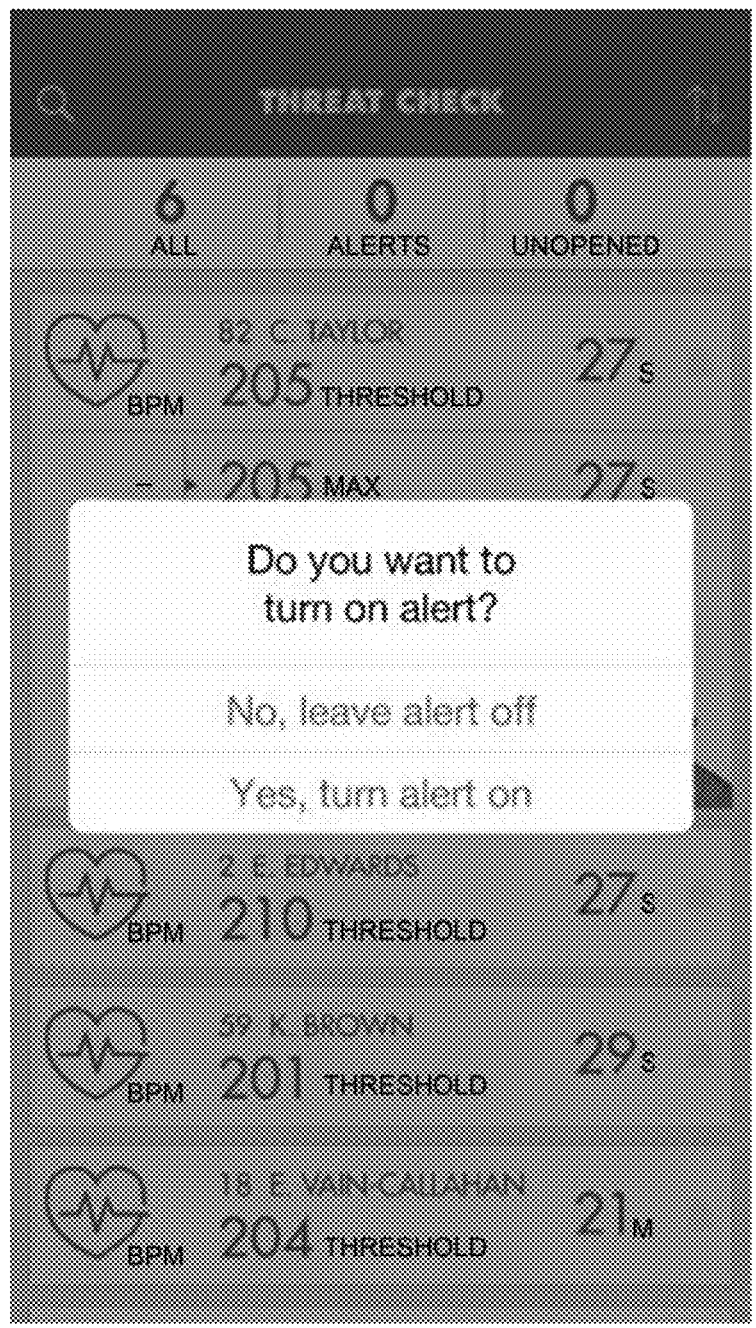
FIG. 85 is a screenshot displaying options of leaving alert one and turning alert off for player No. 82.
Figure 86:
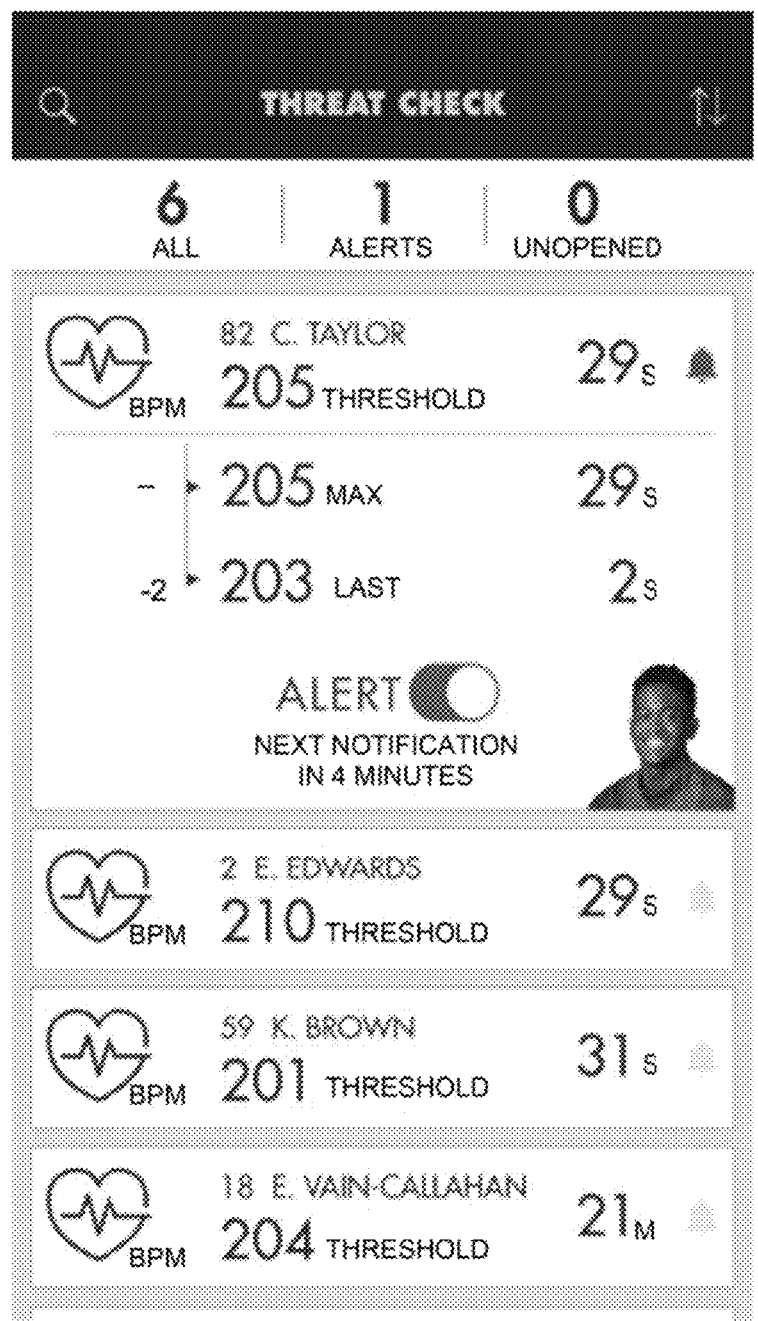
FIG. 86 is a screenshot displaying a medical safety alert is on for player No. 82.

FIG. 82 is a screenshot displaying the heart rate alert below threshold for player No. 82 with alert on. FIG. 83 shows options for leaving alert on and turning alert off. FIG. 84 shows the alert is turn off for player No. 82. FIG. 85 shows the alert can be turned back on for player No. 82. FIG. 86 shows the alert for player No. 82 is turned back on. Note that the alerts are listed in an order that the earliest alert in at the bottom and the latest alert in on top. Expanding one alert for view does not change the order.

Figure 87:
FIG. 87 is a screenshot displaying no medical alert received on the mobile phone.
Figure 88:
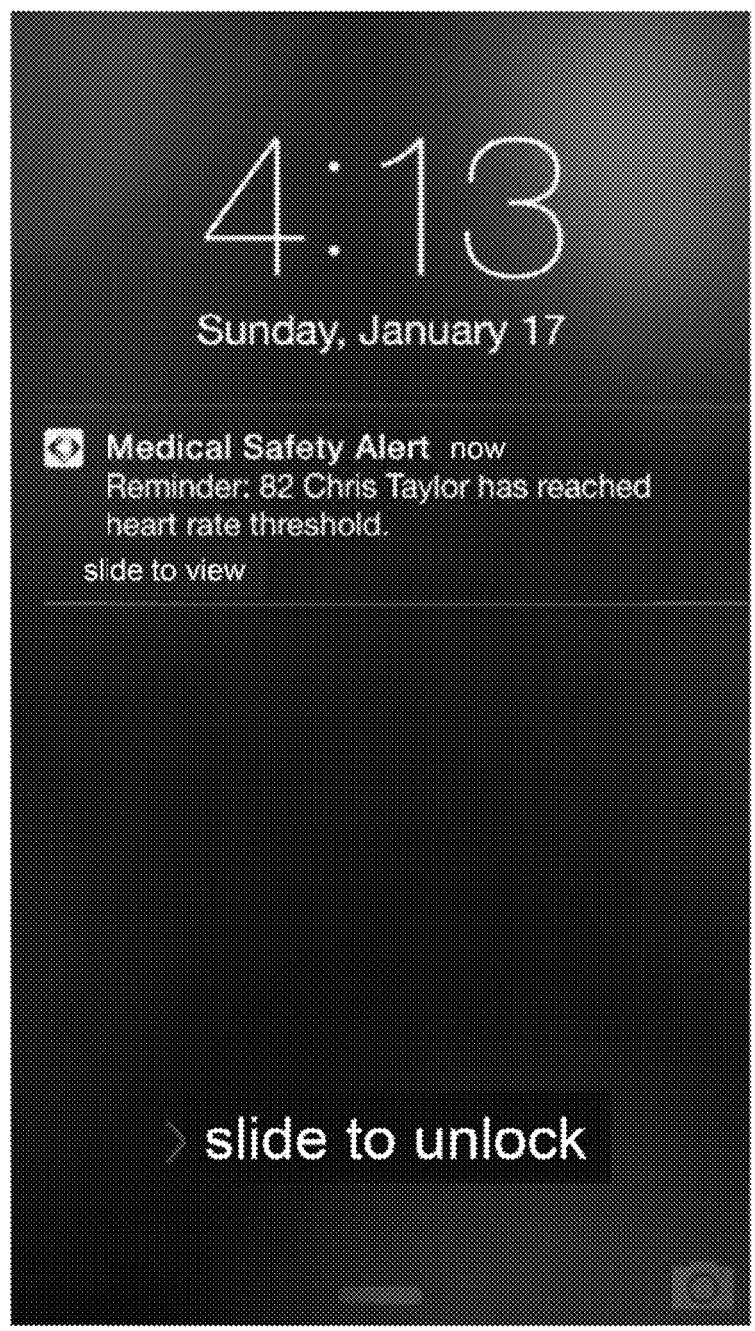
FIG. 88 is a screenshot displaying a reminder of a medical safety alert for player No. 82.

FIG. 87 is a screenshot displaying no medical alert received on the mobile phone. FIG. 88 is a screenshot for displaying a reminder of a medical safety alert for player No. 82 over a mobile phone.

Figure 89:
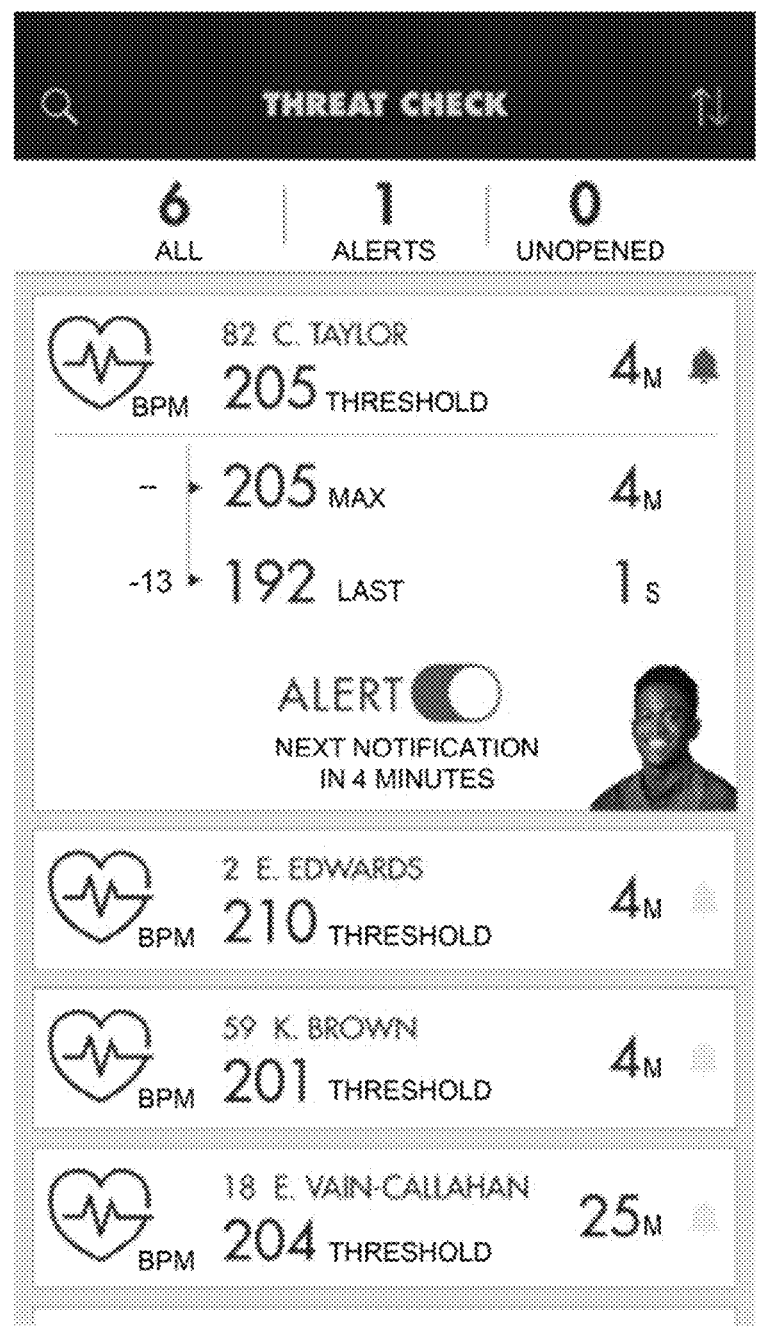
FIG. 89 is a screenshot displaying the heart rate for player No. 82 is below threshold.
Figure 90:
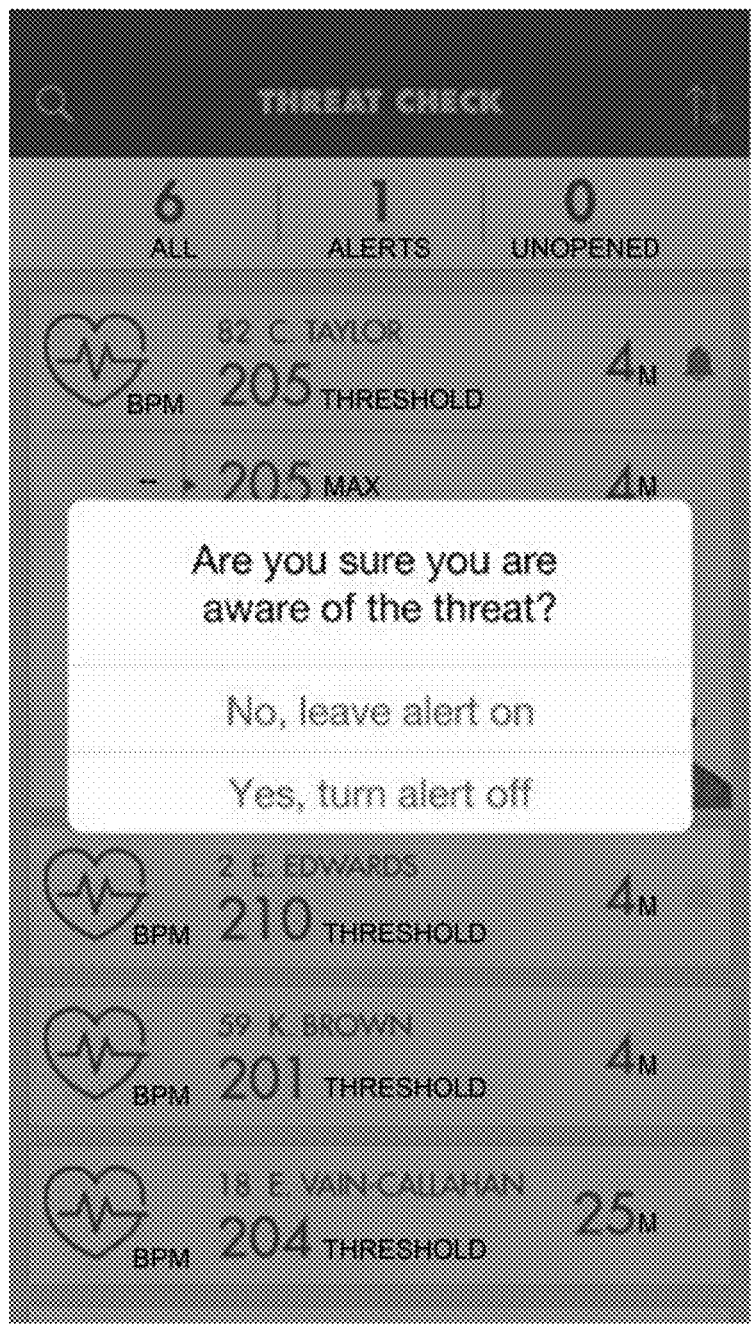
FIG. 90 is a screenshot displaying options of leaving alert one and turning alert off for player No. 82.
Figure 91:
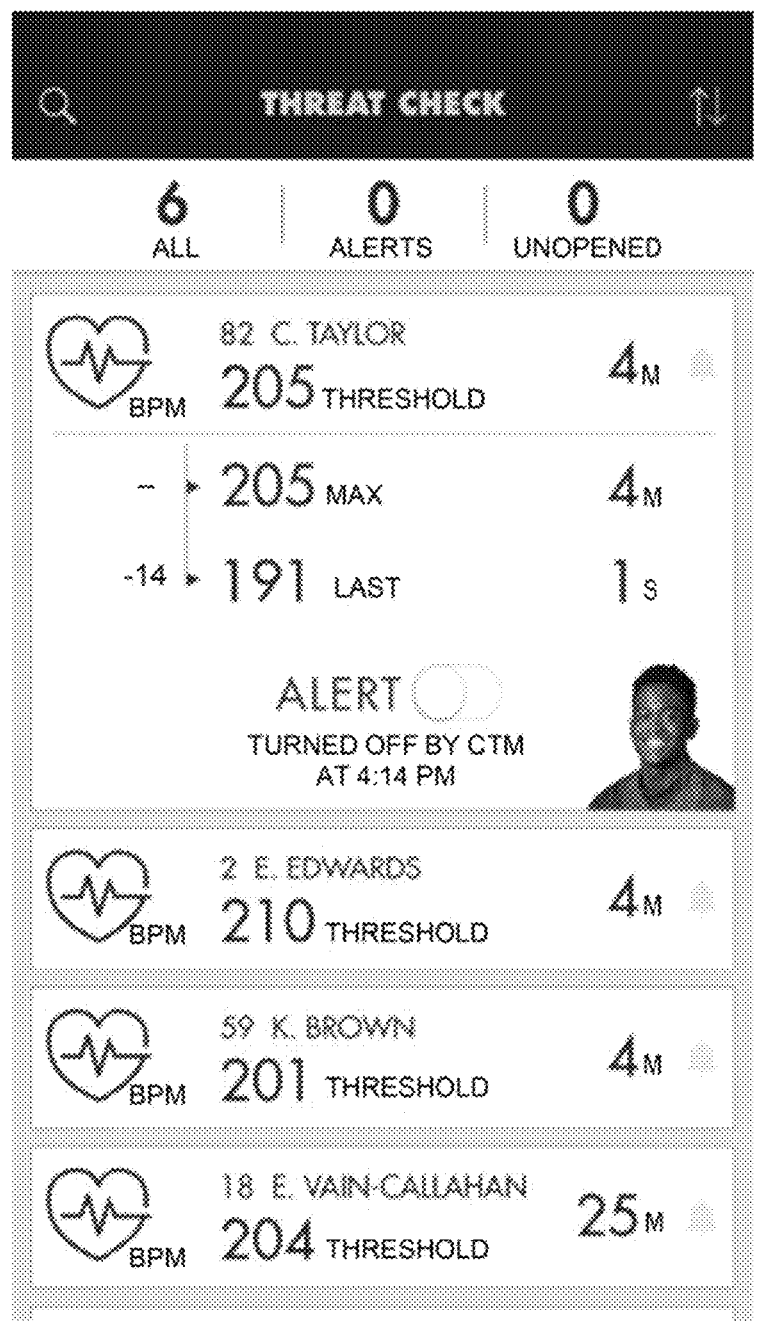
FIG. 91 is a screenshot displaying a medical safety alert is off for player No. 82.

FIG. 89 is a screenshot displaying the heart rate for player No. 82 is below threshold with alert on. FIG. 90 is a screenshot displaying options of leaving alert one and turning alert off for player No. 82. FIG. 91 is a screenshot displaying a medical safety alert is off for player No. 82.

Figure 92:
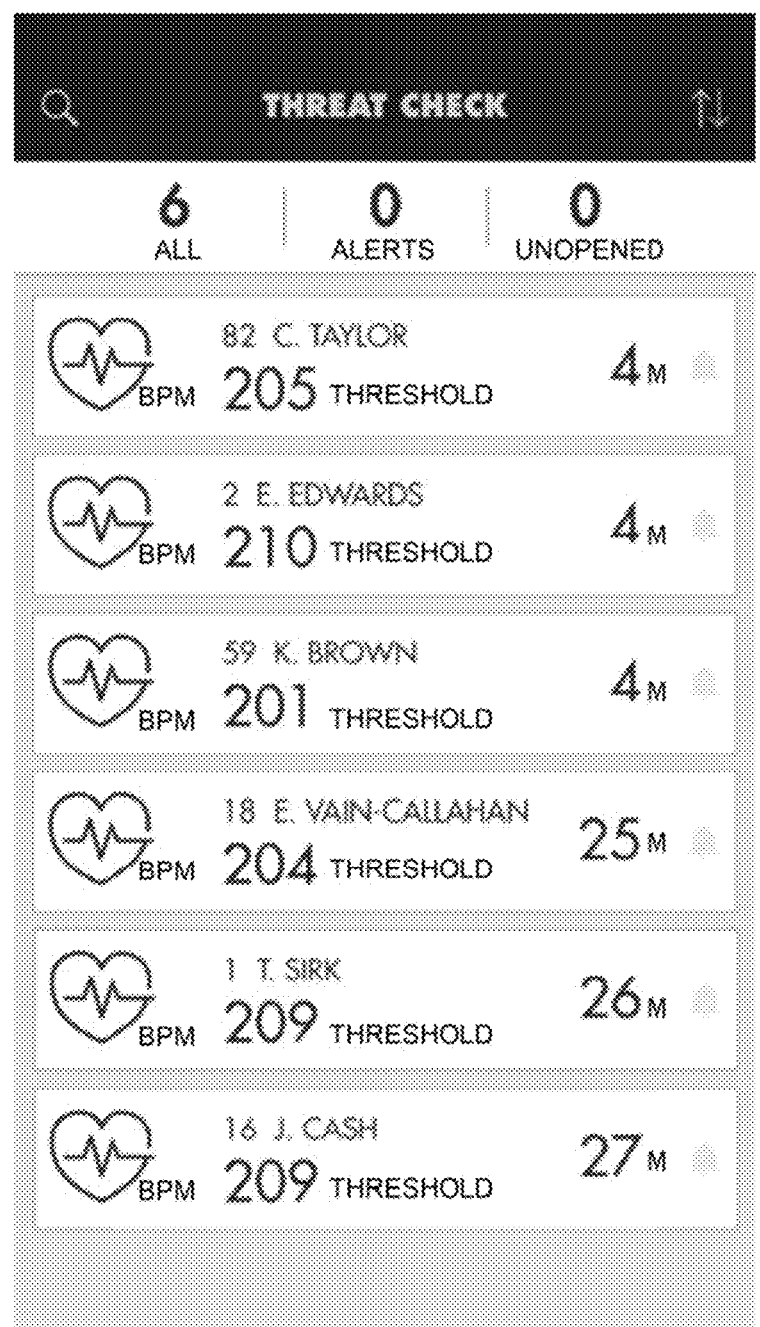
FIG. 92 is a screenshot for displaying all alerts received.
Figure 93:
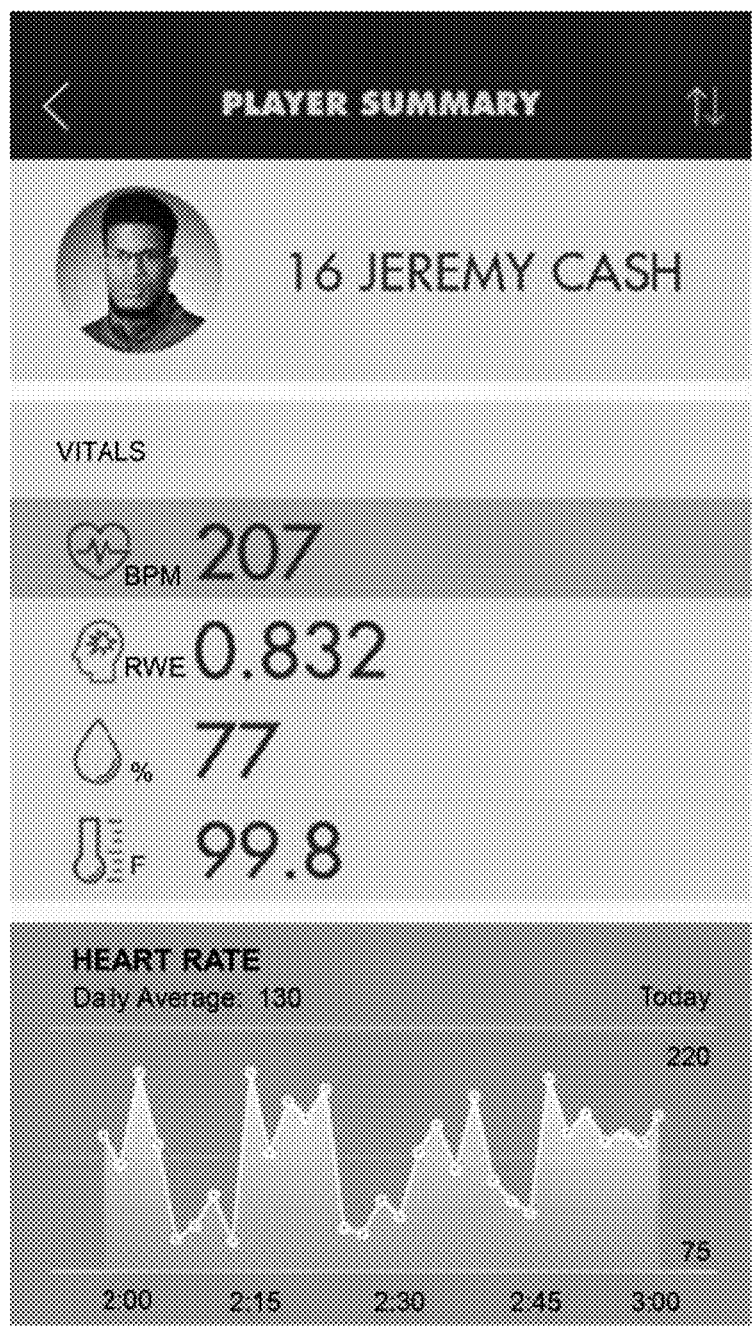
FIG. 93 is a screenshot for displaying player summary for player No. 16.
Figure 94:
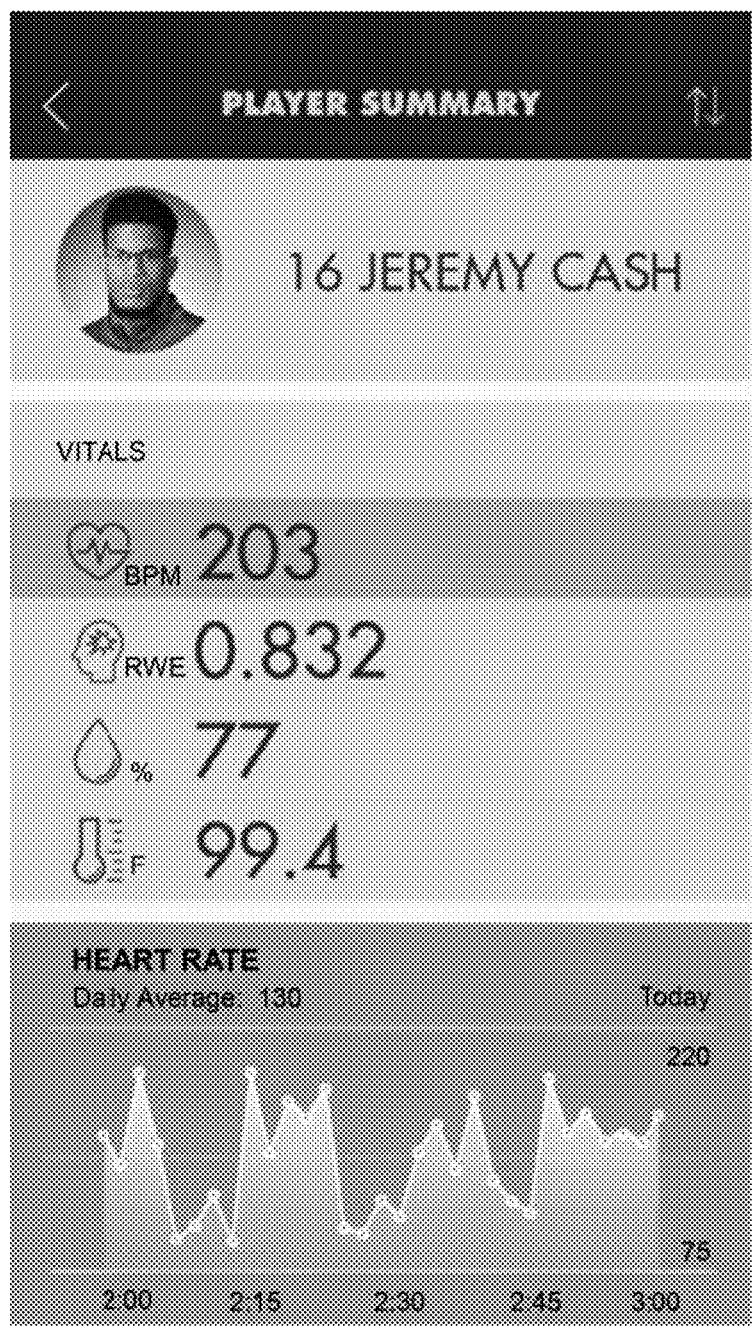
FIG. 94 is a screenshot for displaying player summary for player No. 16.

FIG. 92 is a screenshot for displaying all alerts received.

Figure 95:
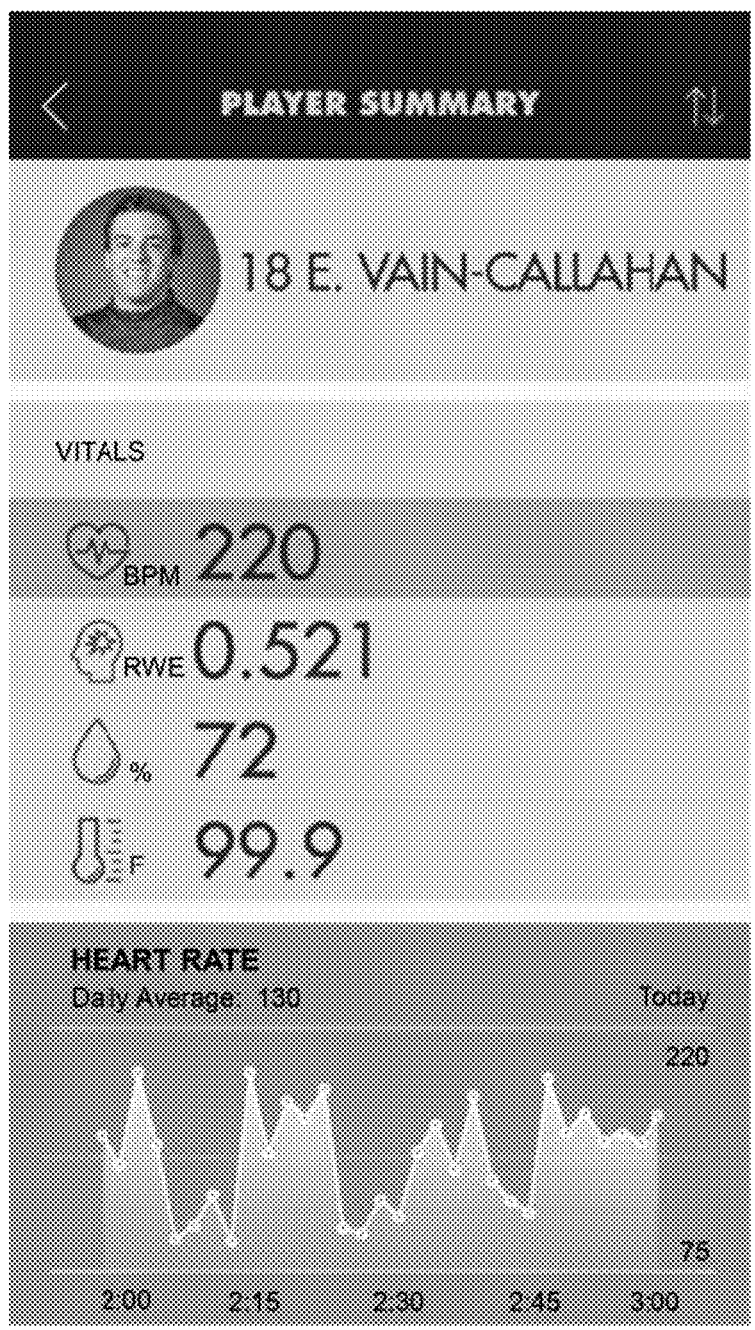
FIG. 95 is a screenshot for displaying player summary for player No. 18.
Figure 96:
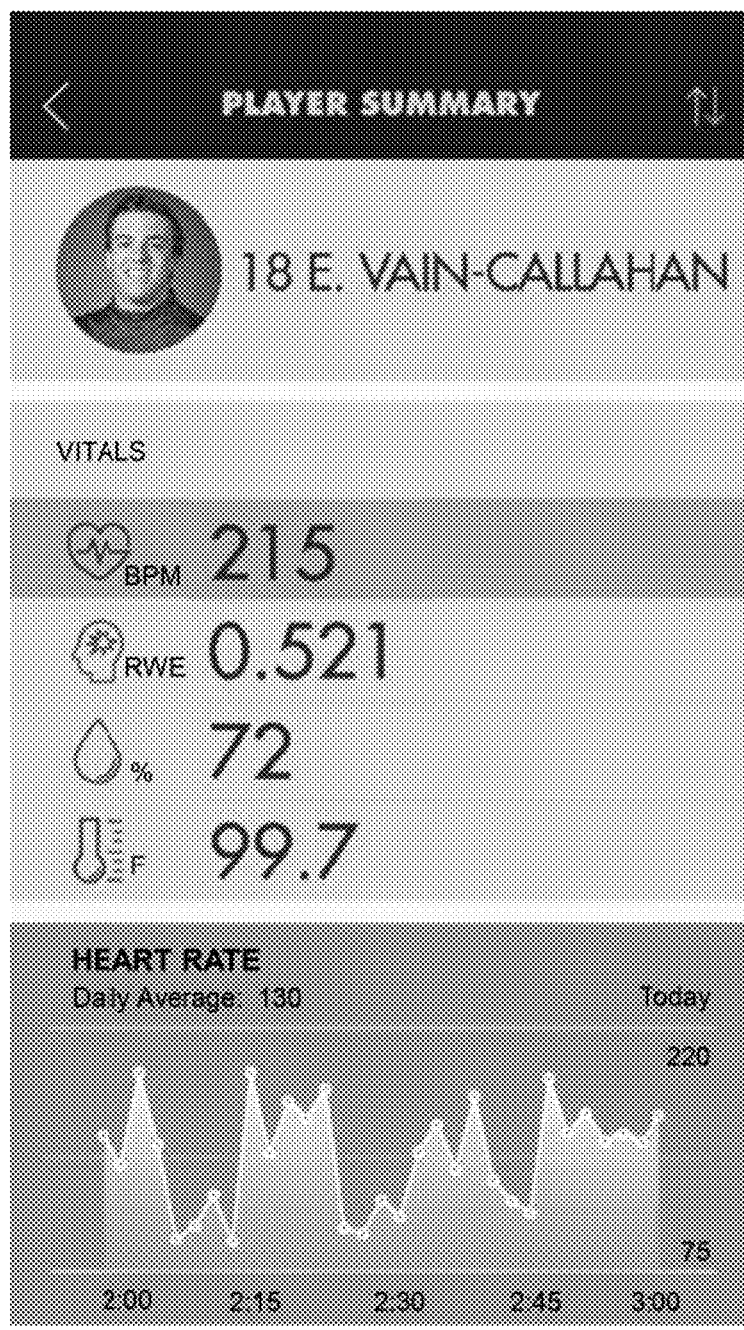
FIG. 96 is a screenshot for displaying player summary for player No. 18.
Figure 97:
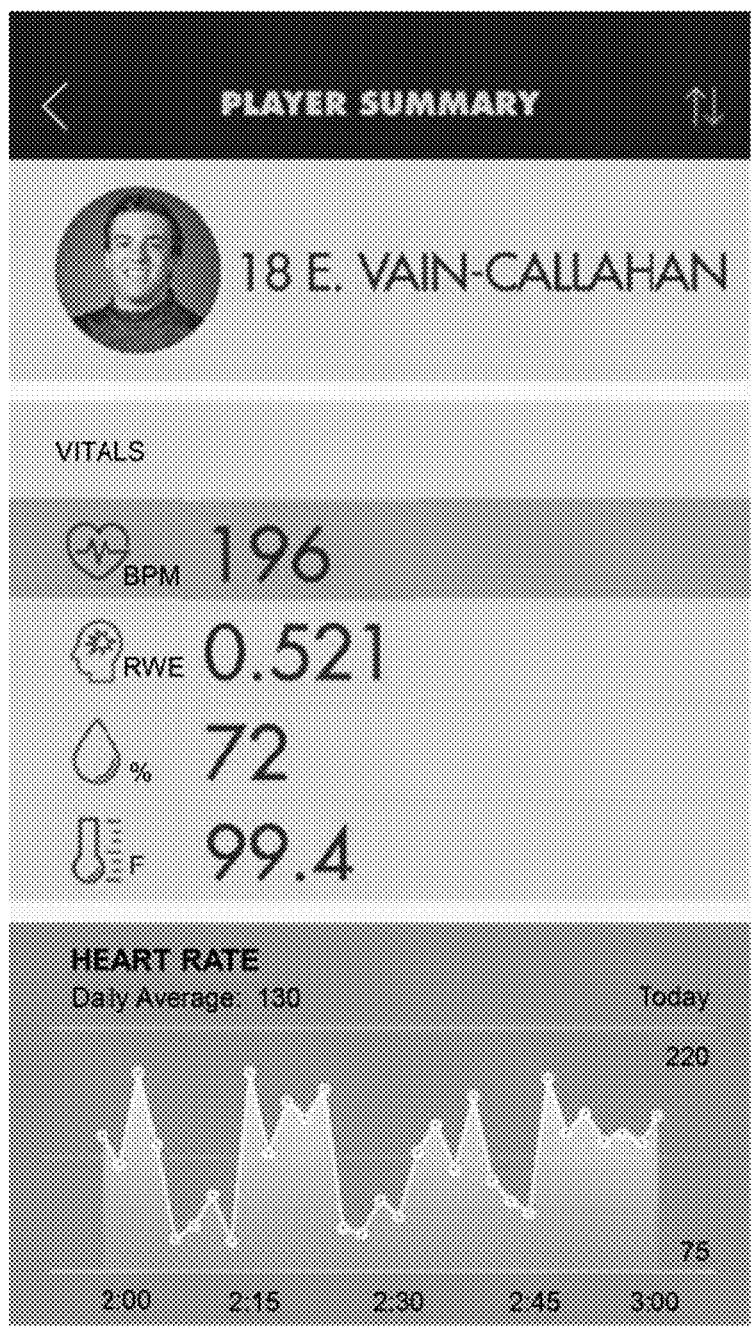
FIG. 97 is a screenshot for displaying player summary for player No. 18.
Figure 98:
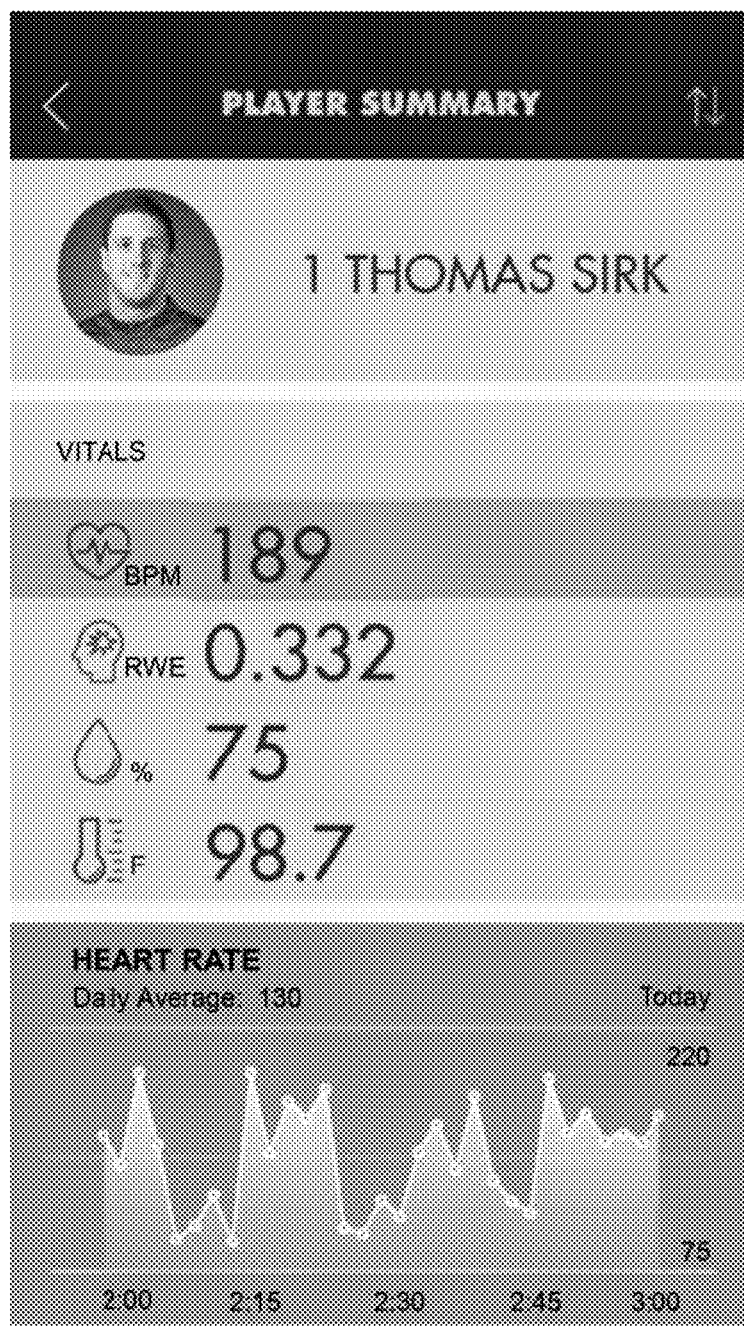
FIG. 98 is a screenshot for displaying player summary for player No. 1.
Figure 99:
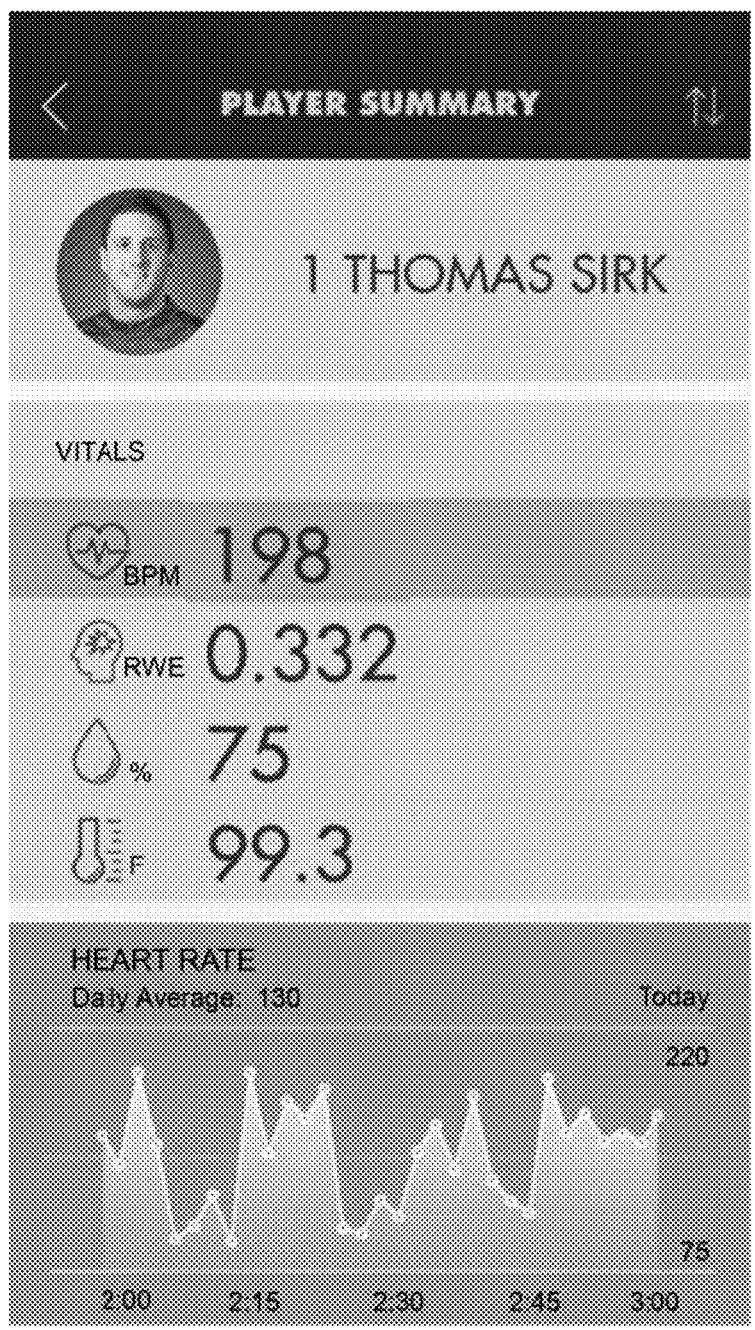
FIG. 99 is a screenshot for displaying player summary for player No. 1.
Figure 100:
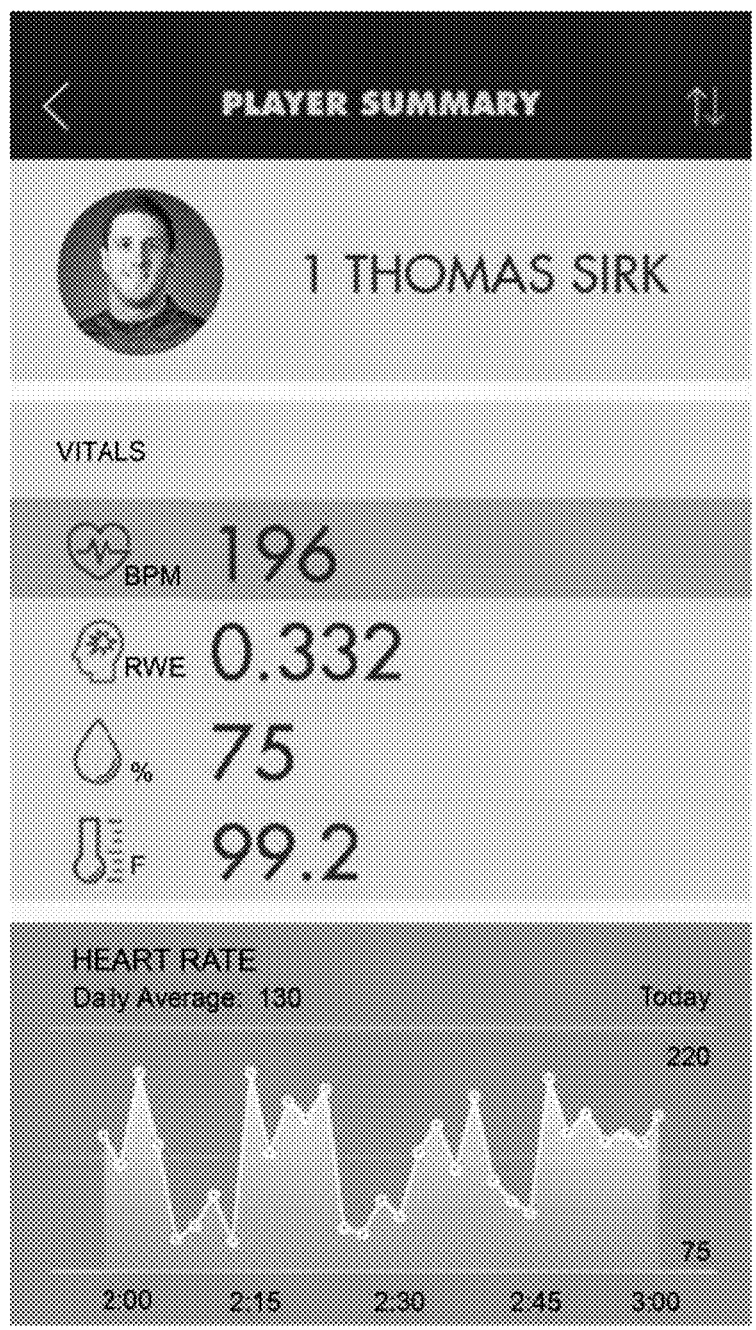
FIG. 100 is a screenshot for displaying player summary for player No. 1.

Similar to FIGS. 43 and 51, FIGS. 93-94 are screenshots for displaying player summary for player No. 16. FIGS. 95-97 are screenshots for displaying player summary for player No. 18. FIGS. 98-100 are screenshots for displaying player summary for player No. 1.

Figure 101:
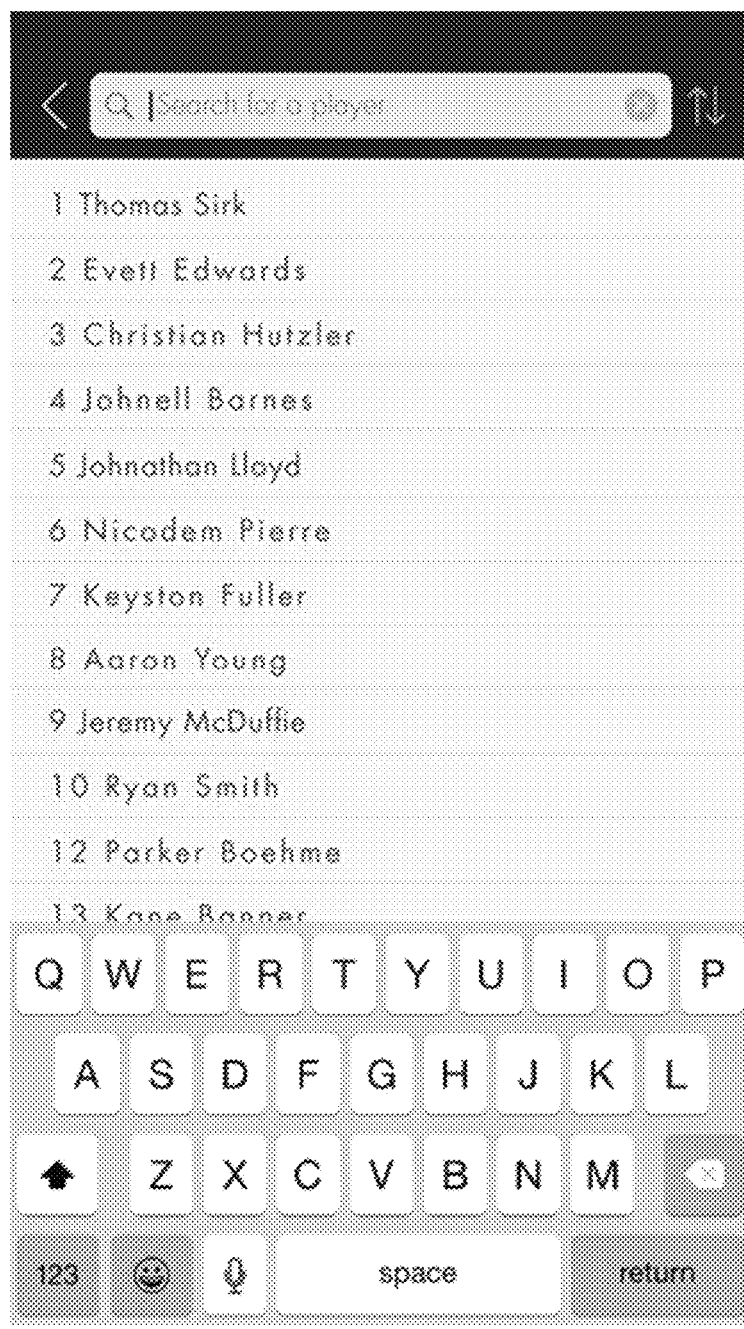
FIG. 101 is a screenshot for searching for a player.

Similar to FIG. 53, FIG. 101 is a screenshot for searching for a player in a list of players. FIG. 102 is a screenshot for typing a player name for searching.

Figure 103:
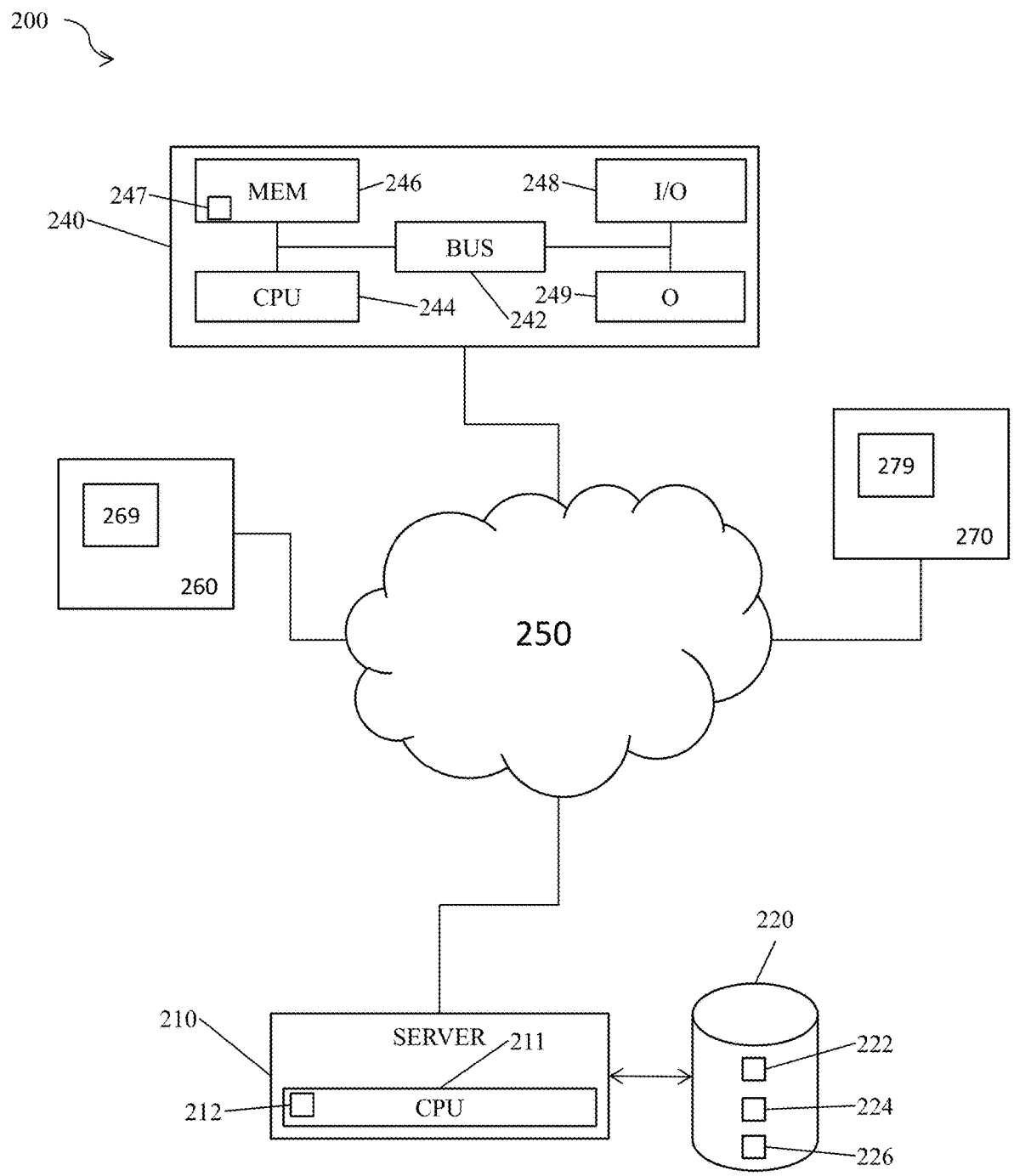
FIG. 103 is a schematic diagram of a cloud-based system according to one embodiment of the present invention.

Referring now to FIG. 103, a schematic diagram illustrating a virtualized computing network used in of one embodiment of the invention for automated systems and methods is shown. As illustrated, components of the systems and methods include the following components and sub-components, all constructed and configured for network-based communication, and further including data processing and storage. As illustrated in FIG. 103, a basic schematic of some of the key components of a financial settlement system according to the present invention are shown. The system 200 comprises a server 210 with a processing unit 211. The server 210 is constructed, configured and coupled to enable communication over a network 250. The server provides for user interconnection with the server over the network using a personal computer (PC) 240 positioned remotely from the server, the personal computer having instructions 247. Furthermore, the system is operable for a multiplicity of remote personal computers or terminals 260, 270, having operating systems 269, 279. For example, a client/server architecture is shown. Alternatively, a user may interconnect through the network 250 using a user device such as a personal digital assistant (PDA), mobile communication device, such as by way of example and not limitation, a mobile phone, a cell phone, smart phone, laptop computer, netbook, a terminal, or any other computing device suitable for network connection. Also, alternative architectures may be used instead of the client/server architecture. For example, a PC network, or other suitable architecture may be used. The network 250 may be the Internet, an intranet, or any other network suitable for searching, obtaining, and/or using information and/or communications. The system of the present invention further includes an operating system 212 installed and running on the server 210, enabling server 210 to communicate through network 250 with the remote, distributed user devices. The operating system may be any operating system known in the art that is suitable for network communication as described hereinbelow. Data storage 220 may house an operating system 222, memory 224, and programs 226.

Figure 104:
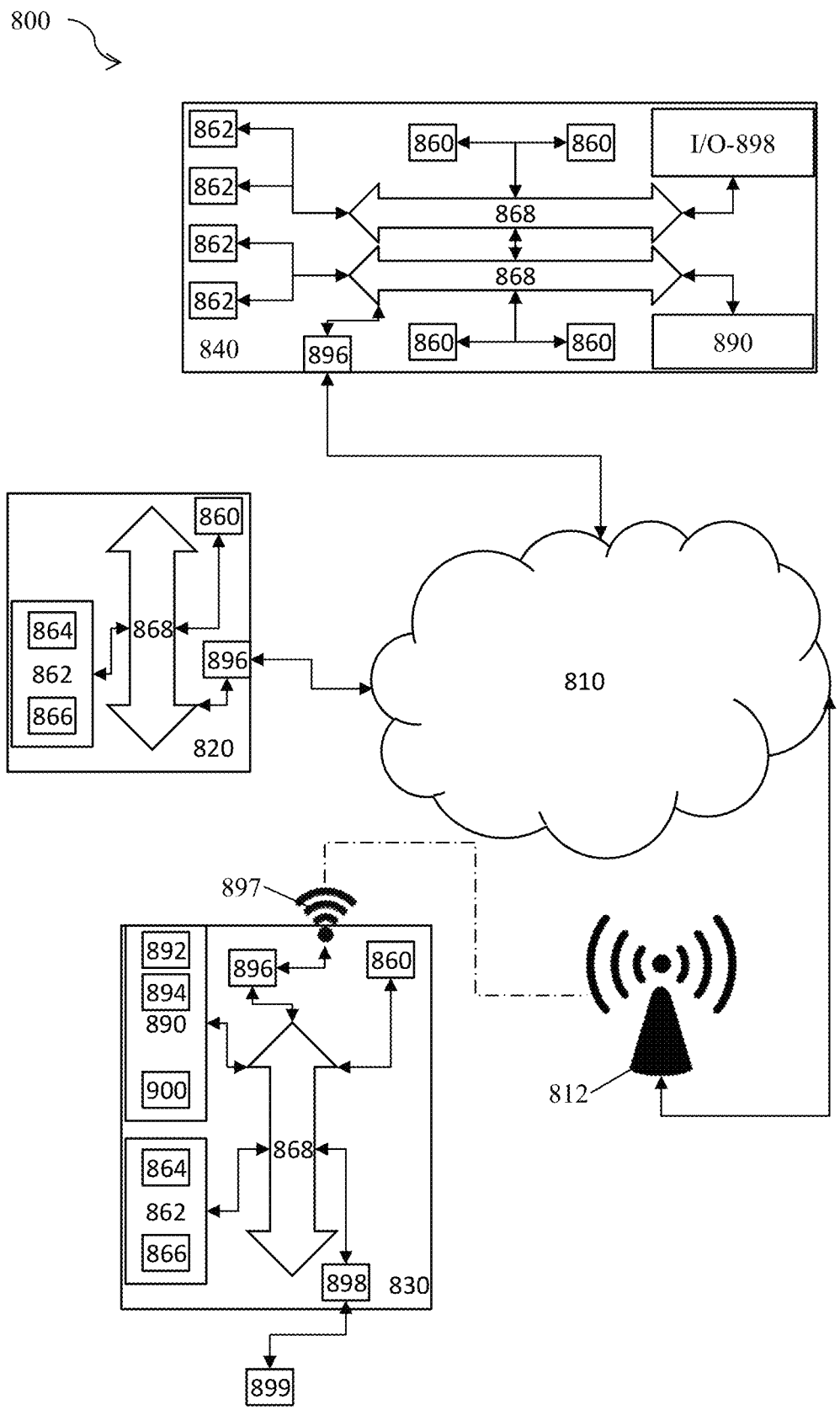
FIG. 104 is a schematic diagram of a cloud-based system according to another embodiment of the present invention.

Additionally or alternatively to FIG. 103, FIG. 104 is a schematic diagram of an embodiment of the invention illustrating a computer system, generally described as 800, having a network 810 and a plurality of computing devices 820, 830, 840. In one embodiment of the invention, the computer system 800 includes a cloud-based network 810 for distributed communication via the network wireless communication antenna 812 and processing by a plurality of mobile communication computing devices 830. In another embodiment of the invention, the computer system 800 is a virtualized computing system capable of executing any or all aspects of software and/or application components presented herein on the computing devices 820, 830, 840. In certain aspects, the computer system 800 may be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of digital computers 820, 840, 850 and mobile devices 830, such as a server, blade server, mainframe, mobile phone, a personal digital assistant (PDA), a smart phone, a desktop computer, a netbook computer, a tablet computer, a workstation, a laptop, and other similar computing devices. The components shown here, their connections and relationships, and their functions, are meant to be exemplary only, and are not meant to limit implementations of the invention described and/or claimed in this document.

In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 may additionally include components such as a storage device 890 for storing the operating system 892 and one or more application programs 894, a network interface unit 896, and/or an input/output controller 898. Each of the components may be coupled to each other through at least one bus 868. The input/output controller 898 may receive and process input from, or provide output to, a number of other devices 899, including, but not limited to, alphanumeric input devices, mice, electronic styluses, display units, touch screens, signal generation devices (e.g., speakers) or printers.

By way of example, and not limitation, the processor 860 may be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown in FIG. 104, a computing device 840 may use multiple processors 860 and/or multiple buses 868, as appropriate, along with multiple memories 862 of multiple types (e.g., a combination of a DSP and a microprocessor, a plurality of microprocessors, one or more microprocessors in conjunction with a DSP core).

Also, multiple computing devices may be connected, with each device providing portions of the necessary operations (e.g., a server bank, a group of blade servers, or a multi-processor system). Alternatively, some steps or methods may be performed by circuitry that is specific to a given function.

According to various embodiments, the computer system 800 may operate in a networked environment using logical connections to local and/or remote computing devices 820, 830, 840, 850 through a network 810. A computing device 830 may connect to a network 810 through a network interface unit 896 connected to the bus 868. Computing devices may communicate communication media through wired networks, direct-wired connections or wirelessly such as acoustic, RF or infrared through a wireless communication antenna 897 in communication with the network wireless communication antenna 812 and the network interface unit 896, which may include digital signal processing circuitry when necessary. The network interface unit 896 may provide for communications under various modes or protocols.

In one or more exemplary aspects, the instructions may be implemented in hardware, software, firmware, or any combinations thereof. A computer readable medium may provide volatile or non-volatile storage for one or more sets of instructions, such as operating systems, data structures, program modules, applications or other data embodying any one or more of the methodologies or functions described herein. The computer readable medium may include the memory 862, the processor 860, and/or the storage media 890 and may be a single medium or multiple media (e.g., a centralized or distributed computer system) that store the one or more sets of instructions 900. Non-transitory computer readable media includes all computer readable media, with the sole exception being a transitory, propagating signal per se. The instructions 900 may further be transmitted or received over the network 810 via the network interface unit 896 as communication media, which may include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory or other solid state memory technology, discs (e.g., digital versatile disc (DVD), HD-DVD, BLU-RAY, compact disc (CD), CD-ROM, floppy disc) or other optical storage, magnetic cassettes, magnetic tape, magnetic disk storage or other magnetic storage devices, or any other medium that can be used to store the computer readable instructions and which can be accessed by the computer system 800.

It is also contemplated that the computer system 800 may not include all of the components shown in FIG. 104, may include other components that are not explicitly shown in FIG. 104, or may utilize an architecture completely different than that shown in FIG. 104. The various illustrative logical blocks, modules, elements, circuits, and algorithms described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

In one embodiment, the present invention provides a standard file format for recording and processing sports data during a sports activity along a timeline. The standard file format is compatible for multiple sports, much smaller than a video format, and annotatable. In one embodiment, the file format is named as .MOST (Multi-Object Synchronized Timeline). In one embodiment, the present invention provides a MOST data server for synchronizing and processing various input data and generating processed data in .MOST format. In one embodiment, the .MOST data and the .MOST file include 3D data.

In one embodiment, the present invention provides systems, methods, and apparatus for data collection and analytics for a sports activity. A server platform is constructed and configured for network communication with a multiplicity of sensors and a multiplicity of user devices. The server platform comprises at least one intelligence engine and at least one synchronization engine. Each of the multiplicity of user devices includes at least one application program. The multiplicity of sensors tracks a multiplicity of world objects related to the sports activity, collects and communicates data inputs to the server platform in real time or near real time, thereby creating tracking data. The server platform collects and integrates the tracking data from the multiplicity of sensors and scoring data for the sports activity. The server platform automatically correlates the tracking data and the scoring data with a corresponding Coordinated Universal Time (UTC) timecode based on rules related to the sports activity, thereby creating a multiplicity of UTC-coded data sets. The server platform synchronizes the multiplicity of UTC-coded data sets, thereby creating a time-synchronized data set. The server platform provides analytics based on the time-synchronized data set, thereby creating analyzed data. The multiplicity of user devices displays the analyzed data based on the at least one application program.

Figure 105:
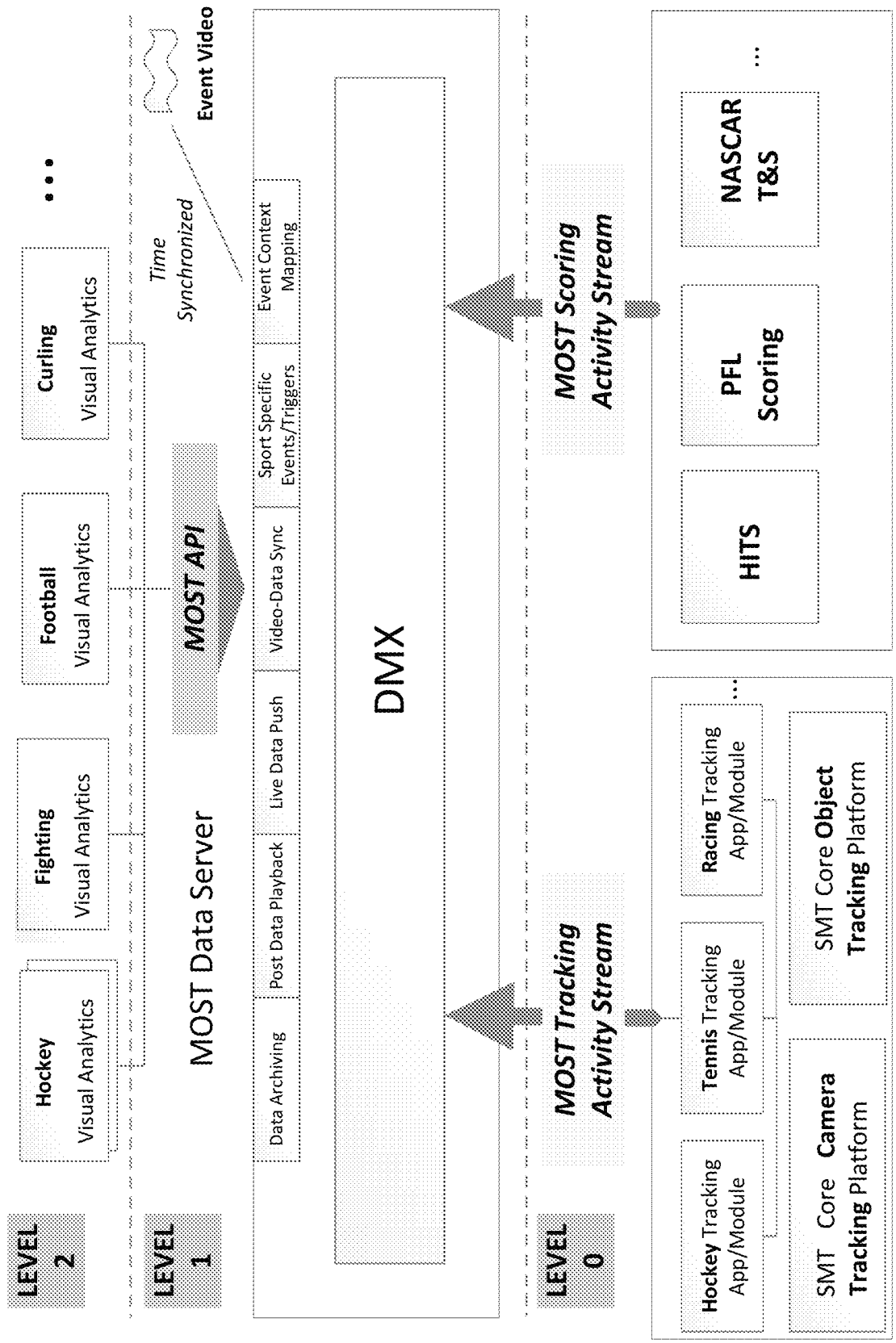
FIG. 105 is a high-level architecture of an integral system according to one embodiment of the present invention.

In one embodiment, level 1 of the integral system of the present invention includes an intelligence engine DMX for a specific sport to collect and aggregate tracking stats and scoring events, and provide basic analytics and advanced analytics. In one embodiment, level 1 of the integral system of the present invention also includes a synchronization engine. In one embodiment, the synchronization engine is a MOST data server operable to normalize and synchronize all data collected from level 0 into .MOST format. The MOST data server also provides data archiving, post data playback, live data push, video-data synchronization, sport specific triggers, and event context mapping. Level 1 of the integral system also provides a MOST API to provide MOST data to various applications for various sports at level 2. FIG. 105 is a high-level architecture of an integral system according to one embodiment of the present invention.

In one embodiment, level 1 of the integral system of the present invention includes a timecode synchronization layer operable to automate and facilitate collection of all official stats data and all tracking data on field from level 0 and timestamp all the collected data with a world UTC timecode for a certain sport. In one embodiment, all the collected data with UTC timecode is synchronized to a production timecode for broadcasting purposes. The timecode synchronization layer at level 1 provides full integration of input data from level 0.

In one embodiment, there is at least one arena domain server and at least one arena MOST server at level 1. Each arena domain server includes an intelligence engine providing intelligent analytics based on official scoring events and activity events. Each arena MOST server includes a MOST engine for normalizing all the collected data from level 0. The MOST engine is connected to an analytics API for domain queries in the arena domain server. In one embodiment, the arena domain server stores all the scoring data and tracking data for a predetermined period of time (e.g., a few seconds) that is long enough for official scoring purposes, but the arena MOST server stores all data in .MOST format permanently. In one embodiment, the at least one arena domain server and the at least one arena MOST server are connected to a cloud-based server platform. The cloud-based server platform is also operable for processing domain data and MOST data the same as the at least one arena domain server and the at least one arena MOST server is respectively.

In one embodiment, there is an Application Programming Interface (API) and Real-Time Push (RTP) layer at level 1 connecting to various applications at level 2 including third-party data feeds, displaying, broadcasting, and web applications. Applications at level 2 are operable to connect to the cloud-based server platform and/or the local arena servers via the API and RTP layer for data retrieval.

Figure 106:
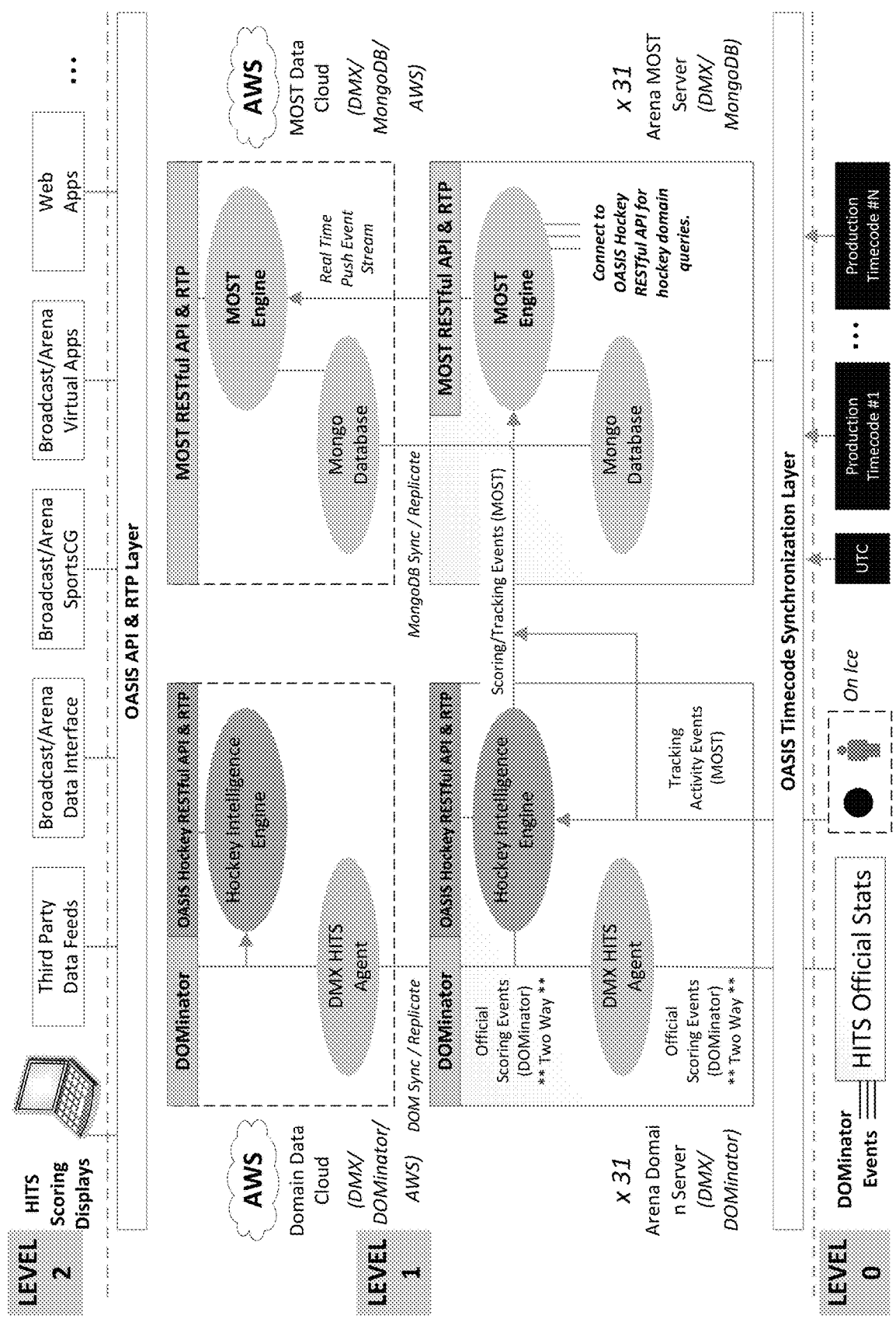
FIG. 106 is an architecture diagram of an integral system for data collection and analytics for ice hockey according to one embodiment of the present invention.
Figure 107:
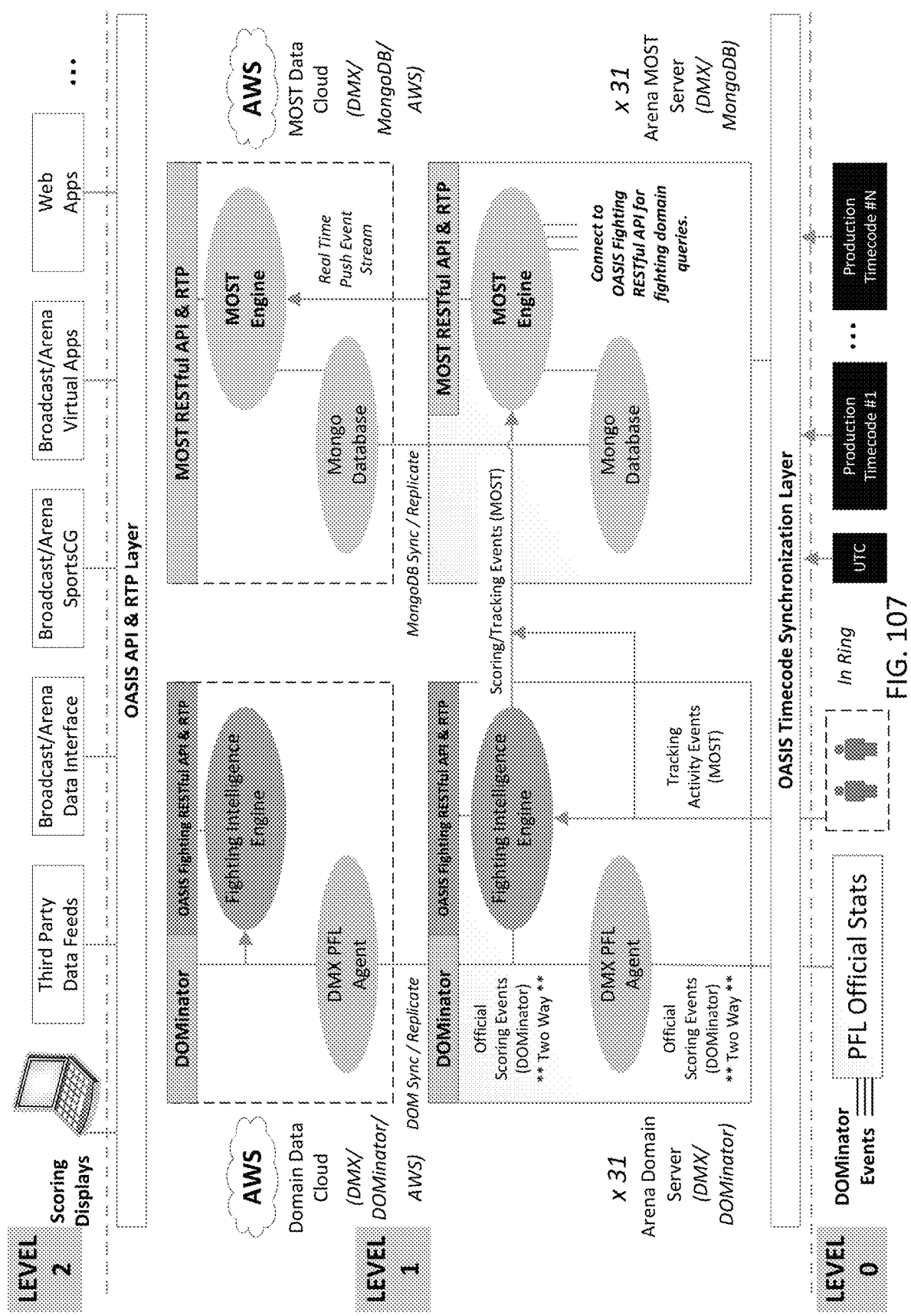
FIG. 107 is an architecture diagram of an integral system for data collection and analytics for fighting according to one embodiment of the present invention.

FIG. 106 is an architecture diagram of an integral system for data collection and analytics for ice hockey according to one embodiment of the present invention. FIG. 107 is an architecture diagram of an integral system for data collection and analytics for fighting according to one embodiment of the present invention. The intelligence engine is sport specific. The MOST engine applies to all sports so that the integral system can be used in all sports with minimal adaptations.

Figure 108:
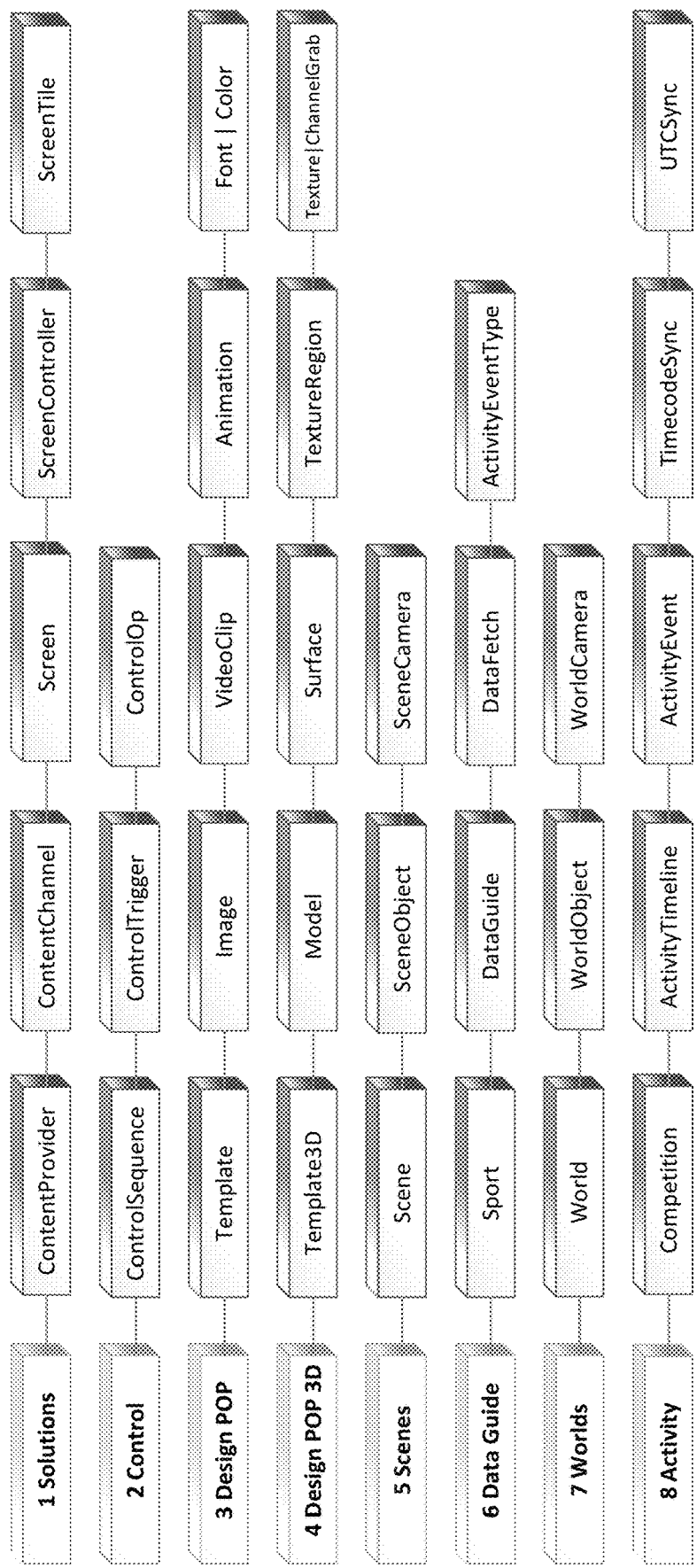
FIG. 108 illustrates an eight-layer object model generated by a MOST server and a MOST renderer according to one embodiment of the present invention.
Figure 109:
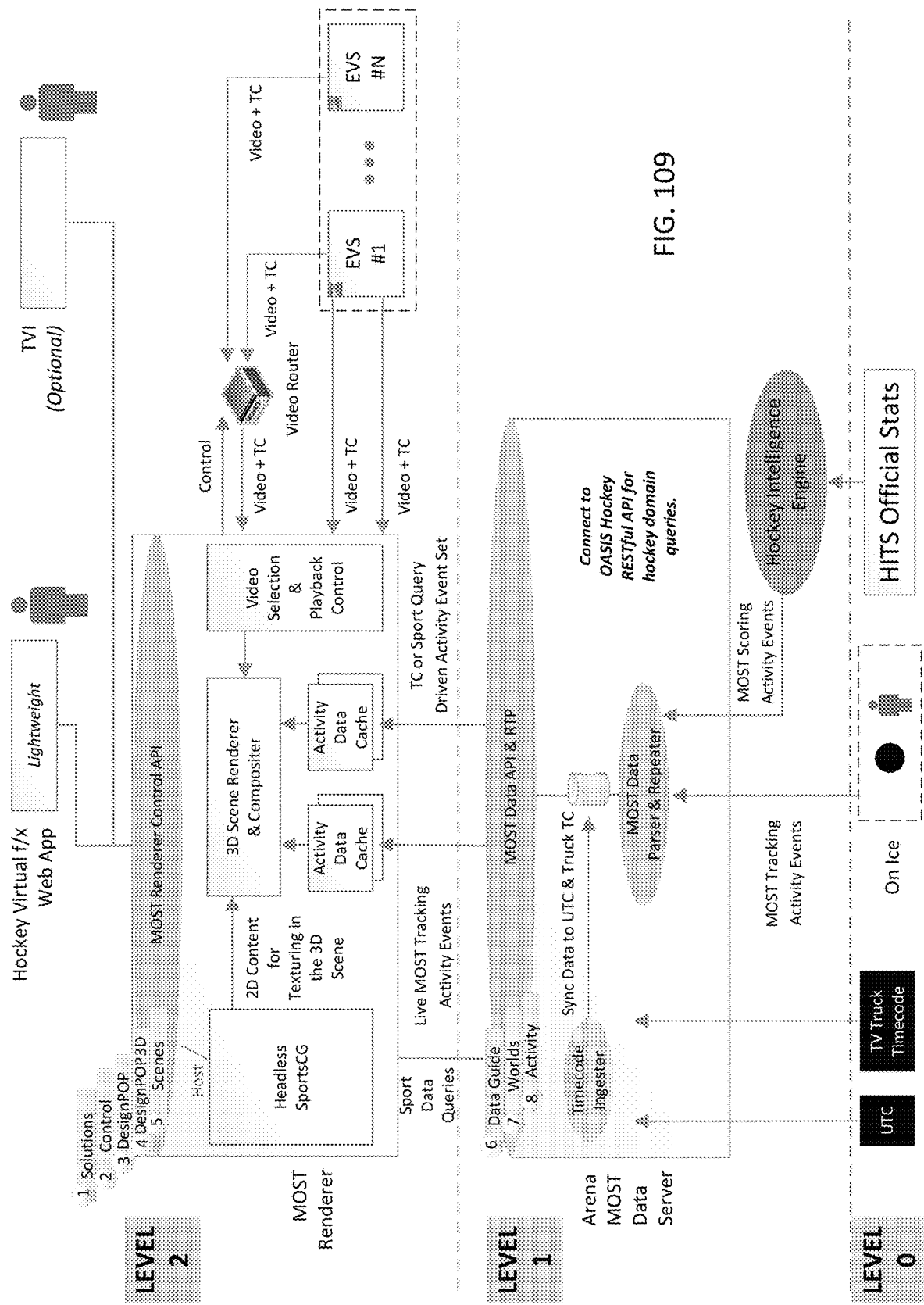
FIG. 109 is an example of a visual analytics application according to one embodiment of the present invention.
Figure 110:
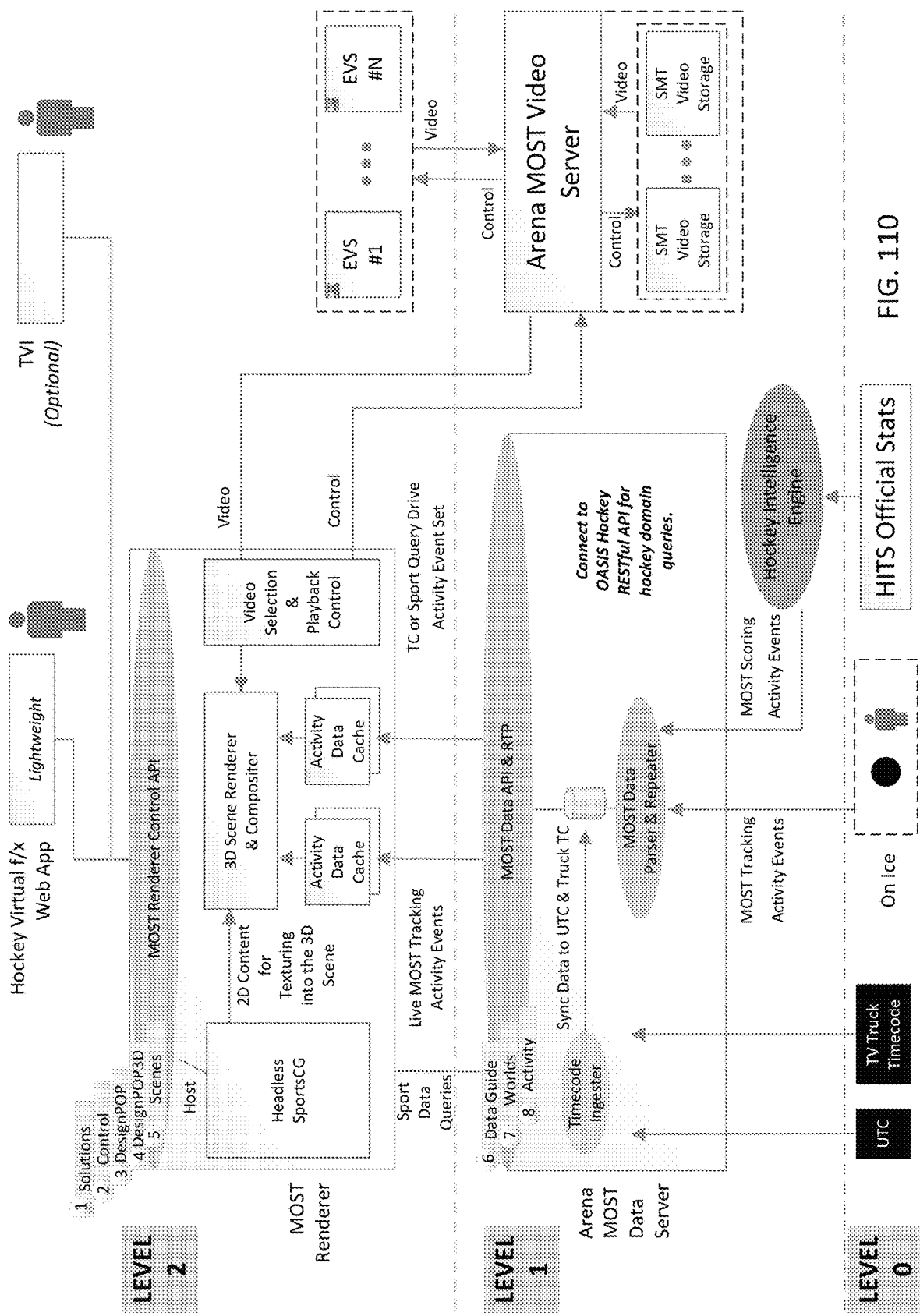
FIG. 110 is an example of a visual analytics application according to another embodiment of the present invention.

FIG. 108 illustrates an eight-layer object model generated by a MOST server and a MOST renderer according to one embodiment of the present invention. FIG. 109 is an example of a visual analytics application according to one embodiment of the present invention. FIG. 110 is an example of a visual analytics application according to another embodiment of the present invention. In FIGS. 109 and 110, an arena MOST data server at level 1 generates Data Guide object data, Worlds object data, and Activity object data in .MOST format based on tracking activity events and scoring activity events at level 0, and sends all the object data to a MOST renderer at level 2 via a MOST data API & RTP. In one embodiment, the MOST renderer queries the arena MOST data server to obtain all the object data generated by the arena data server. The MOST renderer is operable to render a 3D scene based on data from the arena MOST data server, and the MOST renderer is further operable for video selection and playback control. The MOST renderer control API provides Solutions object data, Control object data, Design POP object data, Design POP 3D object data, and Scenes object data to various applications at level 2.

In one embodiment, broadcasting equipment sends video data with timecodes to the MOST renderer, and the MOST renderer is operable to control the broadcasting equipment. The broadcasting equipment includes multiple broadcasting devices in one embodiment. In another embodiment, as illustrated in FIG. 110, an arena MOST video server is provided at level 1 to standardize and process video data from multiple broadcasting equipment and send the processed video data to the MOST renderer. The MOST renderer of level 2 is operable to control the arena MOST video server for video processing.

Figure 111:
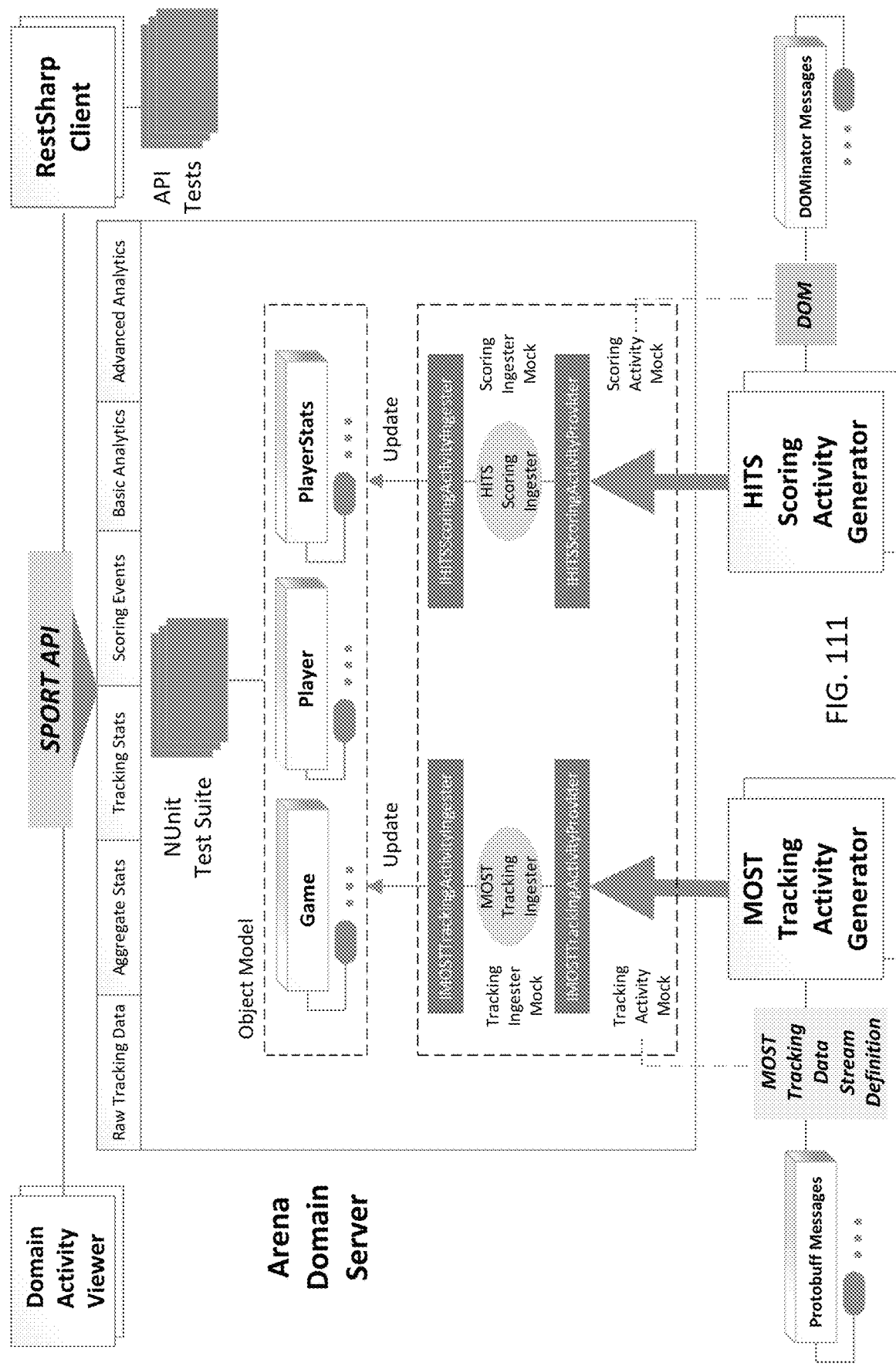
FIG. 111 is an architecture of an arena domain server according to one embodiment of the present invention.

FIG. 111 is an architecture of an arena domain server according to one embodiment of the present invention. In one embodiment, the arena domain server communicates with a MOST tracking activity generator and a scoring activity generator, ingests tracking data and scoring data, and updates object models including but not limited to a Game object model, a Player object model, and a Player Stats object model. The arena domain server provides raw tracking data, aggregate stats data, track stats data, performs basic analytics and advanced analytics. A domain activity viewer is provided to access to the arena domain server via a sport API.

Figure 112:
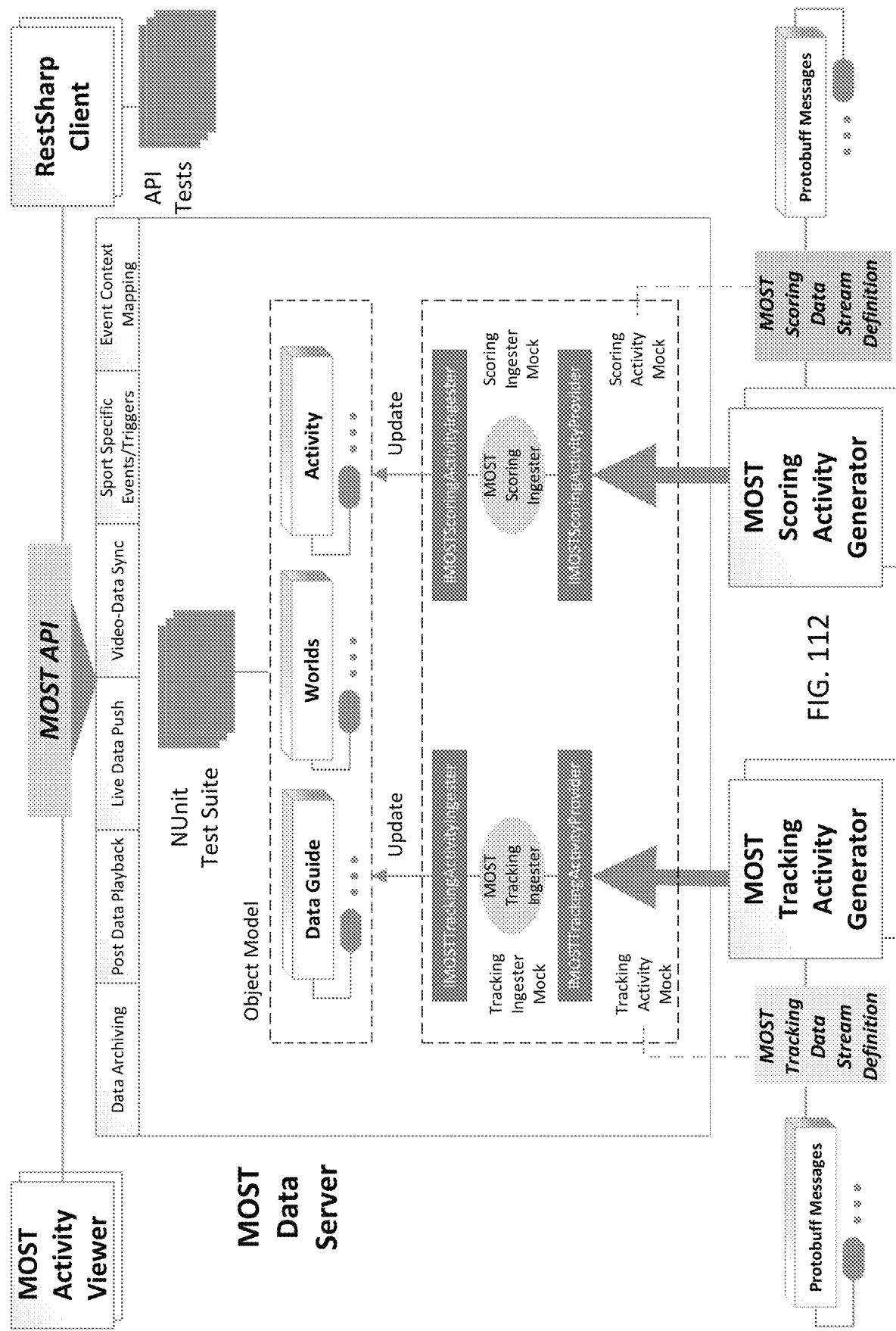
FIG. 112 is an architecture of a MOST data server according to one embodiment of the present invention.

FIG. 112 is an architecture of a MOST data server according to one embodiment of the present invention. In one embodiment, the MOST data server is operable to communicate with a MOST tracking activity generator and a MOST scoring activity generator, ingest tracking data and scoring data, and update object models including but not limited to a Data Guide object model, Worlds object model, and Activity object model. The MOST data server provides data archiving, post data playback, live data push, video-data synchronization, sport specific events/triggers, and event context mapping. A MOST activity viewer is operable to access to the MOST data server via a MOST API.

Figure 113:
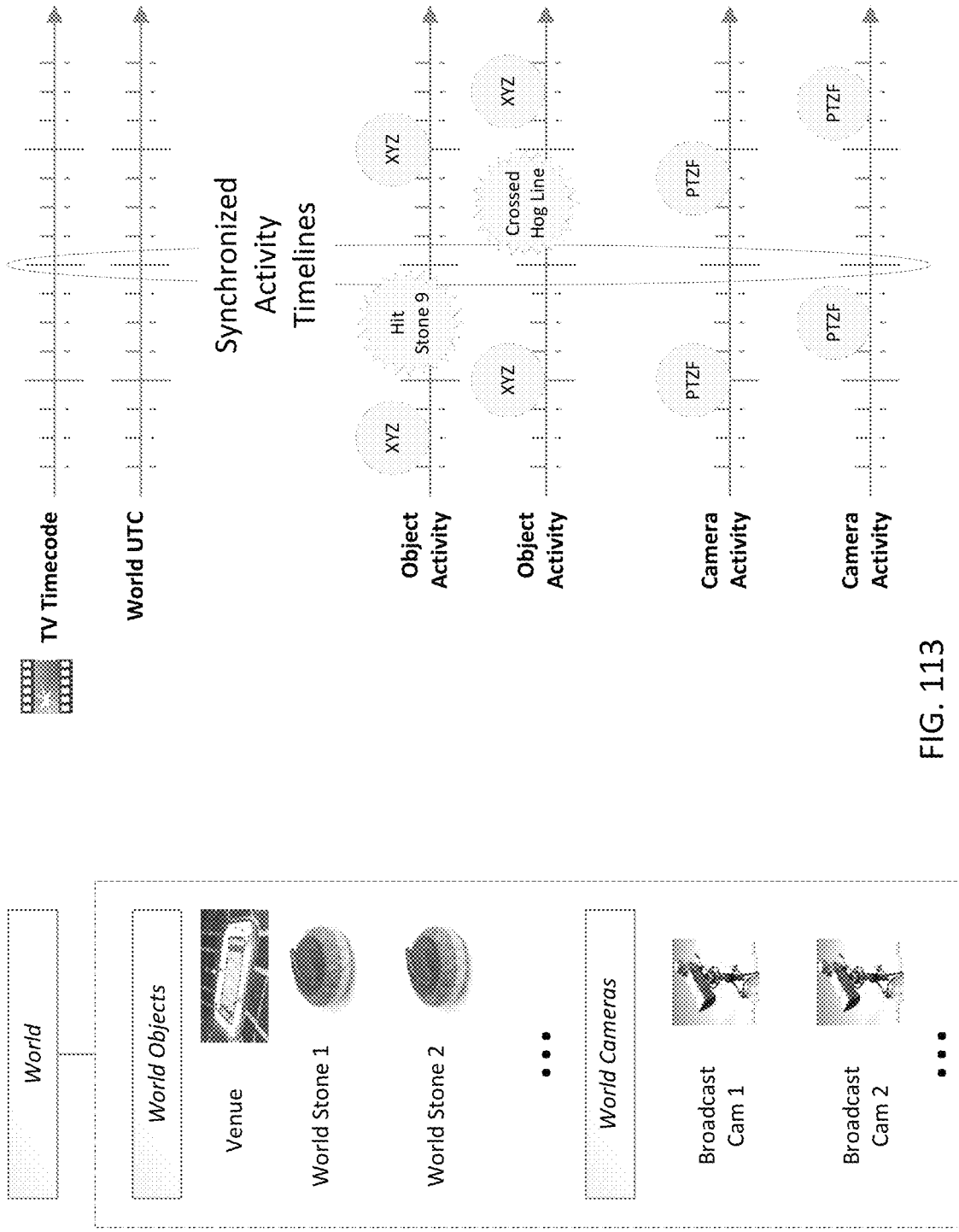
FIG. 113 is an illustration of activity synchronization according to one embodiment of the present invention.

FIG. 113 is an illustration of activity synchronization according to one embodiment of the present invention. Each world activity is timestamped with a world UTC timecode. World activities include world object activities, world camera activities, and competition events. World objects include venues, sports elements, and players. Sports elements include any sports equipment such as balls (e.g., football, basketball, tennis ball, soccer ball, golf ball, etc.), pucks, etc., wearable sporting equipment such as protective equipment (e.g.: helmet, shin guards, padding, etc.) and uniforms, and handheld equipment (e.g., racquet, lacrosse stick, baseball bat, golf club, hockey stick, etc.) Alternatively, the world objects of players include wearable sporting equipment. World camera activities include XYZ location changes, Pan-Tilt-Zoom-Focus (PTZF) value changes, etc. Each world object activity and each world camera activity are timestamped so that each world object and each world camera have their own individual activity timelines. In one embodiment, the world UTC is synchronized to a TV timecode for broadcast purposes. In one embodiment, multiple world UTCs are synchronized between each other. In one embodiment, multiple world UTCs are also synchronized to multiple TV timecodes.

Figure 114:
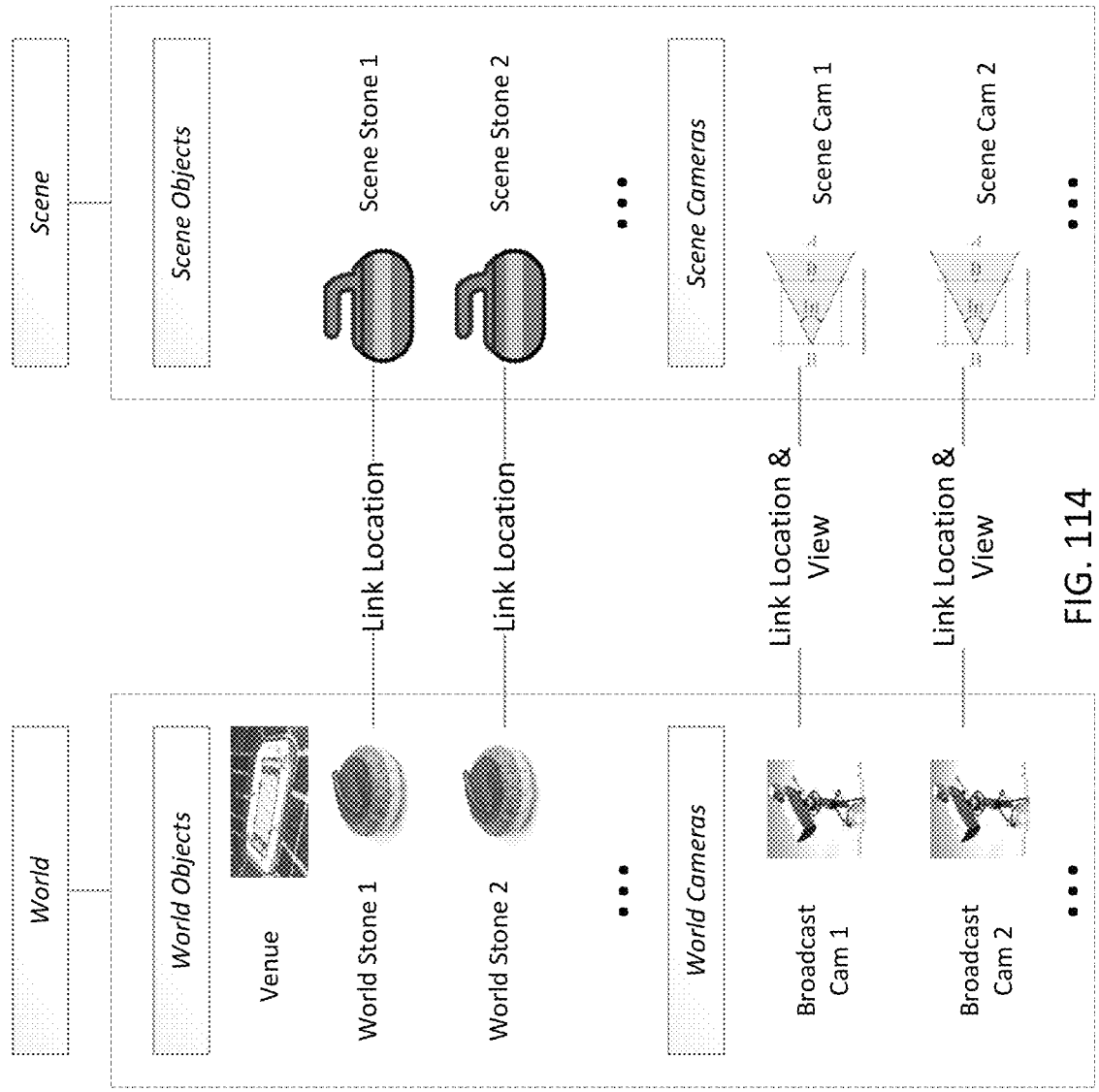
FIG. 114 is an illustration of mapping world objects and scene objects according to one embodiment of the present invention.

FIG. 114 is an illustration of mapping world objects and scene objects according to one embodiment of the present invention. The world represents the actual 3D physical world environment including objects and cameras placed within that environment. The scene is a 3D graphics scene representing a particular visualization of the world. Cameras are also included in the scene in order to change viewpoint. In one embodiment, a scene object is set to automatically track the location of a corresponding world object, and a scene camera is set to automatically track the location and view of a world camera.

The foregoing mentioned "cloud-based platform" refers to any software as a service or to services over at least one server or more than one server interfacing through the internet. In alternative embodiments, L1 in the present invention can be one or more local and physical servers, which will be appreciated by those with ordinary skill in the art.

The present invention, as a whole, is implemented through an unconventional and non-generic combination of physical elements providing sports data collection, advanced analytics and application in a time-sensitive and device-agnostic manner with real time network communication. The platform of the present invention provides improvement to sports data collection and aggregation and digestion, therefore, more valuable data are fed to coaches, trainers, medical staff, live announcers, broadcasters, displays, viewers, fans, and any other party relevant to a sports game, practice, event, activity or training. The present invention is inextricably tied to computer technology and communication.

Certain modifications and improvements will occur to those skilled in the art upon a reading of the foregoing description. The above-mentioned examples are provided to serve the purpose of clarifying the aspects of the invention and it will be apparent to one skilled in the art that they do not serve to limit the scope of the invention. All modifications and improvements have been deleted herein for the sake of conciseness and readability but are properly within the scope of the present invention.

What is claimed is:

1. A system for data analytics for a sports activity, comprising:
   at least one server platform constructed and configured for network communication with a multiplicity of sensor devices;
   wherein the multiplicity of sensor devices are operable to track a multiplicity of world objects related to the sports activity, and collect data inputs related to the sports activity in real time or near real time, thereby creating sports data;
   wherein the at least one server platform is operable to receive and integrate the sports data related to the sports activity from the multiplicity of sensor devices in real time or near real time;
   wherein the at least one server platform is operable to automatically correlate the sports data with a corresponding Coordinated Universal Time (UTC) timecode based on rules related to the sports activity, thereby creating a multiplicity of UTC-coded data sets;
   wherein the at least one server platform is operable to synchronize the multiplicity of UTC-coded data sets in real time or near real time, thereby creating a time-synchronized data set;
   wherein the at least one server platform is operable to provide analytics based on the time-synchronized data set in real time or near real time, thereby creating analyzed data; and
   wherein the at least one server platform is further operable to normalize and synchronize the sports data related to the sports activity.

2. The system of claim 1, wherein the at least one server platform is further operable for data archiving, post data playback, live data push, sport-specific triggering, and event context mapping.

3. The system of claim 1, further comprising at least one user device in network communication with the at least one server platform, wherein the at least one user device comprises at least one application program in network communication with the at least one server platform.

4. The system of claim 3, wherein the at least one user device is operable to display the analyzed data via the at least one application program.

5. The system of claim 1, wherein the at least one server platform is operable to synchronize and process the sports data into a unique data format along a timeline.

6. The system of claim 5, wherein the unique data format is compatible with a multiplicity of sports types.

7. The system of claim 5, wherein the unique data format includes three-dimensional data.

8. The system of claim 1, wherein the at least one server platform comprises at least one local server.

9. The system of claim 1, wherein the at least one server platform comprises a cloud-based server platform.

10. The system of claim 1, wherein the at least one server platform is operable to generate and update a multiplicity of object models based on the sports data.

11. The system of claim 10, wherein the multiplicity of object models comprise at least one game object model, at least one player object model, or at least one player stats object model.

12. The system of claim 1, wherein the multiplicity of world objects comprise a multiplicity of players, at least one sports element, and at least one venue.

13. The system of claim 1, wherein the at least one server platform is further operable to store the time-synchronized data set and the analyzed data for the sports activity.

14. The system of claim 1, wherein the at least one server platform is further operable to render a 3-dimensional (3D) graphics scene for the sports activity, map the multiplicity of world objects to a multiplicity of scene objects in the 3D graphics scene, and map world activities to scene activities in the 3D graphics scene.

15. The system of claim 14, wherein the world activities comprise world object activities, world camera activities, and competition events in the sports activity.

16. A system for data analytics for a sports activity, comprising:
- at least one server platform constructed and configured for network communication with a multiplicity of sensor devices;
- wherein the multiplicity of sensor devices are operable to track a multiplicity of world objects related to the sports activity, and collect data inputs related to the sports activity in real time or near real time, thereby creating sports data;
- wherein the at least one server platform is operable to receive and integrate the sports data related to the sports activity from the multiplicity of sensor devices in real time or near real time;
- wherein the at least one server platform is operable to automatically correlate the sports data with a corresponding Coordinated Universal Time (UTC) timecode based on rules related to the sports activity, thereby creating a multiplicity of UTC-coded data sets;
- wherein the at least one server platform is operable to synchronize the multiplicity of UTC-coded data sets in real time or near real time, thereby creating a time-synchronized data set;
- wherein the at least one server platform is operable to provide analytics based on the time-synchronized data set in real time or near real time, thereby creating analyzed data; and
- wherein the at least one server platform is operable to synchronize and process the sports data into a unique data format along a timeline.

17. The system of claim 16, wherein the unique data format is compatible with a multiplicity of sports types.

18. A system for data analytics for a sports activity, comprising:
- at least one server platform constructed and configured for network communication with a multiplicity of sensor devices;
- wherein the multiplicity of sensor devices are operable to track a multiplicity of world objects related to the sports activity, and collect data inputs related to the sports activity in real time or near real time, thereby creating sports data;
- wherein the at least one server platform is operable to receive and integrate the sports data related to the sports activity from the multiplicity of sensor devices in real time or near real time;
- wherein the at least one server platform is operable to automatically correlate the sports data with a corresponding Coordinated Universal Time (UTC) timecode based on rules related to the sports activity, thereby creating a multiplicity of UTC-coded data sets;
- wherein the at least one server platform is operable to synchronize the multiplicity of UTC-coded data sets in real time or near real time, thereby creating a time-synchronized data set;
- wherein the at least one server platform is operable to provide analytics based on the time-synchronized data set in real time or near real time, thereby creating analyzed data; and
- wherein the at least one server platform is operable to generate and update a multiplicity of object models based on the sports data.

19. The system of claim 18, wherein the multiplicity of object models comprise at least one game object model, at least one player object model, or at least one player stats object model.

* * * * *